US012350988B2

United States Patent
Anderson et al.

(10) Patent No.: US 12,350,988 B2
(45) Date of Patent: Jul. 8, 2025

(54) METHODS AND SYSTEMS FOR CONTROLLING VEHICLE BODY MOTION AND OCCUPANT EXPERIENCE

(71) Applicant: ClearMotion, Inc., Billerica, MA (US)

(72) Inventors: Zackary Martin Anderson, Cambridge, MA (US); Marco Giovanardi, Melrose, MA (US); Jack A. Ekchian, Belmont, MA (US); Olivia D. Godwin, Waterloo (CA); Clive Tucker, Charlestown, MA (US); John A. Laplante, Concord, NH (US); William Graves, Somerville, MA (US); Shakeel Avadhany, Cambridge, MA (US); Michael W. Finnegan, Medford, MA (US)

(73) Assignee: ClearMotion, Inc., Billerica, MA (US)

( * ) Notice: Subject to any disclaimer, the term of this patent is extended or adjusted under 35 U.S.C. 154(b) by 0 days.

(21) Appl. No.: 18/503,176

(22) Filed: Nov. 6, 2023

(65) Prior Publication Data
US 2024/0181827 A1    Jun. 6, 2024

Related U.S. Application Data

(63) Continuation of application No. 17/508,740, filed on Oct. 22, 2021, now Pat. No. 11,850,904, which is a
(Continued)

(51) Int. Cl.
*B60G 17/016*    (2006.01)
*A61B 5/00*    (2006.01)
(Continued)

(52) U.S. Cl.
CPC ......... *B60G 17/016* (2013.01); *A61B 5/4023* (2013.01); *B60G 17/0165* (2013.01);
(Continued)

(58) Field of Classification Search
CPC .............. B60G 17/016; B60G 17/0157; B60G 17/015; B60G 17/0165; B60G 17/018;
(Continued)

(56) References Cited

U.S. PATENT DOCUMENTS 3,937,058 A * 2/1976 Hilbrands ............ B60G 17/06
73/11.08
3,947,004 A    3/1976 Taylor
(Continued)

FOREIGN PATENT DOCUMENTS

| CA | 2705098 A1 * | 5/2009 | ........... A47C 15/004 |
|---|---|---|---|
| CN | 104360679 A * | 2/2015 | ......... G05B 23/0213 |

(Continued)

OTHER PUBLICATIONS

IEEE Transactions on Vehicular Technology, vol. 59, No. 3, Mar. 2010 "Active Electromagnetic Suspension System forImproved Vehicle Dynamics" (Year: 2010).*
(Continued)

*Primary Examiner* — Yuri Kan
(74) *Attorney, Agent, or Firm* — Wolf, Greenfield & Sacks, P.C.

(57) ABSTRACT

In one embodiment, one or more suspension systems of a vehicle may be used to mitigate motion sickness by limiting motion in one or more frequency ranges. In another embodiment, an active suspension may be integrated with an autonomous vehicle architecture. In yet another embodiment, the active suspension system of a vehicle may be used to induce motion in a vehicle. The vehicle may be used as a testbed for technical investigations and/or as a platform to enhance the enjoyment of video and/or audio by vehicle occupants. In some embodiments, the active suspensions system may be used to perform gestures as a means of communication with persons inside or outside the vehicle. In
(Continued)

some embodiments, the active suspensions system may be used to generate haptic warnings to a vehicle operator or other persons in response to certain road situations.

22 Claims, 46 Drawing Sheets

Related U.S. Application Data continuation of application No. 16/522,910, filed on Jul. 26, 2019, now Pat. No. 11,192,420, which is a continuation of application No. 15/833,738, filed on Dec. 6, 2017, now Pat. No. 10,513,161, which is a continuation of application No. 15/303,395, filed as application No. PCT/US2016/035926 on Jun. 3, 2016, now Pat. No. 9,868,332.

(60) Provisional application No. 62/304,901, filed on Mar. 7, 2016, provisional application No. 62/296,325, filed on Feb. 17, 2016, provisional application No. 62/192,051, filed on Jul. 13, 2015, provisional application No. 62/182,420, filed on Jun. 19, 2015, provisional application No. 62/170,674, filed on Jun. 3, 2015.

(51) Int. Cl.
| | | |
|---|---|---|
| *B60G 17/015* | (2006.01) | |
| *B60G 17/0165* | (2006.01) | |
| *B60G 17/019* | (2006.01) | |
| *B60G 17/0195* | (2006.01) | |
| *B60G 17/04* | (2006.01) | |
| *B60G 17/052* | (2006.01) | |
| *B60G 17/06* | (2006.01) | |
| *B60G 99/00* | (2010.01) | |
| *B60K 35/00* | (2024.01) | |
| *B60K 35/25* | (2024.01) | |
| *B60K 35/28* | (2024.01) | |
| *B60N 2/02* | (2006.01) | |
| *B60N 2/14* | (2006.01) | |
| *B60N 2/50* | (2006.01) | |

(52) U.S. Cl.
CPC ....... *B60G 17/019* (2013.01); *B60G 17/0195* (2013.01); *B60G 99/002* (2013.01); *B60K 35/00* (2013.01); *B60N 2/0273* (2023.08); *B60N 2/0276* (2013.01); *B60N 2/14* (2013.01); *B60N 2/501* (2013.01); *B60G 2400/05* (2013.01); *B60G 2600/182* (2013.01); *B60G 2800/012* (2013.01); *B60G 2800/014* (2013.01); *B60G 2800/016* (2013.01); *B60K 35/25* (2024.01); *B60K 35/28* (2024.01); *B60K 2360/178* (2024.01); *B60N 2/0268* (2023.08); *B60N 2210/24* (2023.08); *B60N 2220/10* (2023.08)

(58) Field of Classification Search
CPC ...... B60G 3/20; B60G 17/0162; B60G 17/06; B60G 17/0155; B60G 17/0416; B60G 17/052; B60G 17/04; B60N 2/501; B60N 2/50; A63G 31/16; G01M 17/04
See application file for complete search history.

(56) References Cited

U.S. PATENT DOCUMENTS

| | | | | |
|---|---|---|---|---|
| 5,231,583 A | * | 7/1993 | Lizell | B60G 17/015 |
| | | | | 280/5.506 |
| 5,255,191 A | * | 10/1993 | Fulks | B60G 17/018 |
| | | | | 280/5.515 |
| 5,393,087 A | * | 2/1995 | Taniguchi | B60G 17/0155 |
| | | | | 280/5.514 |
| 5,477,947 A | * | 12/1995 | Schalles | B60G 17/0416 |
| | | | | 188/298 |
| 5,551,920 A | * | 9/1996 | Ogden | A63G 31/16 |
| | | | | 434/55 |
| 8,781,681 B2 | | 7/2014 | Parison, Jr. et al. | |
| 8,892,304 B2 | | 11/2014 | Lu et al. | |
| 10,300,760 B1 | | 5/2019 | Aikin et al. | |
| 11,192,420 B2 | * | 12/2021 | Anderson | B60G 17/0162 |
| 11,850,904 B2 | | 12/2023 | Anderson et al. | |
| 2006/0095180 A1 | * | 5/2006 | Ummethala | B60N 2/501 |
| | | | | 701/37 |
| 2007/0278057 A1 | | 12/2007 | Wereley et al. | |
| 2008/0054540 A1 | * | 3/2008 | Buma | B60G 17/0162 |
| | | | | 267/195 |
| 2008/0275606 A1 | | 11/2008 | Tarasinski et al. | |
| 2010/0023211 A1 | * | 1/2010 | Ammon | B60G 17/0165 |
| | | | | 701/37 |
| 2013/0030650 A1 | * | 1/2013 | Norris | B60G 17/018 |
| | | | | 701/40 |
| 2013/0340524 A1 | * | 12/2013 | Maeda | G01P 15/125 |
| | | | | 73/514.02 |
| 2014/0001717 A1 | * | 1/2014 | Giovanardi | B60G 17/0165 |
| | | | | 280/5.518 |
| 2014/0005888 A1 | * | 1/2014 | Bose | B60G 17/0165 |
| | | | | 701/37 |
| 2014/0284122 A1 | * | 9/2014 | Hirata | B60G 3/20 |
| | | | | 180/65.51 |
| 2015/0120149 A1 | | 4/2015 | Worrel et al. | |
| 2016/0347143 A1 | * | 12/2016 | Hrovat | B60W 30/095 |
| 2017/0120932 A1 | | 5/2017 | Szczerba et al. | |
| 2017/0129335 A1 | | 5/2017 | Lu et al. | |
| 2017/0182859 A1 | * | 6/2017 | Anderson | B60G 17/019 |
| 2017/0203627 A1 | * | 7/2017 | Selden | B60G 17/0157 |
| 2022/0126640 A1 | | 4/2022 | Anderson et al. | |

FOREIGN PATENT DOCUMENTS

| | | | | |
|---|---|---|---|---|
| DE | 102009060213 A1 | 6/2011 | | |
| DE | 102010048822 A1 | 4/2012 | | |
| DE | 10 2015 015 306 A1 | 5/2016 | | |
| EP | 0162818 A1 | 11/1985 | | |
| EP | 0963867 A1 | 12/1999 | | |
| EP | 2233332 A2 | 9/2010 | | |
| EP | 2431218 A1 | 3/2012 | | |
| EP | 2362261 B1 | 4/2018 | | |
| JP | 06219132 A | * | 8/1994 | ........... B60C 17/015 |
| JP | H06-092159 B2 | 11/1994 | | |
| JP | H09-044077 A | 2/1997 | | |
| JP | 10109581 A | * | 4/1998 | ............... B60N 2/50 |
| JP | 2004-299570 A | 10/2004 | | |
| JP | 2005-326962 A | 11/2005 | | |
| JP | 2006-047478 A | 2/2006 | | |
| JP | 2007-118742 A | 5/2007 | | |
| JP | 2007-219098 A | 8/2007 | | |
| JP | 2008-120271 A | 5/2008 | | |
| JP | 2008-265692 A | 11/2008 | | |
| KR | 960010339 U | 4/1996 | | |
| KR | 20080092396 A | 10/2008 | | |
| KR | 20090128868 A | 12/2009 | | |
| KR | 20130039959 A | 4/2013 | | |
| WO | WO-9733451 A1 | * | 9/1997 | ............... G09B 9/02 |
| WO | WO 2006/015592 A1 | 2/2006 | | |
| WO | WO 2013/190612 A1 | 12/2013 | | |

OTHER PUBLICATIONS

U.S. Appl. No. 15/303,395, filed Oct. 11, 2016, Anderson et al.
U.S. Appl. No. 15/833,738, filed Dec. 6, 2017, Anderson et al.
U.S. Appl. No. 16/522,910, filed Jul. 26, 2019, Anderson et al.
U.S. Appl. No. 17/508,740, filed Oct. 22, 2021, Anderson et al.
U.S. Appl. No. 17/920,642, filed Oct. 21, 2022, Giovanardi et al.
PCT/US2016/035926, Oct. 6, 2016, International Search Report and Written Opinion.
PCT/US2016/035926, Dec. 14, 2017, International Preliminary Report on Patentability.

(56) References Cited

OTHER PUBLICATIONS

EP23166726.2, Oct. 10, 2023, Extended European Search Report.
International Search Report and Written Opinion dated Oct. 6, 2016 in connection with International Application No. PCT/US2016/035926.
International Preliminary Report on Patentability dated Dec. 14, 2017 in connection with International Application No. PCT/US2016/035926.
Extended European Search Report dated Oct. 10, 2023 for European Application No. 23166726.2.
Gysen et al., Active Electromagnetic Suspension System for Improved Vehicle Dynamics. IEEE Transactions on Vehicular Technology. 2010;59(3):1156-63.
Karlsson et al., Motion Sickness—Physiological and psychological influences on motion sickness. Jan. 1, 2012. pp. 1-90, XP055543941. Retrieved on Jan. 17, 2019 from the Internet: http://publications.lib.chalmers.se/records/fulltext/162898.pdf.

\* cited by examiner

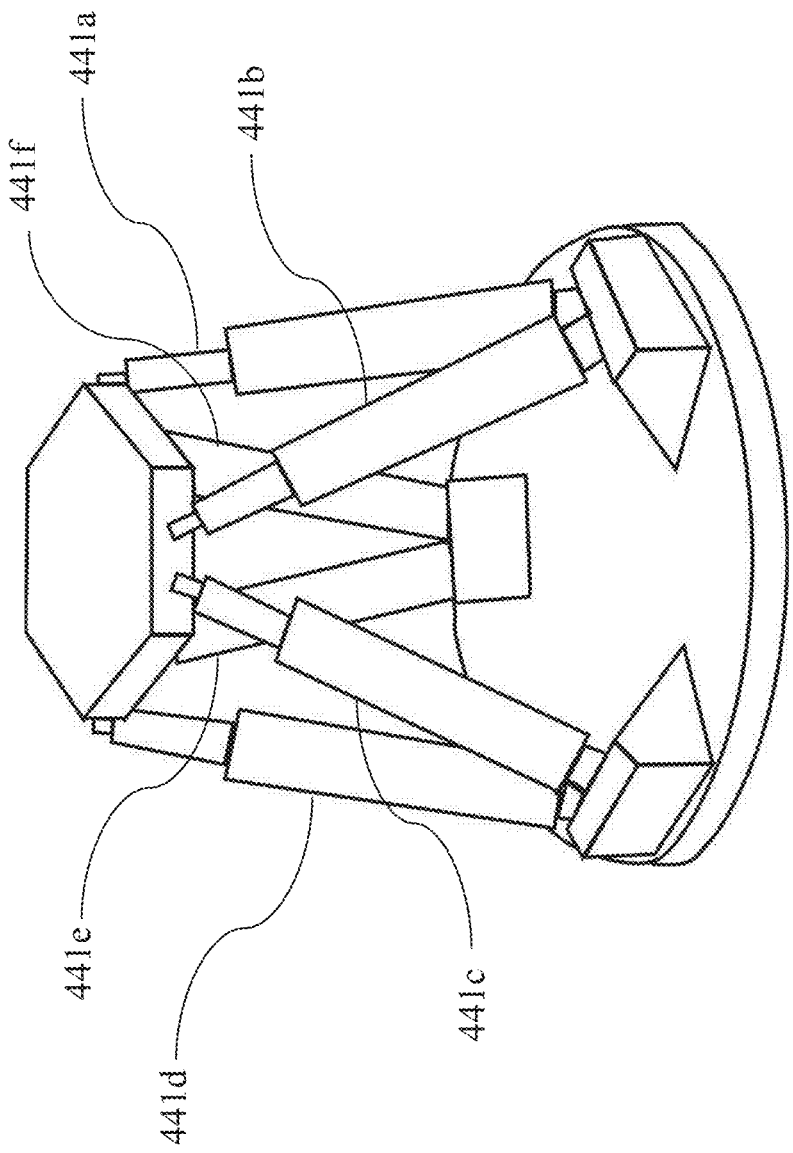

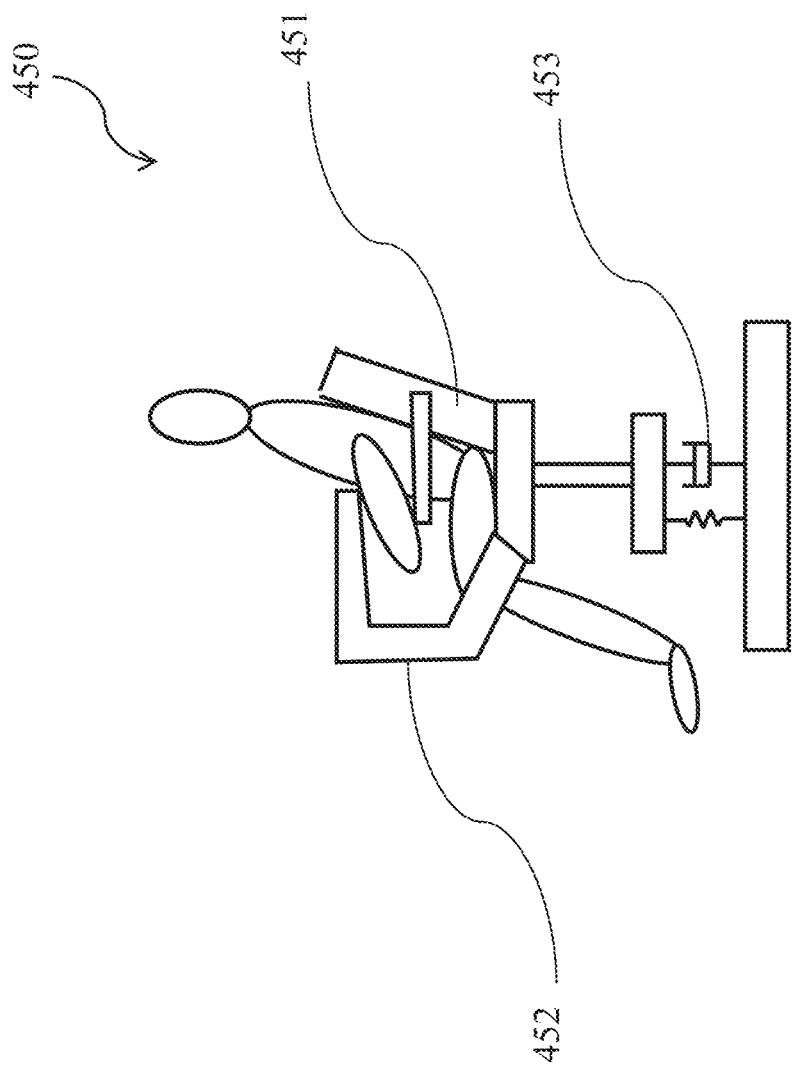

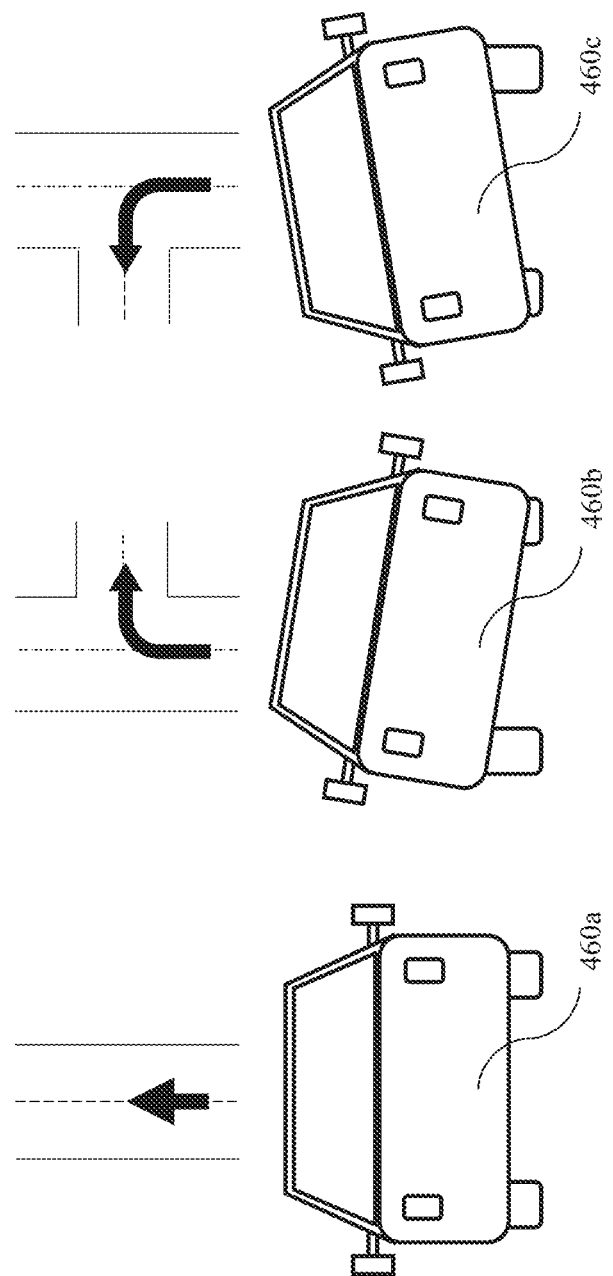

METHODS AND SYSTEMS FOR CONTROLLING VEHICLE BODY MOTION AND OCCUPANT EXPERIENCE

CROSS REFERENCE OF RELATED APPLICATIONS

This application is a continuation of U.S. application Ser. No. 17/508,740, filed Oct. 22, 2021, which is a continuation of U.S. application Ser. No. 16/522,910, filed Jul. 26, 2019, which is a continuation of U.S. application Ser. No. 15/833,738, filed on Dec. 6, 2017, which is a continuation of U.S. application Ser. No. 15/303,395, filed on Oct. 11, 2016, which is a national stage filing under 35 U.S.C. § 371 of International Application Serial No. PCT/US2016/035926 filed Jun. 3, 2016, which claims the benefit of priority under U.S.C. § 119(e) of U.S. Provisional Application Ser. No. 62/170,674, filed Jun. 3, 2015, U.S. Provisional Application Ser. No. 62/182,420, filed Jun. 19, 2015, U.S. Provisional Application Ser. No. 62/192,051, filed Jul. 13, 2015, U.S. Provisional Application Ser. No. 62/296,325, filed Feb. 17, 2016, and U.S. Provisional Application Ser. No. 62/304,901, filed Mar. 7, 2016, the disclosures of each of which are incorporated herein by reference in their entirety.

FIELD

Disclosed embodiments are related to methods and systems for controlling vehicle body motion and occupant experience.

BACKGROUND

Autonomous vehicles are expected to revolutionize transportation because, for example, they offer the opportunity for flexible personalized transportation with expectations for significant increases in occupant safety due to the elimination of "driver error." Autonomous vehicles can be both personal and shared, as well as deliver increased fuel economy. However, occupants of autonomous and semi-autonomous, as well as conventionally driven vehicles, may experience motion sickness due to, for example, the inability to anticipate motion, a lack of control over the direction of movement, and/or exposure to specific patterns and frequencies of movement. Further, use of autonomous and semi-autonomous vehicles is expected to lead to an increase in the frequency and severity of motion sickness experienced by the traveling public on a daily basis. One reason why this is expected is because occupants of such vehicles will be further isolated and removed from the decision making process that determines the vehicle's route and how it is traveled. Additionally, while people are generally able to adapt to conditions that can cause motion sickness, there are large differences in the rates and degree of adaptability among individuals which may be effected by conditions, such as sleep deprivation, that may make a person more susceptible to motion sickness.

SUMMARY

In one embodiment, a method of mitigating motion sickness in a vehicle includes: mitigating motion of at least a portion of the vehicle within a first frequency range by a first degree during a first mode of operation; detecting an event indicating an increased likelihood of motion sickness of at least one occupant of the vehicle; and mitigating motion of the portion of the vehicle body within the first frequency range by a second degree different than the first degree during a second mode of operation.

In another embodiment, a vehicle includes an active suspension system and an active suspension system controller in electrical indication with the active suspension system. The vehicle also includes at least one sensor or an input in electrical communication with the controller, where the controller detects an increased likelihood of motion sickness of an occupant of the vehicle using information from the at least one sensor or input. Further, the controller operates the active suspension system to mitigate motion in a first frequency range to a greater degree when an increased likelihood of motion sickness of the occupant has been detected.

In yet another embodiment, a method of operating an active suspension system of a vehicle includes: detecting movement of a vehicle chassis within a first frequency range with a first magnitude; and operating the active suspension system of the to induce motion in the vehicle chassis within a second frequency range with a second magnitude.

In another embodiment, a method of reducing motion within a vehicle includes: operating a first suspension system associated with a first portion of the vehicle first portion of the vehicle to reduce motion of the first portion of the vehicle in at least a first range of frequencies; and operating a second suspension system located between first portion of the vehicle and the second portion of the vehicle to reduce motion of the second portion of the vehicle in at least a second range of frequencies, wherein at least a portion of the second range of frequencies is different from the first range of frequencies.

In yet another embodiment, a method of reducing a motion of at least a first portion of a vehicle includes: detecting a first force applied to the first portion of a vehicle; and moving a mass associated with the first portion of the vehicle to apply a second force to the first portion of the vehicle in a direction that opposes the first force.

In another embodiment, a method of operating a vehicle includes: detecting a situation; and inducing movement in at least a portion of the vehicle to alert a vehicle occupant to the situation.

In another embodiment, a method of mitigating motion sickness in a moving autonomous vehicle includes: operating the autonomous vehicle on a road; and operating an active suspension system of the autonomous vehicle to induce a motion to the autonomous vehicle to inform at least one occupant of the vehicle that a maneuver of the autonomous vehicle will occur prior to performing the maneuver.

In yet another embodiment, a vehicle includes an active suspension system that includes at least one actuator and a vehicle control system that selectively operates the vehicle in one of an autonomous state and a conventionally driven state. Further, the active suspension system is operated in a first mode when the vehicle is operated in the autonomous state and in a second mode when the vehicle is in a conventionally driven state.

In another embodiment, a method for operating a vehicle includes: operating the vehicle in an autonomous state; operating an active suspension system of the vehicle in a first mode when the vehicle is operated in the autonomous state; operating the vehicle in a conventionally driven state; and operating the active suspension system of the vehicle in a second mode when the vehicle is operated in the conventionally driven state.

In yet another embodiment, a method of mitigating motion sickness includes: displaying an image on a display; detecting movements of the display with frequencies greater than a threshold frequency; and moving the image within the display based at least partially on the detected movements with frequencies greater than the threshold frequency.

In another embodiment, a method of operating a vehicle that includes an active suspension system includes: playing at least one of video and audio within the vehicle; and operating at least one actuator of the active suspension system to induce motion in at least a portion of the vehicle, wherein at least one aspect of the induced motion is synchronized with at least one aspect of the video and/or the audio.

In yet another embodiment, a human-machine interface for a vehicle suspension system includes at least one vehicle sensor that senses information related to at least one aspect of an interaction of the suspension system with a road surface. An suspension system controller is in electrical communication with the suspension system. Further, a display displays information about the at least one aspect of the interaction of the suspension with the road surface based on at least one of the sensed information and suspension status information from the suspension system controller.

In another embodiment, a method for determining wheel imbalance on a moving vehicle includes: averaging a centripetal force of a wheel of the moving vehicle in a first direction over a predetermined period of time; determining an angular orientation of the wheel corresponding to a maximum measured centripetal force of the wheel; and updating a wheel imbalance status of the wheel within a vehicle database based on the determined angular orientation and maximum measured centripetal force of the wheel.

In yet another embodiment, a diagnostics method for a vehicle with an active suspension system includes: using an active suspension system to induce a predetermined motion in at least a portion of the vehicle; measuring the response of at least the portion of the vehicle with a sensor; comparing the measured response with a predetermined expected response of the vehicle; and updating a status of at least one component of the vehicle within a vehicle database based on the comparison.

In another embodiment, a high precision hybrid road mapping system for vehicles, includes a database containing low granularity large scale positioning data and a high granularity localized positioning data that includes information about the relative spacing of road features collected. The localized positioning data may be at least partially collected from on the road vehicles. Further, the accuracy of the large scale positioning data may be improved by incorporating the relative position information of the localized positioning data.

In yet another embodiment, a method of operating a vehicle active suspension system as an audio enhancer includes: receiving an audio signal; filtering the audio signal with a filter; providing the filtered signal from the filter to an active suspension controller; and operating at least one active suspension actuator with the active suspension controller to induce low frequency vibrations in a least a portion of the vehicle body, wherein the induced vibrations are a function of the filtered audio signal.

In another embodiment, a method of operating an active suspension system includes: operating an active suspension actuator to replicate a force/velocity curve of a passive automotive damper.

In yet another embodiment, a method of operating an active suspension system of a vehicle includes: recording active suspension settings selected by an occupant of the vehicle; obtaining identifying information about the occupant; correlating the active suspension system setting with the occupant's identifying information; and storing the correlated data in a vehicle database.

In another embodiment, a method of operating an active suspension system in a parked vehicle includes: using an active suspension system to move at least one portion of the vehicle body of a parked vehicle; and moving the at least one portion of the vehicle body in a predefined pattern of motion.

In yet another embodiment, an active suspension system includes at least one actuator capable of providing a force between a wheel and a vehicle chassis and a controller that commands force from the at least one actuator. The system also includes an input operatively connected to an audio signal and at least one sensor that senses at least one of a road, wheel, and chassis motion. The controller force command is a function of both the audio signal and the at least one sensor.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF FIGURES

The accompanying drawings are not intended to be drawn to scale. In the drawings, each identical or nearly identical component that is illustrated in the various figures may be represented by a like numeral. For purposes of clarity, not every component may be labeled in every drawing. In the drawings:

FIG. 24 is schematic representation of an embodiment of a system including a hexapod mechanism;

FIG. 25 is schematic representation of an embodiment of a system including an isolated seat and work surface;

FIG. 26 is schematic representation of an embodiment of a system that uses one or more vehicle movements to indicate upcoming maneuvers;

DETAILED DESCRIPTION

Figure 1:
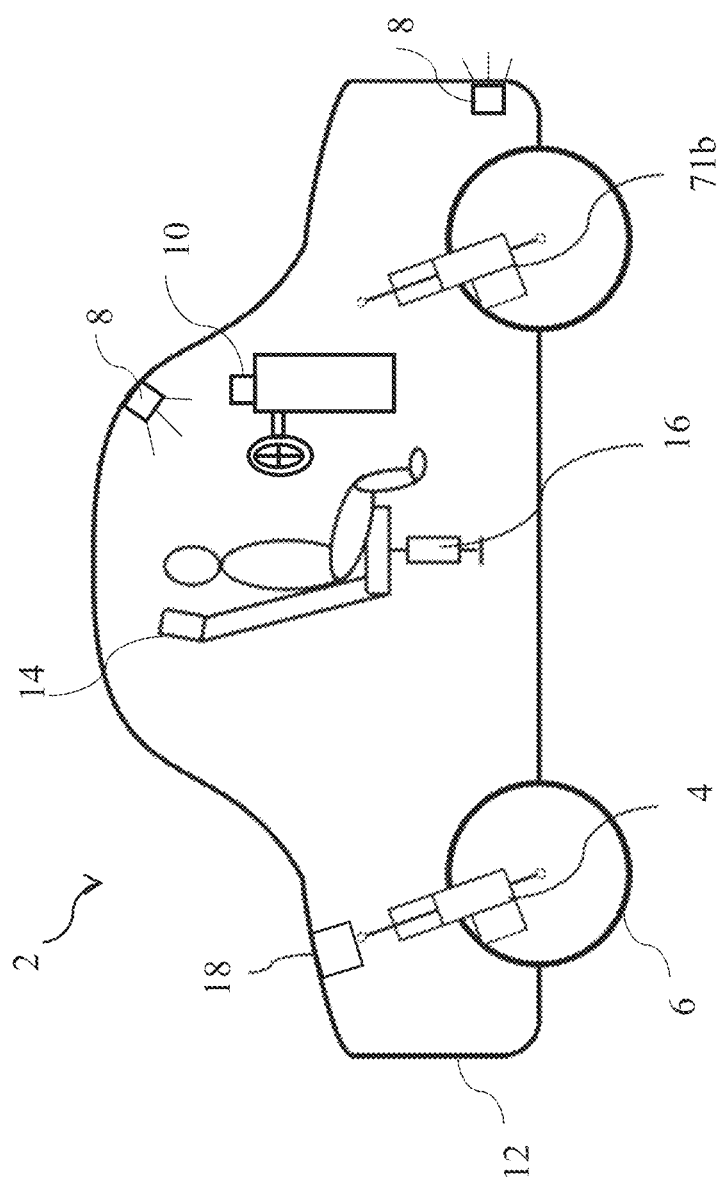
FIG. 1 is a schematic representation of a vehicle.

Due to the expected increase in use of autonomous and semi-autonomous vehicles, the Inventors have recognized that it may be beneficial to provide systems and methods for reducing the likelihood of motion sickness in occupants of a vehicle. In view of the above, the Inventors have recognized the benefits associated with mitigating, or otherwise reducing, motion of one or more portions of a vehicle for one or more frequency ranges. Additionally, in some embodiments, this reduction in movement of the vehicle may be done in response to one or more situations indicating an increased chance of motion sickness for an occupant of the vehicle. Alternatively, the methods and systems described herein may be implemented preemptively to reduce, and/or possibly prevent, situations that may lead to motion sickness of a vehicle occupant. Therefore, some of the embodiments discussed herein are generally related to systems and methods used to control the motion of one or more portions of a vehicle under various circumstances to enhance the in-vehicle experience of vehicle occupants. However, other embodiments described herein are related to a more enjoyable and/or effective human machine interfaces.

Depending on the particular embodiment, various systems of a vehicle may be operated to reduce, or eliminate, motion transmitted to a particular portion of the vehicle and/or a vehicle occupant. Systems that may be controlled include, but are not limited to, suspension systems associated with various portions of a vehicle such as a vehicle body, a passenger compartment, and/or structures located within the passenger compartment as well as a throttle, braking, and/or steering controls of an autonomous, semi-autonomous and/or conventionally driven vehicle. Accordingly, one or more of these systems may be operated to avoid certain predefined, deduced, detected, or vehicle occupant identified motions or operating regimes that induce passenger discomfort, such as for example, motion sickness or fatigue as described further below.

Typically, designers have recognized that there is a higher likelihood of experiencing motion sickness symptoms, including nausea and dizziness, if a person, or a vehicle with an occupant inside, is exposed to lateral disturbances and/or vertical oscillations at low frequencies between about 0.05 Hz-0.5 Hz. However, the inventors have determined that motion sickness may also occur due to motions in various directions such as heave, pitch, and/or roll at higher frequencies such as, for example, in the range of 0.5 Hz-10 Hz. Further, a person's sensitivity to motions within this frequency range may be exacerbated if they are performing certain tasks such as reading, watching a video, playing a video game, or other activities in an environment where they are at least partially decoupled from controlling or otherwise being aware of the movement of their immediate environment as might occur in a vehicle. Consequently, one or more suspension systems, or movement mitigation devices, associated with one or more portions of a vehicle may be operated in order to mitigate motion to a vehicle occupant within either one, or both, of these frequency ranges to a greater degree in one or more modes of operation than is typically done in a vehicle.

In some embodiments, one or more suspension systems of a vehicle may be used to suppress motions, such as for example, heave, pitch, and/or roll, for one or more structures in a vehicle including a vehicle body (e.g. the chassis or frame), passenger compartment, structures within the passenger compartment (e.g. seats and works surfaces), and/or any other appropriate portion of the vehicle. Additionally, the one or more suspension systems may be operated to further reduce motions in one or more predetermined frequency ranges associated with motion sickness during at least one mode of operation, such as when it is desired to reduce the likelihood of motion sickness. In one embodiment, frequencies that may be associated with motion sickness include frequencies between about 0.05 Hz and 10 Hz. Further, the one or more active suspension systems may either operate over this entire range, or one or more sub ranges of this frequency range as the disclosure is not so limited. For example, a suspension system may mitigate motion at frequencies greater than or equal to about 0.05 Hz, 0.1 Hz, 0.2 Hz, 0.5 Hz, 1 Hz, 2 Hz, or any other appropriate frequency when it is desired to reduce motions with frequencies associated with motion sickness. Correspondingly, a suspension system may mitigate motion at frequencies less than or equal to about 10 Hz, 9 Hz, 8 Hz, 7 Hz, 6 Hz, 5 Hz, 1 Hz, or any other appropriate frequency when it is desired to reduce motions with frequencies associated with motion sickness. Combinations of the above ranges are contemplated including, for example, frequency ranges between or equal to about 0.05 Hz and 10 Hz, 0.1 Hz and 10 Hz, 0.5 Hz and 10 Hz, 1 Hz and 10 Hz, 2 Hz and 6 Hz, and/or any other appropriate combination as the disclosure is not so limited. Mitigation of motion at a particular frequency means that motion is mitigated in any frequency range that includes that particular frequency. Also, mitigating motion in a particular frequency range does not necessarily indicate that motion is mitigated uniformly throughout that range or even at each frequency in that range.

In the above noted embodiment, motions within such frequency ranges may be suppressed at certain times, and/or to varying degrees, depending on whether the vehicle is in an autonomous mode or in a conventionally driven mode and/or depending on input from one or more sources, such as for example, sensors and/or commands or signals from one or more vehicle occupants. Additionally, the one or more suspension systems associated with the vehicle may be any of a passive suspension system, a semi-active suspension system, an active suspension system, and/or a combination of the foregoing as the disclosure is not so limited.

The Inventors have recognized that in certain situations, such as for example, from an energy conservation and vehicle performance perspective, it may not be desirable to always provide enhanced motion mitigation within a particular frequency range. Instead, a vehicle may be operated in a first mode of operation until an event, series of events and/or pattern of events, that indicates an increased likelihood of motion sickness of a vehicle occupant, is detected. The vehicle may then be operated in a second mode that provides enhanced mitigation of motion in one or more frequency ranges to help reduce the likelihood, severity and/or duration of an occupant's motion sickness. In one such exemplary embodiment, a vehicle may include a suspension system, such as an active suspension system, or other appropriate motion mitigation device, that is used to reduce the transmission of movement to either the vehicle body, or other portion of the vehicle. In the first mode of operation, the suspension system is operated to mitigate motion to a portion of the vehicle within a first frequency range by a first-degree. After detecting the event, series of events and/or pattern of events, associated with an increased likelihood of motion sickness symptoms, the suspension system is operated in the second mode such that it provides increased mitigation of motion within the first frequency range to the portion of the vehicle than during the first mode of operation. Once the situation associated with an increased likelihood of motion sickness is over, or after a desired delay, the vehicle may be operated in a third mode of operation, which in some instances may be the same as the first mode. Consequently, in some embodiments, enhanced motion sickness mediation may be provided when needed and the vehicle may be operated in a lower power and/or more efficient mode and/or higher vehicle performance mode during other time periods.

As detailed further below, an event, or events, associated with an increased likelihood of motion sickness of a vehicle occupant may be determined in any number of ways. For example, in one embodiment, the event or events may be determined at least in part using information such as forces and/or accelerations applied to the vehicle as determined by one or more sensors associated with an active suspension system. Additionally, in some embodiments, an event, or events, may be determined at least in part using information such as forces and/or accelerations applied to an occupants head and/or torso based on measurements and or predetermined transfer functions that relate vehicle motion to the motion of an occupants head and/or torso.

Alternatively, in some embodiments, the information used to determine the likelihood of motion sickness may be based at least partially on feedback from a vehicle occupant. For example, a vehicle occupant may use a push-button, dial, touchpad, smart phone, tablet, or other mobile computing device with a computer app to communicate their level of discomfort to a controller of the active suspension system. In one such embodiment, the occupant may report a level of motion sickness between a lower and upper portion of a scale such as between 0-10 where a score of 0 is indicative of no symptoms and a score of 10 is indicative of imminent vomiting. In yet another embodiment, information about the likelihood of motion sickness may be based on data collected by sensors that are located within the vehicle. These may correspond to sensors integrated with the vehicle such as cameras or physiological sensors incorporated into portions of the vehicle that the occupants interact with such as the steering wheel, portions of a chair, or other appropriate portions of the vehicle. Additionally, the sensors may be integrated into devices that are worn or carried by a vehicle occupant, such as a wristband. In either case, the physiological sensors may be used to measures parameters such as body temperature, heart rate, how much the vehicle occupant is perspiring, ocular reflexes and other appropriate parameters associated with motion sickness.

As noted above, the Inventors have recognized that mitigating motions of a vehicle such as heave, pitch and/or roll over the frequency range 0.05 Hz to 10 Hz range, or over a sub-portion of that range, may reduce motion sickness in a significant portion of the population. This mitigation may be achieved by using a suspension system of a vehicle, such as a passive damping system, a semi-active suspension system, and/or an active suspension system. For example, one or more actuators of an active suspension system may be used to apply forces and reduce motion in one or more portions of the vehicle to counteract road induced forces applied to the vehicle body. Further, in some embodiments, additional suspension systems, motion mitigation devices, and/or passive damping techniques may be used to further reduce motions transmitted to a particular section of the vehicle such as a chair, passenger compartment and/or cab. Additionally, these different suspension systems and devices may either all operate within these noted frequency ranges and/or they may operate over only a portion of these frequency ranges as the disclosure is not so limited. For example, a primary suspension system of a vehicle may primarily mitigate motions at higher frequencies while the secondary suspension system associated with a sub-portion of the vehicle may primarily mitigate motions at lower frequencies as described further below.

In addition to mitigating motion, the Inventors have recognized the benefits associated with providing cues to vehicle occupants either to indicate specific situations and/or an expected maneuver of the vehicle. These cues may help enhance situational awareness of the vehicle occupants and/or help mitigate motion sickness. Consequently, in one embodiment, an active suspension system of a vehicle may be used to induce motion in one or more portions of a vehicle to indicate an expected vehicle maneuver such as a turn, acceleration, deceleration, and/or any other appropriate vehicle maneuver prior to it occurring. In another embodiment, a vehicle may detect a situation such as an imminent collision, a vehicle driving past lane markings on a road surface, an uneven load distribution, and/or an overload condition. An active suspension system of vehicle may then be used to induce motion in at least a portion of the vehicle to alert a vehicle occupant to the situation. Of course, it should be understood that any number of different types of motions may be used as a cue to indicate a particular situation or maneuver. For example, roll, pitch, heave, vibration of one or more wheels, a combination of the foregoing, and/or any other appropriate type of vehicle motion may be used to indicate a particular type of situation and/or vehicle maneuver as the disclosure is not so limited.

It should be understood that while many of the embodiments described herein are detailed relative to autonomous and semi-autonomous vehicles, the currently disclosed systems and methods for mitigating motion sickness and/or motion of a vehicle are not limited to use on autonomous and semi-autonomous vehicles. Instead, the described systems and methods may be implemented in any appropriate vehicle including conventionally driven vehicles as the disclosure is not so limited. Additionally, the methods and systems described herein may be used with autonomous, semi-autonomous, and/or conventionally driven vehicles that are powered with electric, hybrid, and/or internal combustion power plants. Further, depending on the particular embodiment, the vehicles may be equipped with either a passive suspension system, a semi-active suspension system, an active suspension system, or a combination of any of the forgoing as the methods and systems described herein are not limited in this fashion.

For the purposes of this disclosure, autonomous vehicles and self-driving vehicles may be understood to include at least any vehicle that executes combined function automation (NHTSA Level 2), limited self-driving automation (NHTSA Level 3), and/or full self-driving automation (NHTSA Level 4).

Turning now to the figures, certain exemplary embodiments are described further below to provide an overall understanding of the principles of the structure, function, manufacture, and use of the systems and methods disclosed herein. However, the systems, methods, and examples described herein and illustrated in the accompanying drawings are non-limiting exemplary embodiments and that the scope of the present disclosure is not limited to only the depicted embodiments. Instead, the features illustrated or described in connection with the various embodiments may be combined with features of other embodiments either individually and/or in various combinations. Such modifications are intended to be included within the scope of the present disclosure.

FIG. 1 depicts an embodiment of a vehicle 2 including a first suspension system 4 that may be used with the various methods and vehicle systems described herein. In the figure, the various dampers and/or actuators of the suspension system are disposed between the associated wheel or wheel assembly and vehicle body of vehicle. Further, each damper and/or actuator is capable of controlling the relative movement of at least a portion of the vehicle body 12 and the associated wheel 6 independently. Additionally, in some embodiments, the actuators and/or dampers of a suspension system may be used with various types of springs such as, for example, coil springs and/or air springs disposed between the associated portions of a vehicle in parallel or in series with respect to the actuators.

While a specific suspension system has been shown in the figure, any appropriate suspension system may be used. For example, conventional suspension systems typically use passive dampers that apply resistive forces to oppose compression and/or extension of the damper using largely constant operating and performance parameters. Additionally, some suspension systems are semi-active in that their overall response can be adjusted, for example, to offer a trade-off between occupant comfort and vehicle handling. Fully active suspension systems use actuators to react automatically to changing road conditions by relying on input from sensors and other devices. Therefore, an active damper, suspension system, actuator or other similar device may be used to apply a force in a compression and/or extension direction during a compression and/or extension stroke respectfully. Additionally, an active suspension system may also be used to apply resistive forces during some modes of operation. Therefore, in some embodiments, an active suspension system, or a sub-portion thereof, may operate in at least three of four quadrants of a force velocity diagram.

As also shown in FIG. 1, in some embodiments, a vehicle 2 may also include a second suspension system 16 associated with a second portion of the vehicle 14. In the depicted embodiment, the second portion of vehicle corresponds to a seat in which an occupant may be seated. However, embodiments in which the second portion of the vehicle corresponds to, for example, a passenger compartment, a cab, a loading compartment or any other appropriate portion of a vehicle are also contemplated as the disclosure is not so limited. As described in more detail below, the first suspension system may be used to mitigate motion of the vehicle body within one or more frequency ranges. The second suspension system may then be used concurrently to mitigate motion transferred to a second portion of the vehicle within one or more frequency ranges as well. While any appropriate kinematic characteristic may be used for either suspension system, in some embodiments, the first suspension system may reduce motion to a greater extent than the second suspension system in at least a first frequency range. Similarly, the second suspension system may reduce motion to a greater extent than the first suspension in at least a second range. For example, the first frequency range includes higher frequencies than the second frequency range which may offer a benefit of reduced power consumption as detailed further below.

While a vehicle including two suspension systems associated with different portions of the vehicle has been depicted above, embodiments in which a different number of suspension systems and/or a different number of portions of the vehicle associated with those suspension systems are also contemplated. For example, in one embodiment, a vehicle may simply include a primary suspension system located between the vehicle body and the wheels. Alternatively, in yet another embodiment, a vehicle may include a primary suspension system located between the vehicle and the wheels or wheel assemblies as well as a plurality of secondary suspension systems associated with separate portions of the vehicle. For example, a second suspension system may be associated with a passenger compartment and a third suspension system may be located between an occupant seat and the passenger compartment it is located within.

It should be understood that the active suspension systems depicted in the figures, and described throughout this application, may include any number of different types of actuators. Examples of such actuators may include electro-hydraulic, electromagnetic and electro-mechanical actuators. Electro-hydraulic actuators typically use a hydraulic pump, driven by an electric motor, to apply a desired force on an actuator piston. U.S. Pat. No. 8,839,920 entitled "Hydraulic Energy Transfer," filed Aug. 3, 2009, U.S. Pat. No. 9,035,477 entitled "Integrated Energy Generating Damper," filed Mar. 11, 2013, U.S. patent application Ser. No. 14/212,359, entitled "Integrated Active Suspension Smart Valve," filed Mar. 14, 2014, and U.S. patent application Ser. No. 14/602,463 entitled "Active Vehicle Suspension System," filed Jan. 22, 2015, which disclose examples of electro-hydraulic actuators and controllers for active suspension systems, are incorporated herein by reference in their entirety. Other active suspension systems may include electro-magnetic active suspension actuators that typically include linear electric motors and/or electromechanical actuators that typically utilize a ball-screw mechanism.

The vehicle depicted in FIG. 1 may also include one or more sensors for detecting various parameters. For example, a sensor may be a forward looking sensor such as a visual or infrared camera or detector used to monitor objects and markings located in front of the vehicle such as lane markings, approaching vehicles and objects, and/or obstructions. Sensors may also be mounted inside of a vehicle to monitor the movement and/or physical parameters of one or more occupants located within the vehicle. In one such embodiment, the one or more sensors located within the vehicle may include, but are not limited to, a camera, a sensor configured to monitor a physiological parameter of a vehicle occupant (e.g. a heart rate monitor, a galvanic skin response sensor, and oxygenation sensor, a carbon dioxide sensor, etc.), one or more accelerometers, inertia monitoring units, gyroscopes, and/or any other appropriate sensor.

In addition to the various sensors, the vehicle may also include one or more occupant inputs 10, such as a button, a dial, touchpad, or other appropriate input device. The input may be used by the occupant to input information to a controller of the vehicle and/or the suspension system. For example, as detailed further below, the occupant may use the indicator to inform the controller that they are experiencing some degree of motion sickness.

As also illustrated in FIG. 1, in some embodiments, an active suspension 4 may be combined with an air suspension 18 in series or in parallel with the active suspension system between the vehicle wheels and vehicle body. In some instances, the active suspension and air suspension may operate cooperatively to mitigate low frequency content, from the road, being transmitted to the sprung mass of the vehicle. For example, a control loop can be closed around accelerometers on the body of the vehicle, wherein the active suspension may extend the wheels while the air suspension fills (increasing ride height), and at other times the active suspension may retract the wheels while the air suspension deflates (reducing ride height). Height may be dynamically increased or decreased to keep the body level. Additionally, or alternatively, other motion sickness reducing control strategies, as described herein, may also be employed. Depending on the embodiment, the air suspension and active suspension may operate independently at the front and rear axle and/or independently at each wheel. In some embodiments, the air suspension may be combined with or substituted for the active suspension units described herein.

It should be understood that the systems and features described in relation to the above noted vehicle may be used with any of the other systems and methods described herein either individually or in combination as the disclosure is not so limited.

Figure 2:
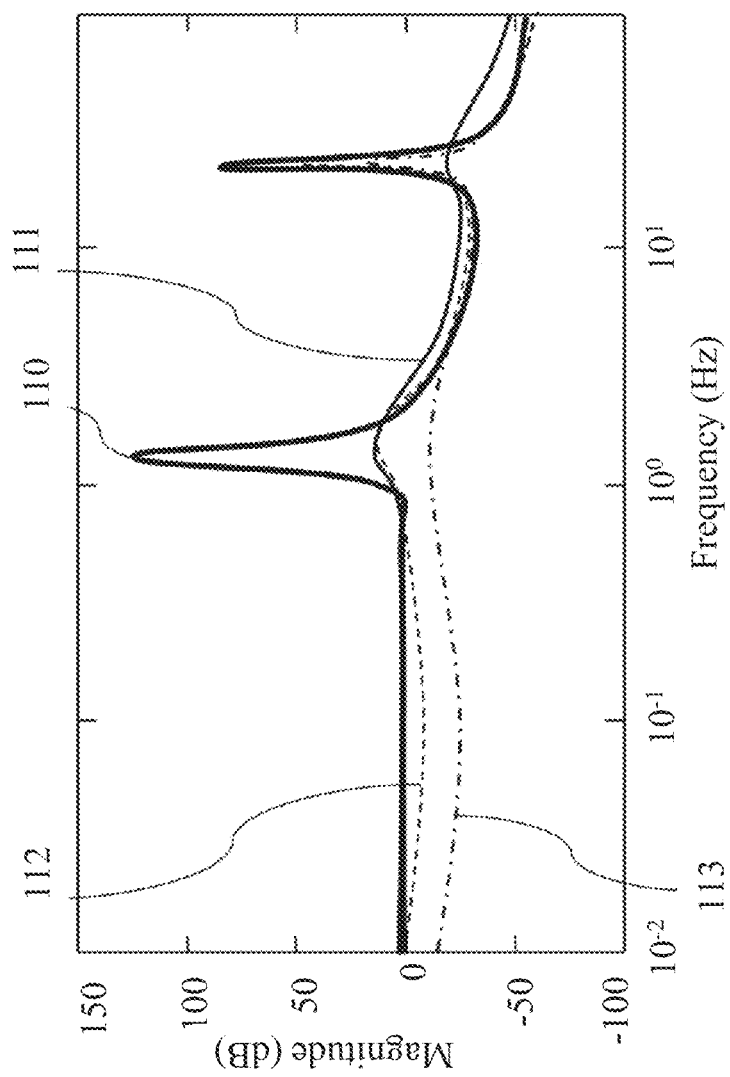
FIG. 2 is a transmissibility plot showing the ratio of vehicle body (sprung mass) acceleration and road vertical acceleration normal to the road $\ddot{Z}_b/\ddot{Z}_r$ as a function of frequency.

During operation, the wheels of a vehicle in contact with a road surface may induce vehicle body motion through their interactions with the road surface. FIG. 2 is a chart illustrating an example of transmissibility of disturbances from the road to the vehicle body (sprung mass). The curves present the magnitude of disturbances transmitted to the vehicle body versus the frequency of the induced motion where transmissibility is the ratio between vertical acceleration of the road as seen by the wheels ($\ddot{Z}_r$) and the acceleration of the vehicle body ($\ddot{Z}_b$). Curve 110 is a plot of transmissibility v. frequency for an undamped suspension system. Curve 111 represents an example of the transmissibility of an active suspension system of a vehicle with a driver. In this case, the suspension system is tuned to provide an acceptable balance between passenger comfort and road feel for the driver. In the case of an autonomous vehicle, in some embodiments road feel may no longer an important consideration. Therefore, the active suspension system of such an autonomous vehicle may be tuned to reduce low frequency transmissibility, such as for example, in a range of frequencies where motion sickness may occur to a greater degree, than in the conventionally driven vehicle of curve 111. However, in some embodiments, suppressing low frequency transmissibility may result in degradation of road feel and increased energy consumption by the active suspension system as well as increased transmissibility at certain higher frequencies. Two such embodiments are illustrated by curves 112 and 113 which illustrate examples of the transmissibility of an autonomous vehicle equipped with an active suspension system where the motion at the lower frequencies are mitigated compared to the driven vehicle (curve 111). Therefore depending on the embodiment, an autonomous vehicle, including an active suspension system, may be operated such that it reduces transmission of movements to at least a portion of a vehicle within a frequency range associated with motion sickness or other condition and may tolerate increase transmission of movements to the portion of the vehicle within a different frequency range outside of the targeted frequency range. For example, in the depicted embodiment, the curves associated with the autonomous vehicles show reduced transmission of motion to the vehicle body between about 0.1 Hz and 12 Hz and regions of increased transmission of frequencies above 12 Hz. Of course these are simply exemplary ranges and other frequency ranges both larger and smaller than those shown in the figures may also be used.

It should be understood that a suspension system may be operated in any appropriate fashion to provide a desired kinematic characteristic to produce a desired reduction of motion within various frequency ranges. For example, during at least one mode of operation a suspension system may be operated to further reduce motion transmitted to a portion of a vehicle as compared to another mode of operation within a frequency range equal to or between 0.05 Hz and 10 Hz, or any sub-portion thereof as described elsewhere within this disclosure. Of course the suspension system may also be operated so as to further decrease transmission motion within frequency ranges both higher and lower than those noted above as the disclosure is not so limited.

While the above embodiment is described primarily for use with autonomous vehicles, embodiments in which a conventionally driven vehicle including a suspension system is operated to reduce movements transmitted to a portion of the vehicle within a frequency range associated with motion sickness may also be implemented as the disclosure is not so limited.

Figure 3:
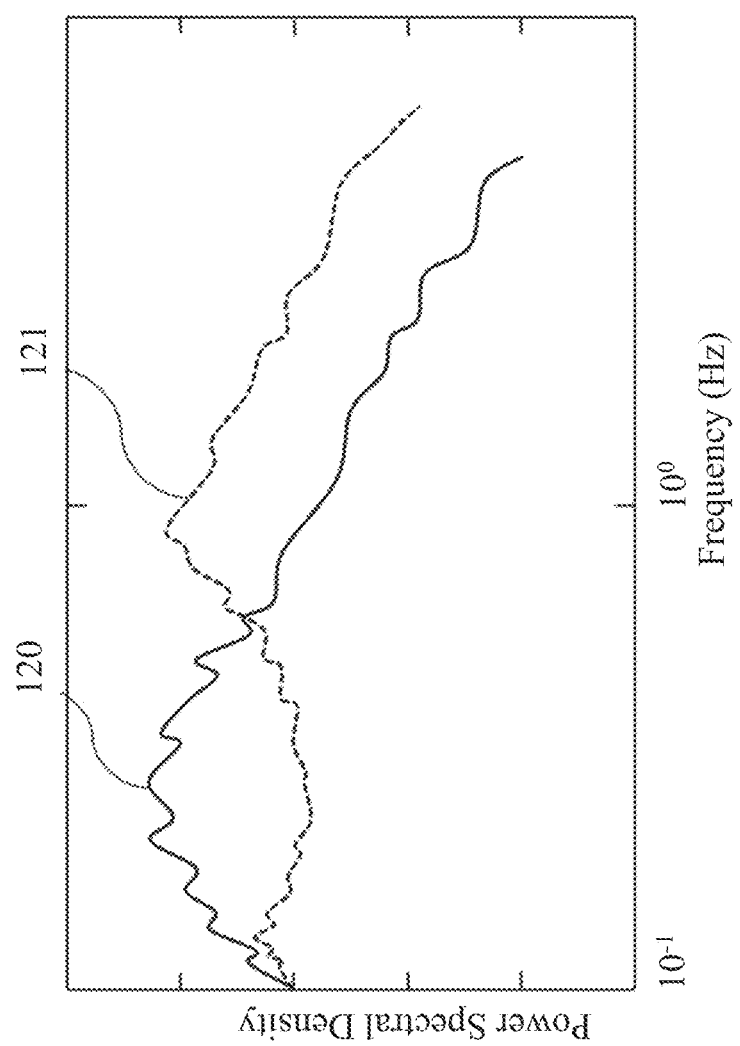
FIG. 3 is a graph of power spectrum for a vehicle body (sprung mass) as a function of frequency.

FIG. 3 illustrates the distribution of power spectral density (PSD) of oscillations transmitted to a vehicle body as a function of frequency. Curve 120 illustrates an example of PSD distribution for a vehicle with an active suspension system tuned for being driven by a person. Curve 121 shows an example of PSD distribution of oscillations transmitted to the vehicle body for an autonomous car, and/or a conventionally driven vehicle being driven in the mode intended to reduce motion sickness, where PSD in the motion sickness band is suppressed by the active suspension system. However, as compared to the conventionally driven vehicle, the PSD distribution for a vehicle being operated in a mode to reduce motion sickness may include an increase in transmitted energy at higher frequencies outside of a desired range for reducing motion sickness.

As noted previously, in some embodiments, a vehicle and/or suspension controller may be configured to accept one or more types of data such as one or more of vehicle acceleration, velocity and displacement in one or more directions as well as vehicle heave, roll and pitch from one or more sensors. Additionally, in some instances it may be beneficial for a controller to take into account physiological parameters and/or movements of a vehicle occupant during operation. Therefore, in one embodiment, a controller may receive data about, for example, the movements of the head and/or torso as well as various physical parameters of one or more occupants. A controller may also receive information from one or more occupants indicative of their identity and/or comfort level through an input device such as a dial, button, touch pad, or similar type of input to permit an occupant to directly input information to the controller that may be used to in determining how to control a suspension system of the vehicle. As described further below, the controller may also accept location information from a global positioning system (GPS) or other location based device to determine a location of the vehicle. This information may be used to identify locations where motion sickness may be at an increased likelihood of occurring. Using this information, the vehicle may either be rerouted around these locations and/or the controller may operate the suspension system in a mode intended to reduce motion sickness while the vehicle is located in these areas.

Based at least partially on one or more of the above noted input sources, a vehicle and/or suspension controller, may identify a situation and/or a pattern of road disturbances and/or characteristics that may lead to occupant discomfort or distress, such as for example, motion sickness. The controller may keep a record of their occurrence over a period of time. For example, the controller may be programmed to determine if situations and/or vehicle disturbances, such as acceleration in one or more directions within certain frequency ranges may induce motion sickness in the vehicle's occupants. If the controller determines that such events have been occurring over a long enough period where motion sickness or another malady is imminent or likely, the controller may alter various operational parameters to forestall and/or reduce the likelihood and/or the severity of the malady.

Figure 4:
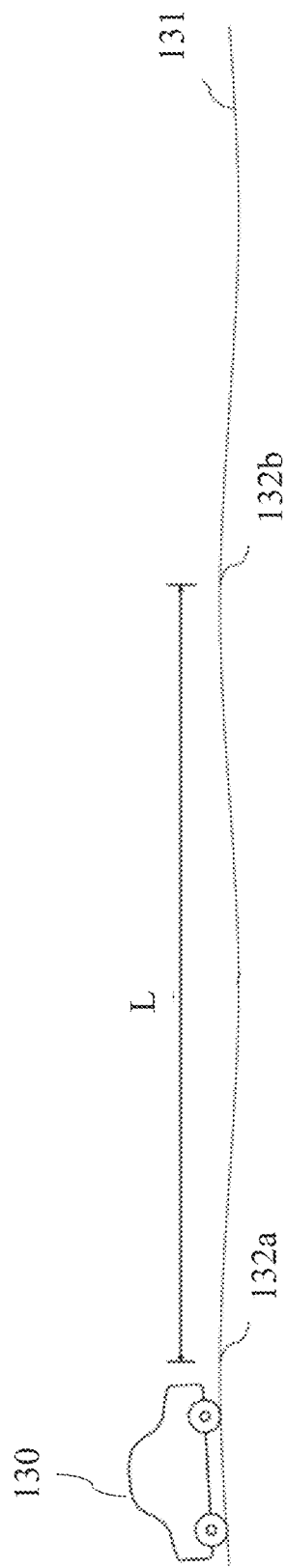
FIG. 4 is a schematic representation of an undulation in a road surface with a wavelength L.

FIG. 4 illustrates one possible embodiment of a vehicle controller that receives information from one or more sensors to determine whether or not an event associated with an increased likelihood of motion sickness is present. In one such situation, a road surface may include regular height variations, such as expansion joints or concrete slab boundaries on a highway or bridge, which may impart a suspension perturbation at a specific distance period while the vehicle is driven over these driving surfaces. This motion can be detected using sensors such as accelerometers. For example, in the figure, a vehicle 130 is travelling along a road surface 131 that has peaks at 133a and 133b that are a distance L apart. If the vehicle 30 is travelling at a speed of 40 miles/hour and the distance L is 147 feet, the vehicle will travel from peak 32a to peak 32b in 2.5 seconds. If such peaks reoccur along the surface at a regular interval of L feet and the vehicle maintains a speed of 40 miles/hour, a vertical acceleration will be imparted to the vehicle at a frequency of approximately 0.4 Hz. This frequency is typically recognized as being within a frequency band that can cause motion sickness.

In the above embodiment, if the detected vehicle perturbations from the associated peaks continue for more than a threshold time such as 1 minute, 3 minutes, 5 minutes, or 10 minutes a controller of the vehicle and/or suspension system may command the vehicle and/or suspension system to take an action to either reduce or alter the applied motion. For example, with the same road surface topography noted above, if an autonomous, or semi-autonomous, vehicle were to increase its speed to 65 miles/hour, the road induced excitation would occur at a frequency of approximately 0.65 Hz which is typically recognized to be outside the frequency band that can cause motion sickness. Additionally, in some embodiments, the controller may use an active suspension or other actuators associated with a portion of the vehicle to induce motion in the vehicle in a direction other than in the direction of travel. The induced motions may be used to mask the effects of motion that occur prior to, simultaneously with or subsequent to the induced motions. For example, the controller may be programmed to alter the total movement experienced by a vehicle occupant. This may, for example, be achieved by superimposing active suspension induced disturbances with the road induced disturbances. In the case of the vehicle depicted in FIG. 3 travelling at a speed of 40 miles/hour, the motion frequency experienced by a vehicle occupant may be increased by inducing one or more additional displacement peaks that occur when the vehicle is between expected road disturbances at points 32a and 32b. Depending on the number of suspension induced displacement peaks applied by the suspension system between sequential road displacements, this may lead to a factor of 2, 3, 4, 5, 10, or any other appropriate factor increase in the motion frequencies experienced by a vehicle occupant. Therefore, as detailed further below, a controller may either: alter a speed of the vehicle to change the induced motion from a first frequency range associated with motion sickness to a second frequency range not associated with associated with motion sickness; use a suspension system of the vehicle to induce motion in the vehicle to mask the road induced disturbances; alter a kinematic characteristic of the suspension system to reduce motion within the detected frequency range; or a combination of the foregoing.

Elaborating on the above noted embodiment regarding masking the road disturbances transmitted to a vehicle body using an active suspension. In one such embodiment, the active suspension system of a vehicle may be used to alter the frequency and/or phase of vehicle motion in order to reduce the likelihood of motion sickness. For example, the active suspension system may induce motion in the vehicle body in addition to the road induced movement transmitted to the vehicle body to change a frequency of the overall movement experienced by a vehicle occupant. These induced motions by the active suspension system may include pitch, roll, and heave motions of the vehicle body. Further, in some embodiments, the overall resulting vehicle motion may be at a higher frequency less likely to cause motion sickness. Depending on the embodiment, the frequencies and/or amplitudes of the motion induced in the vehicle by the suspension system may be selected to be largely imperceptible to the occupants. In another embodiment, the active suspension system may be used to intentionally vary the pitch of the vehicle, for example, during stop and go driving to alter the disturbance frequencies introduced by the braking process. Of course, it should be understood that an active suspension system may be used to apply multiple types of motion to a vehicle body including one or more of the above noted pitch, roll, and/or heave motions to mask a particular type of motion being transmitted to a vehicle body from an associated road surface.

Figure 5:
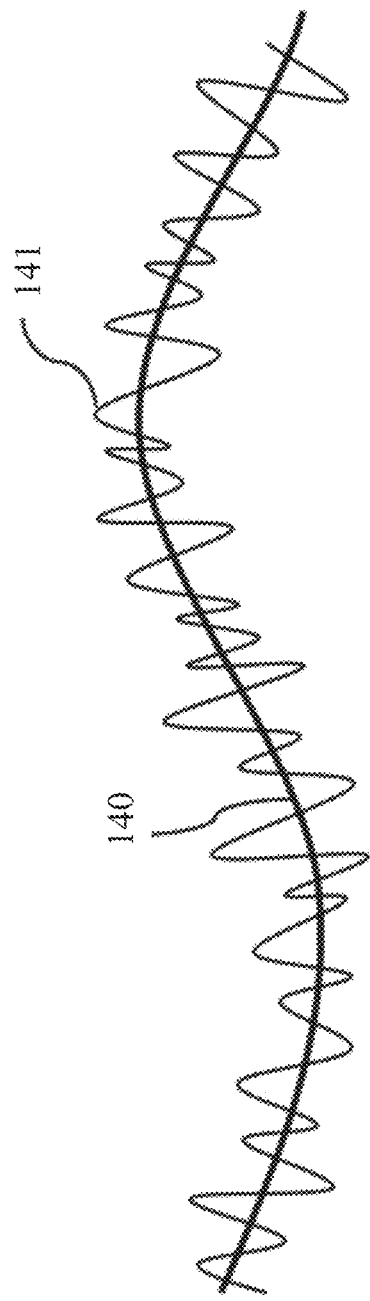
FIG. 5 is a schematic representation of masking low frequency accelerations by inducing higher frequency accelerations.

In addition to the above, masking a road induced disturbance by altering a frequency of the total movement applied to a vehicle body may be more effective if a magnitude of a phase offset suspension induced disturbance is comparable to a magnitude of a road induced disturbance. Of course, if it is undesirable (due to energy consumption limitations) or not possible (due to the lack of available actuator travel), a masking disturbance applied to a vehicle by an active suspension system may be smaller in amplitude than the road induced disturbance. FIG. 5 illustrates an embodiment of a road induced disturbance 140 superimposed with, i.e. masked by, a plurality of suspension induced disturbances 141. As shown in the figure, the road induced disturbance is a lower frequency disturbance than the superimposed higher frequency disturbances implied by the suspension system. Additionally, in this particular embodiment, the disturbances applied to the vehicle body using the suspension system have an amplitude that is smaller than the road induced disturbances.

While the above embodiment describes the use of suspension system induced disturbances with magnitudes that are equal to or less than a corresponding road induced disturbance, embodiments in which suspension system induced disturbances have magnitudes greater than a corresponding road induced disturbance are also contemplated. For example, depending on the various operating parameters noted above, a suspension system induced disturbance to the vehicle body may have a magnitude that is greater than or equal to about 10%, 30%, 50%, 80%, 100%, or any other appropriate percentage magnitude of a road induced disturbance to the vehicle body. Correspondingly, the suspension system induced disturbance may have a magnitude that is less than or equal to about 150%, 120%, 100%, 80%, 50%, or any other appropriate percentage magnitude of the road induced disturbance. Combinations of the above ranges are contemplated including, for example, a suspension induced disturbance with a magnitude that is between or equal to about 50% and 150% of a road induced disturbance to a vehicle body within a predetermined frequency range.

In order to reduce the amount of energy consumed by inducing the above noted disturbances using an active suspension system, in some embodiments, a controller may utilize such masking methods when it is determined that an undesirable condition, such as motion sickness, is likely due to the contributing conditions have been present for more than a threshold time period. The masking methods may also be instituted when at least one occupant of the vehicle indicates a discomfort level to the controller using an appropriate input that is greater than or equal to a threshold level of discomfort. The controller may also determine a discomfort level of the one or more occupants using one more sensors as described further below.

Figure 6:
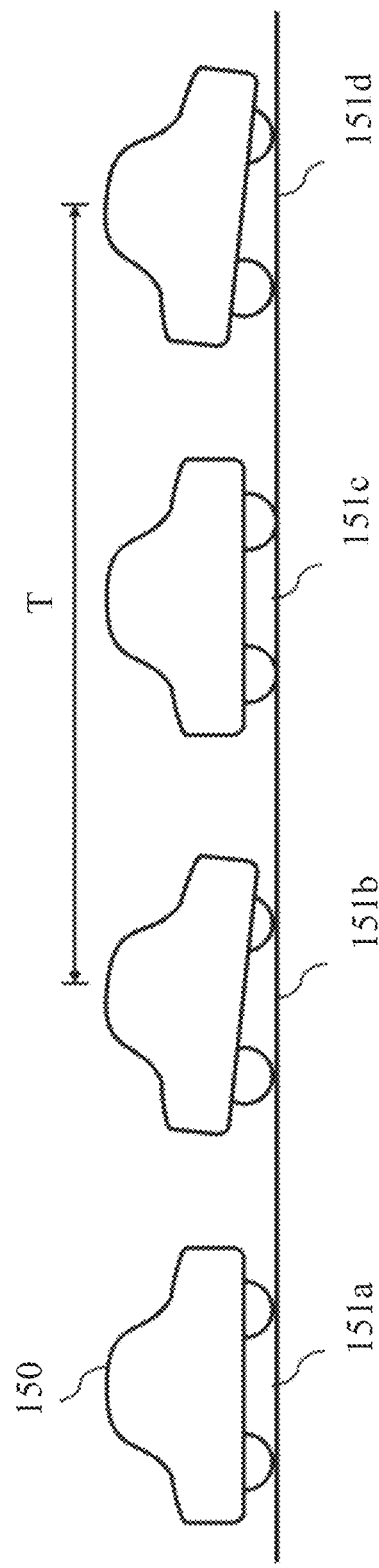
FIG. 6 is a schematic illustrating variable pitch induced by stop-and-go driving.

FIG. 6 illustrates a vehicle 150 traveling in stop and go traffic. In positions 151a and 151c the vehicle is travelling forward, while in positions 151b and 151d the vehicle is braking. Typically, at each braking event the vehicle pitches forward by an amount that is determined by the rate of deceleration. If due to traffic conditions, for example, braking events occur every 20 feet and the vehicle travels at an average speed of five miles per hour, the frequency of occurrence of braking events will be 0.36 Hz which is in a frequency range that is typically considered to induce motion sickness. In embodiments, a controller may be used to recognize, based on data from one or more sensors, a pattern of braking induced disturbance that occurs, for example, in the range of 0.05 Hz to 1 Hz, 0.05 Hz to 0.5 Hz, 0.08 Hz to 0.4 Hz, or any other appropriate frequency range. If this pattern continues for a threshold time period and/or if information is received from one or more occupants of the vehicle indicating that one or more persons are suffering from motion sickness, the controller may take corrective action. For example, a controller may brake more frequently, even if not necessary due to traffic conditions, in order to move the braking frequency beyond the range that may cause discomfort such as, for example, motion sickness. The controller may also operate an active suspension system of the vehicle, to reduce, or eliminate, the detected pitch motion of the vehicle body and/or a portion of the vehicle associated with one or more vehicle occupants.

While the above noted embodiment describes reducing or eliminating the pitch associated with each braking event, in some embodiments, in order to conserve energy, it may be necessary to operate the active suspension system of the vehicle to reduce, or eliminate, the pitch associated with a portion of the braking events. For example, if the pitch in two out of three braking events is eliminated by the active suspension system, the frequency of pitch events may be moved to a frequency range outside of a motion sickness inducing frequency range, while the number of braking events remains the same.

Figure 7:
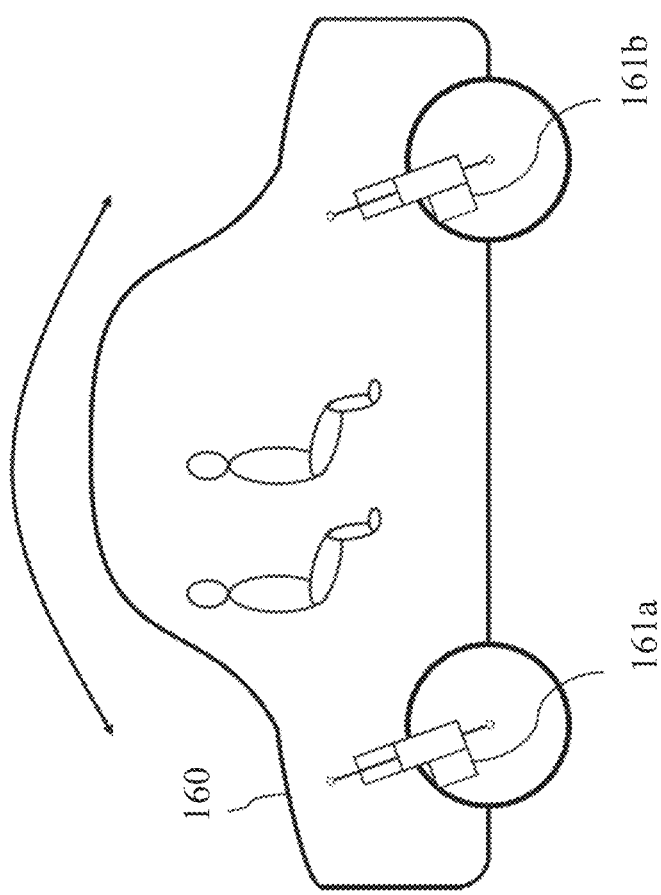
FIG. 7 is a schematic illustrating the use of an active suspension system to mitigate changes of pitch such as by stop and go driving.

In a somewhat similar embodiment, and as shown in FIG. 7, a vehicle 160, with an active suspension system, may undergo pitch motions during any number of different situations. However, regardless of the particular situation giving rise to a pitch motion of a vehicle, in typical vehicles the front row occupants may be closer to a center of rotation in a pitch motion than occupants located in a center or back row seat. Therefore, in some embodiments, a vehicle and/or active suspension controller may operate the active suspension system, which include actuators 161a and 161b, to reduce, or eliminate, the vertical motion experienced by the rear seat occupants when the vehicle pitches either during normal operation, and/or when the pitch motions are located within a frequency range associated with motion sickness and the vehicle is being operated in a mode to reduce motion sickness.

In some embodiments, a vehicle may be equipped with multiple suspension systems associated with different portions of a vehicle. For example, a first suspension system may be interposed between the wheels of a vehicle and the vehicle chassis or undercarriage. A second suspension system may be interposed between the chassis or undercarriage and the passenger compartment. A third suspension system may then be interposed between the passenger compartment and one or more structures within the passenger compartment such as a vehicle occupant seat and/or a work surface such as a table or a desk.

When multiple suspension systems are used in a vehicle, one or more of these suspension systems may be active, semi-active, passive, or a combination of the above. Further, each of the suspension systems may work independently or in coordination with one or more of the other systems. Each of the suspension systems may share one or more sensors or may receive information from the same or different sources. For example, the suspension systems may be controlled by a central controller they are in electrical communication with and/or they may be in electrical communication with individual controllers associated with each suspension system. Additionally, each actuator and/or damper within the suspension systems may either be in electrical communication with a central controller of that suspension system and/or they may be in electrical communication with a plurality of distributed controllers individually associated with each actuator as the disclosure is not limited in this fashion.

In embodiments where one or more active suspension systems are used in a vehicle, the one or more active suspension systems may be used to introduce desirable motions or suppress certain undesirable motions in one or more portions of the vehicle relative other portions of the vehicle and/or to an absolute reference frame. For example, one or more seats within a vehicle may be moved in a manner that would promote sleep and/or increased drowsiness in a baby or an infant. This motion may be at a predetermined frequency and/or amplitude, selected by another individual and/or automatically by a controller. In another embodiment, certain seats that are occupied may be controlled to reduce motion associated with certain frequency ranges to a greater degree than other seats that are not occupied. Alternatively, one or more seats within a vehicle may be controlled to suppress certain frequencies to a greater degree than other seats in the passenger compartment. Such an embodiment may be advantageous if: one or more occupants within a vehicle are more sensitive to motion sickness than other occupants located within the same vehicle; one or more occupants are in an orientation that is more likely to induce motion sickness; or an occupant has a particular ailment such as a back problem. Seats occupied by such individuals may be determined by using sensors, such as facial recognition cameras, or by using devices that enable passengers in a vehicle to provide data to a controller. Benefits associated with individually controlling various structures in a vehicle may include conserving energy, enhancing the overall comfort of all passengers, and avoiding unnecessary wear and tear on actuators.

In embodiments, where multiple suspension systems are used as described above, the various suspension systems may either be used independently and/or in conjunction with one another. For example, one or more seat suspension systems may be used independently or in conjunction with a vehicle active suspension system associated with the vehicle body and wheels. In one such embodiment, the different suspension systems may be used to reduce transmitted motion within different frequency ranges. As noted above, these different suspension systems may be associated with various different portions of a vehicle. However, in one embodiment, a seat suspension system may be used to reduce motions within a first frequency range transmitted to an occupant in the seat while an associated vehicle active suspension system is used to mitigate motion in a different second frequency range. These different frequency ranges may correspond to any appropriate ranges of frequency as the disclosure is not so limited. However, embodiments where a lower mass portion of the vehicle is damped to a greater degree at lower frequencies and the vehicle body is damped at higher frequencies to a greater may require less energy, i.e. reduce overall energy consumption. This may be due to low frequency motions requiring more energy to damp per unit mass. Therefore, damping the heavier vehicle body at higher frequencies and the lighter seat at lower frequencies may reduce energy consumption. In one such embodiment, a seat and/or passenger compartment suspension system, or other suspension system associated with a portion of a vehicle, may be used to primarily mitigate low frequency oscillations between about 0.05 Hz and 0.5 Hz, or 0.05 Hz and 1.0 Hz, while the active suspension system is used to primarily isolate the vehicle from disturbances with frequency greater than those mitigated by the seat suspension system. Of course, while a specific frequency ranges are noted above, the various suspension systems associated with portions of a vehicle may be operated in any number of different frequency ranges including ranges both greater than and less than those noted above.

As noted above, certain portions of a vehicle may be controlled separately from the remainder of the vehicle body. For example, seats may be controlled to eliminate frequencies in a particular range, such as 0.05 to 1 Hz, while the remainder of the vehicle body may be controlled at frequencies greater than 1 Hz. However, under certain circumstances, this may result in large amplitude relative motion between different structures inside the vehicle compartment which may either be disturbing and/or lead to unwanted contact between a structure and an occupant of the vehicle. Therefore, in some embodiments the motion of different structures within a passenger compartment, or other portion of a vehicle, may be controlled in different frequency ranges and the relative motion between those structures may be limited to be less than or equal to a relative movement threshold. This may either be controlled through active feedback related to the structures' movements and positions, or in some embodiments, mechanical constraints may be used restrict the relative motion in at least one direction between two or more structures. For example, if the passenger compartment is controlled separately from the vehicle chassis, mechanical constraints may be added to restrict relative lateral motion between the two structures.

Figure 8:
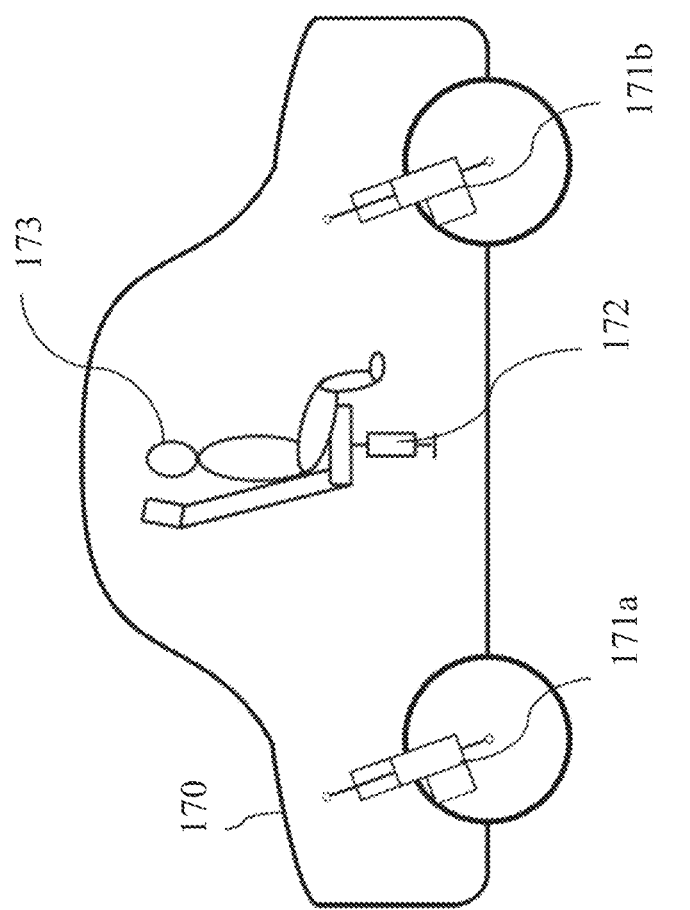
FIG. 8 is a schematic representation of an active suspension system used to mitigate low frequency oscillations of a first platform (such as a passenger seat) that is supported by a second platform (such as the sprung mass of a vehicle), where the high frequency motions of the second platform are shown to be mitigated by an active suspension system.
Figure 9:
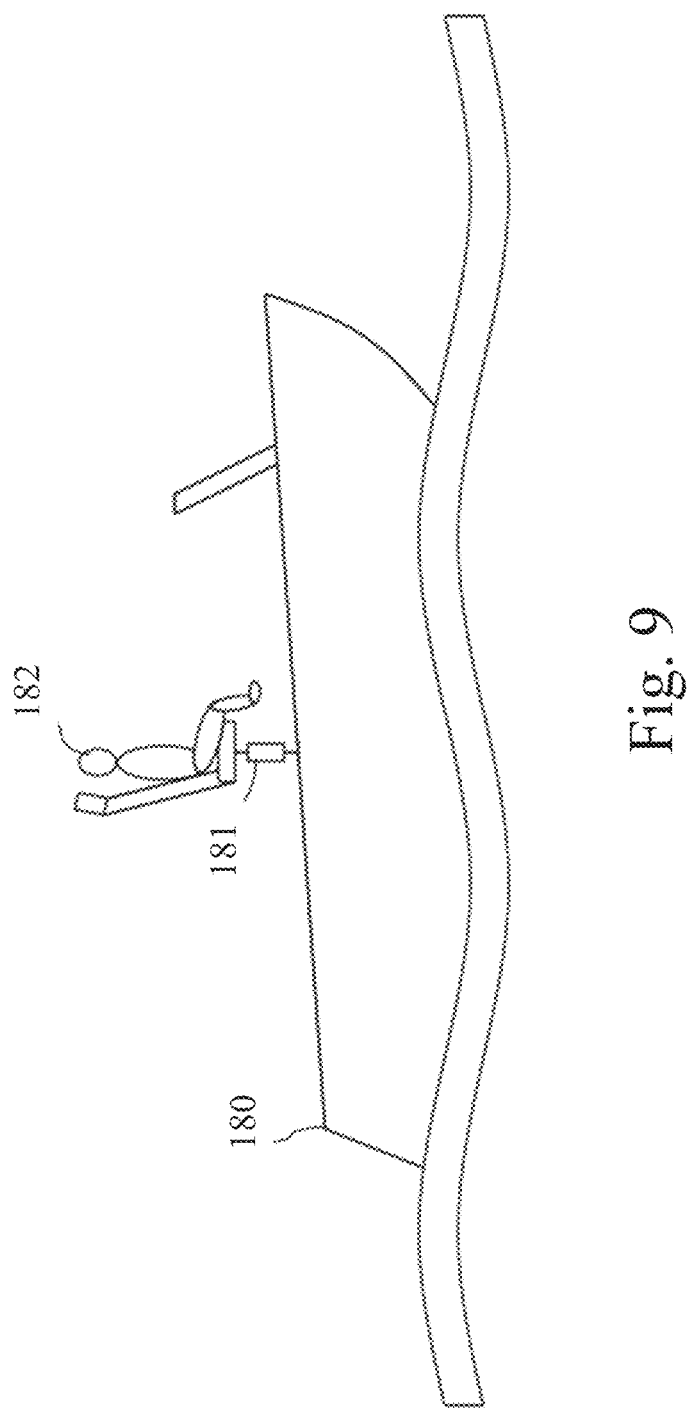
FIG. 9 is a schematic representation of an active suspension actuator in a watercraft to mitigate oscillations from reaching an occupant.

While a seat active suspension system has been described above for use in a vehicle such as an automobile, a seat active suspension system may also be used in other types of vehicles including, for example, a boat or other watercraft to isolate passengers from oscillations within a frequency range associated motion sickness. Therefore, as shown in more detail below in the figures, in some embodiments, a seat suspension system may be used in a boat or other watercraft whenever the watercraft is subjected to certain event patterns which may cause motion sickness. In other embodiments, the seat active suspension system may be operated when requested by one or more passengers. The seat active suspension system may have one degree of freedom (such as, for example, vertical control), or multiple degrees of freedom in order to create, pitch, roll, and/or heave motions in the associated seat. FIGS. 8-9 illustrate various embodiments of this concept.

FIG. 8 illustrates a vehicle 170 with an active suspension system that includes actuators 171a and 171b. The vehicle also includes a seat suspension system 172. In some embodiments, the seat suspension system may be used to damp out low frequency oscillations, or motions, transmitted to the vehicle body from being transmitted to a vehicle occupant 173. As noted above, this configuration may result in energy savings because a relatively smaller mass needs to be actively controlled over long periods than if the active suspension is used to control low frequency oscillations of the entire vehicle. However, embodiments in which the active suspension system associated with the wheels and vehicle body is operated to significantly reduce motion in the same frequency ranges are also contemplated as the disclosure is not so limited FIG. 9 illustrates a watercraft 180 where a seat suspension system 181 reduces the magnitude of oscillations or other motions that reach occupant 182 seated in the associated seat. In some embodiments the actuator may be used to mitigate primarily oscillations and movements within the frequency range associated with motion sickness. Depending on the particular embodiment, the seat suspension system may be used to mitigate motion within a frequency range associated with motion sickness when requested by a vehicle occupant. Additionally, the suspension system may be used to mitigate motion in the motion sickness frequency range when an event pattern is recognized by a vehicle and/or suspension system controller that is associated with an increased likelihood of motion sickness as described further below.

In one embodiment, a controller of an autonomous vehicle and/or an active suspension system may make route selections based on the susceptibility to motion sickness of one or more occupants in the vehicle and/or information about road characteristics and travel characteristics of various routes the vehicle may travel on. For example, the controller of an autonomous vehicle may select one road over another because the combination of road surface conditions and possible speed of travel of one road may be less likely to cause motion sickness. Additionally, as detailed further below, particular locations may be associated with an increased likeliness of one or more occupants of the vehicle experiencing motion sickness. Consequently, when a vehicle is located in these areas, the controller of the vehicle and/or active suspension system may enact any of the motion sickness mitigation techniques described herein to reduce a likelihood of motion sickness for the vehicle occupants. Specific embodiments of such a system and methods are described further below.

Under certain circumstances the need for corrective action by a vehicle and/or suspension controller may be minimized if the vehicle controller is used to avoid the production of undesirable disturbances when performing certain vehicular functions. For example, in stop-and-go traffic, instead of repeatedly employing the brakes to stop the vehicle at regular intervals, the throttle, transmission and ranging systems may be used to accelerate and decelerate the vehicle such that optimal spacing may be maintained with other vehicles and the use of the brakes can be minimized. Additionally, during turns, the vehicle controller may operate the steering and engine throttle to optimally match available turn radius with vehicle speed so as to minimize the production of lateral disturbances in a frequency range associated with an increased likelihood of motion sickness. Route planning systems may utilize forward looking cameras, GPS systems, and road surface databases so as to select the best GPS route and/or lane to minimize disturbances in the motion sickness frequency range. This may at least partially be based on remotely stored data transmitted to the vehicle, such as a cloud based server transmitting information regarding a particular location to a vehicle traveling in that location. While the operation of a vehicle and suspension system to reduce lateral movements of a vehicle has been described above, it should be understood that a speed, turning radius, and one or more suspension systems of a vehicle may be controlled to provide a desired amount of motion reduction in any direction including but not limited to pitch, roll, heave, lateral, and axial direction. Additionally, in instances where an active suspension system is used, the active suspension system may be controlled to provide a desired vehicle posture for various maneuvers performed in an autonomous driving mode.

In one embodiment, it may be desirable for a vehicle and/or suspension system controller to determine a motion sickness mitigation strategy prior to encountering different situations along a planned driving route. In such an embodiment, expected event patterns may be predicted by a controller for a planned route based on, for example, one or more of data collected by look-ahead sensors and/or previously collected data related to the desired route. While any appropriate type of look-ahead sensor may be used to sense information from a driving surface located ahead of a vehicle in the direction of travel, appropriate sensors include, but are not limited to, optical cameras, infrared cameras, laser range finders, radar, LIDAR, or any other appropriate sensor. When using previously collected road data, a vehicle may either recall information collected and stored by the same vehicle on a previous trip, receive information wirelessly transmitted from other vehicles, and/or receive information from a remotely located computing device or server that stores road information sensed by other vehicles during prior trips. For example, vehicles that detect motions within a frequency range associated with motion sickness may transmit the experienced events and locations to a central server or computing device where they are stored in a database for subsequent transmission to vehicles either planning to travel, or are traveling, through those locations.

Using the information from the look ahead sensors and/or previously recorded information, a vehicle controller may identify locations along a planned route where conditions may result in an increased likeliness of motion sickness. Corrective actions may then be planned and implemented when the vehicle is located in the identified locations to avoid exposing occupants to disturbances that may cause an increased likelihood of motion sickness. Additionally, using the look ahead sensors the vehicle may scan the surroundings to create a map of vehicle surroundings and objects. Based on height and frequency thresholds set to classify road conditions needing correction, the vehicle will have predictive knowledge of road characteristics before the conditions are experienced. Using an updated 3D map, the vehicle may determine an appropriate path of travel through obstacles, whether stationary or moving, and the amount of energy needed for various maneuvers.

In addition to modifying the operation of a suspension system, motion sickness avoidance algorithms of a vehicle may either suggest a route modification to a conventionally driven vehicle or modify a planned driving route for an autonomous or semi-autonomous vehicle using location based input from a central database or location and GPS-based road data. Such algorithms may alter the chosen route to reach a destination in order to avoid motion sickness inducing conditions. Such conditions may be based on known motion sickness inducing roads or road segments, present traffic conditions, and/or any other factor that may contribute to motion sickness. However, in some embodiments, motion sickness avoidance algorithms, including route planning considerations, may be discontinued based on occupant request and/or preference.

In embodiments, data from one or more sensors indicative of operational conditions that may induce discomfort, such a motion sickness, to a vehicle occupant are stored for subsequent use or recall. This data may be stored either locally on a vehicle or remotely on a remotely located server or database. As detailed below, this data may be used to identify future occurrences of certain patterns of operational parameters that are precursors to or indicative of occupant discomfort, such as motion sickness. This recorded data may then be used as a predictive tool, for example for a specific occupant, specific road segment, or specific vehicle to identify events and/or locations that are likely to induce vehicle occupant discomfort. This data may also be shared, for example, with other vehicles or uploaded to a central repository such as a database or server the vehicle is in communication with either through a wireless or wired connection when the vehicle is connected to an appropriate internet portal. Depending on the application, this data may be sent with or without demographic information about vehicle occupants. The data may then be analyzed centrally to identify patterns of operational parameters that can be used as templates for comparison with actual operating conditions to predict motion sickness or other vehicle related maladies that may be universal or specific to various roads or segments of the population. Specific non-limiting examples of patterns of movement that may be used as a template for predicting motion sickness are detailed further below.

In some embodiments, if vehicle sensors and/or available data indicate that, due to recently experienced motion patterns, a situation is likely that may cause discomfort (such as, for example, motion sickness), a vehicle and/or suspension controller may take preventive measures to mitigate the situation using any of the motion and/or motion sickness mitigation methods and systems described herein. Such information may then be shared, for example by using a wireless connection or the internet, with other vehicles and/or remotely located servers or databases. Therefore, a database may be developed from such shared information that can be accessed by vehicles to help mitigate such situations in the future. This database may include situational, operational, and/or geographic information. For example, in some embodiments, if vehicle sensors detect road conditions that are prone to cause passenger discomfort, for example motion sickness, an indication of such conditions may be communicated to one or more other vehicles and/or to a central database or server. This may allow other vehicles to compensate for or avoid discomfort causing road conditions before they are sensed by the vehicle. When a vehicle detects conditions that may cause passenger discomfort, an indication of severity may also be assigned to the detected pattern and may be communicated to other vehicles or interested parties. Depending on the level of severity, the vehicle may either change the planned route or compensate for the road perturbations when the vehicle experiences them by, for example, changing speed and/or more aggressively isolating the vehicle body or structures within the vehicle in a particular frequency range that may, for example, cause motion sickness or be otherwise unpleasant for one or more vehicle occupants.

In certain applications, it may be desirable to record occupant input regarding situations experienced by a vehicle for different geographical conditions and/or locations. For instance, vehicle occupants may input information to a vehicle controller regarding specific geographical conditions and/or locations. Further, in some instances, it may be desirable for the occupant to input information to the controller regarding how the vehicle should behave in a particular location and/or condition. For example, the occupant can indicate where a particular construction route is occurring with the intention for the vehicle suspension to behave in a certain manner, such as with increased motion mitigation, while traveling through the area. Similar to the above embodiments, geographical locations, routes, and/or conditions identified to cause occupant discomfort may then be transmitted to other vehicles and/or a central database for subsequent use and/or storage. In one such embodiment, based on vehicle occupant feedback and road condition detection, a geographical location may be identified to cause heightened feelings of vehicle occupant discomfort such as, for example, motion sickness. This information may then be transmitted to one or more vehicles that will potentially travel along the route. The vehicle or occupants may decide to avoid such identified routes in an attempt to reduce vehicle occupant discomfort occurrence. Additionally, in another embodiment, based on the information obtained from a car's local database, a remote database, and/or transmitted from other vehicles, a controller of the vehicle may: recommend the most comfortable (i.e. smoothest) route; use information from a network accessible database with road roughness data combined with routing algorithms to give the route with the best ride possible within certain constraints such as for example, time, tolls, scenery, occupant requirements, etc; reduced power consumption; as well as any other desirable metric for controlling a vehicle. For example, an autonomous vehicle may use information from a database or previous trips to determine the locations of potholes or other impediments, and can plan a travel route that avoids these road features.

During vehicle motion, vehicle sensors may also classify road perturbations into categories that may be useful in aiding with the maintenance and upkeep of roads. Data about road profiles identified during vehicle motion can be transmitted to a central database or server where it is aggregated with information from multiple vehicles to produce a comprehensive mapping of road conditions associated with a particular location. The road conditions identified within this database, and/or information provided directly from individual vehicles, may then be provided to local governing agencies to keep updated road condition records. For example, the location and severity of potholes or road degradation may be identified and reported to local agencies in an attempt to make road maintenance and upkeep more efficient. Road conditions sensed by the various vehicle sensors may also include, but is not limited to weather related conditions such as, for example, snow and ice cover may be identified using information such as antilock brake system activations, cameras, and/or any other appropriate type of sensor or system. This information may again be supplied to a central server or database where it may be analyzed and/or shared. Mapping of the location of potholes and other road hazards may be performed as a service for various interested parties. In one such embodiment, the magnitudes and directions of disturbances input into the wheels and/or vehicle body of a vehicle relative to the nominal disturbance from a particular surface may be used to identify perturbations within a road surface including features such as potholes. Further, the magnitude of a particular disturbance at a given vehicle velocity may be used to determine the severity, i.e. size, of a particular feature. Again, this information may be combined with location information to at least partially control the operation of a suspension system and/or planning of a route. Also, this information may be uploaded to a central database and/or transmitted to other vehicles for subsequent use in planning routes and motion mitigation strategies.

Vehicle motion while traveling on a road typically occurs with six degrees of freedom. Therefore, in some embodiments, an active suspension system may be used to control the heave, pitch, and/or roll of a vehicle. However, in some embodiments, such as fully autonomous or partially autonomous vehicles, the propulsion, steering and/or other systems in a vehicle may be used to control motion in the fore-aft, yaw, and lateral directions as well in order to, for example, mitigate motion sickness. In addition, by changing the speed of a vehicle, it is possible to change the frequencies and/or magnitudes of road-induced disturbances, such as vertical disturbances due to spaced bumps or variations in a road surface, to which the vehicle body and/or occupants are exposed.

In some embodiments, one or more controllers in a vehicle, that is under partial or full autonomous control, may be used to control two or more of the vehicular systems noted above including, for example, the active suspension, propulsion systems (e.g. throttle), braking system, and/or steering systems to coordinate operation of the vehicle to events and/or patterns that may cause discomfort to an individual. Further, operation of these vehicle system may be used to alter a frequency, direction, and/or magnitude of forces and/or accelerations that the vehicle and/or occupants within the vehicle are exposed. This coordination among two or more such systems may be established for a single events, for an extended period, such as for example when it is determined that motion sickness is likely, and/or may be used throughout vehicle operation as the disclosure is not limited in this fashion. Additionally, while coordination amongst these vehicle systems to control motion of the vehicles and occupants has been described, embodiments in which these vehicle systems are controlled individually to mitigate these motions are also contemplated.

In one exemplary embodiment, one or more controllers in a partially or fully autonomous vehicle may be used to adjust the speed of a vehicle so as to reduce the centripetal acceleration to which a vehicle is exposed while traversing an upcoming curve so that the vehicle could be maintained at, for example, a desired posture such as roll angle, maximum roll angle, and/or maximum roll rate below a certain threshold value which may otherwise be beyond, for example, the power, energy, force and/or frequency response limitations of an associated active suspension system.

In another embodiment, one or more controllers in a vehicle may be used to determine a proper speed at which a vehicle should navigate a turn, or other maneuver, in the road so that the active suspension system may be able to maintain a vehicle at a desired positive, neutral, or negative roll angle throughout the turn while maintaining operation of the active suspension system within a desired threshold limit such as an energy threshold, a force threshold. In some embodiments, the coordination between two or more systems such as the active suspension, propulsion, and braking systems, may also be used to control vehicle pitch during braking by changing a frequency of braking events, vehicle speed, acceleration, deceleration, and other appropriate parameters. Additionally, when it is determined that one or more passengers are likely to suffer from motion sickness, or other discomfort, the above, or other mitigation techniques using one or more of the noted vehicle systems as described herein may be instituted.

Figure 37:
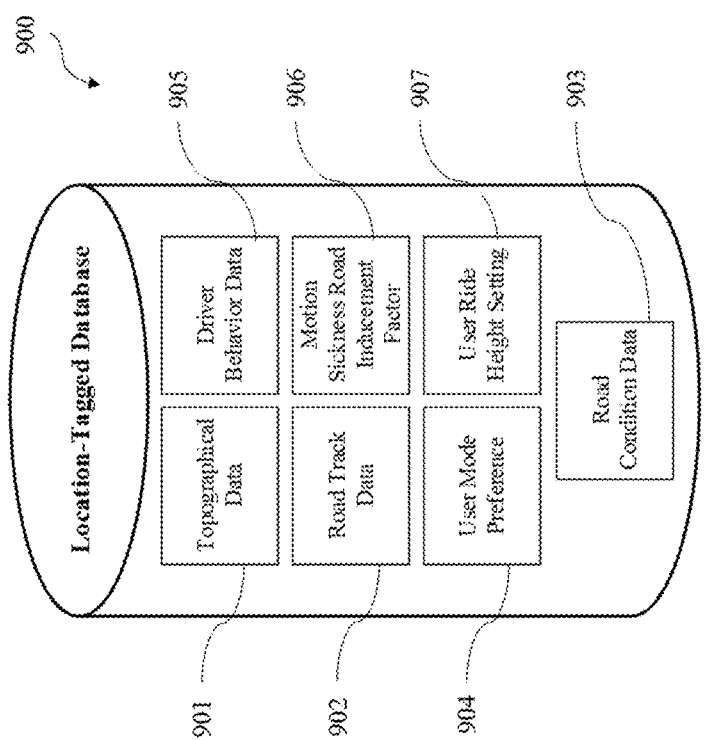
FIG. 37 illustrates an embodiment of a location tagged database that encompasses various road, vehicle, and user data.

FIG. 37 illustrates an embodiment of a location tagged database (LTD) 900 that may be used to aid navigation and operation of autonomous, semi-autonomous, and conventionally driven vehicles as previously described. Information in an LTD which may be associated with position along a road may include, for example, topographical data 901, road track data 902, road condition data 903, user mode preference information 904, driver behavior data 905, motion sickness inducement factor 906, and user selected height adjustment 907. Information in the LTD may be collected from various real-time sources, including vehicles traveling along a road and/or batch and/or archival sources.

In certain embodiments of an LTD, positioning data, such as may be obtained from, for example, a GPS receiver, may have insufficient resolution to permit reliable navigation. Therefore, the global positional data in the LTD may be correlated with, and augmented by, information about the relative position of features such as trees, telephone poles, bridges, buildings, sign posts, and/or details about the road being traveled, including, for example, the relative position of turns, changes in elevation, and surface roughness and/or anomalies.

Such local data sets may be used to generate patterns that may be stored in association with large scale or global coordinates that may have a lower level of granularity. These local patterns may then be used by vehicles to locate themselves more precisely with respect to the road than would be possible with lower granularity global positioning data.

This higher granularity local data may be compiled from information received from various sources such as vehicles traveling on the road, third party applications including but not limited to Google Street View, surveying companies, satellite imaging companies, and municipalities.

Figure 38:
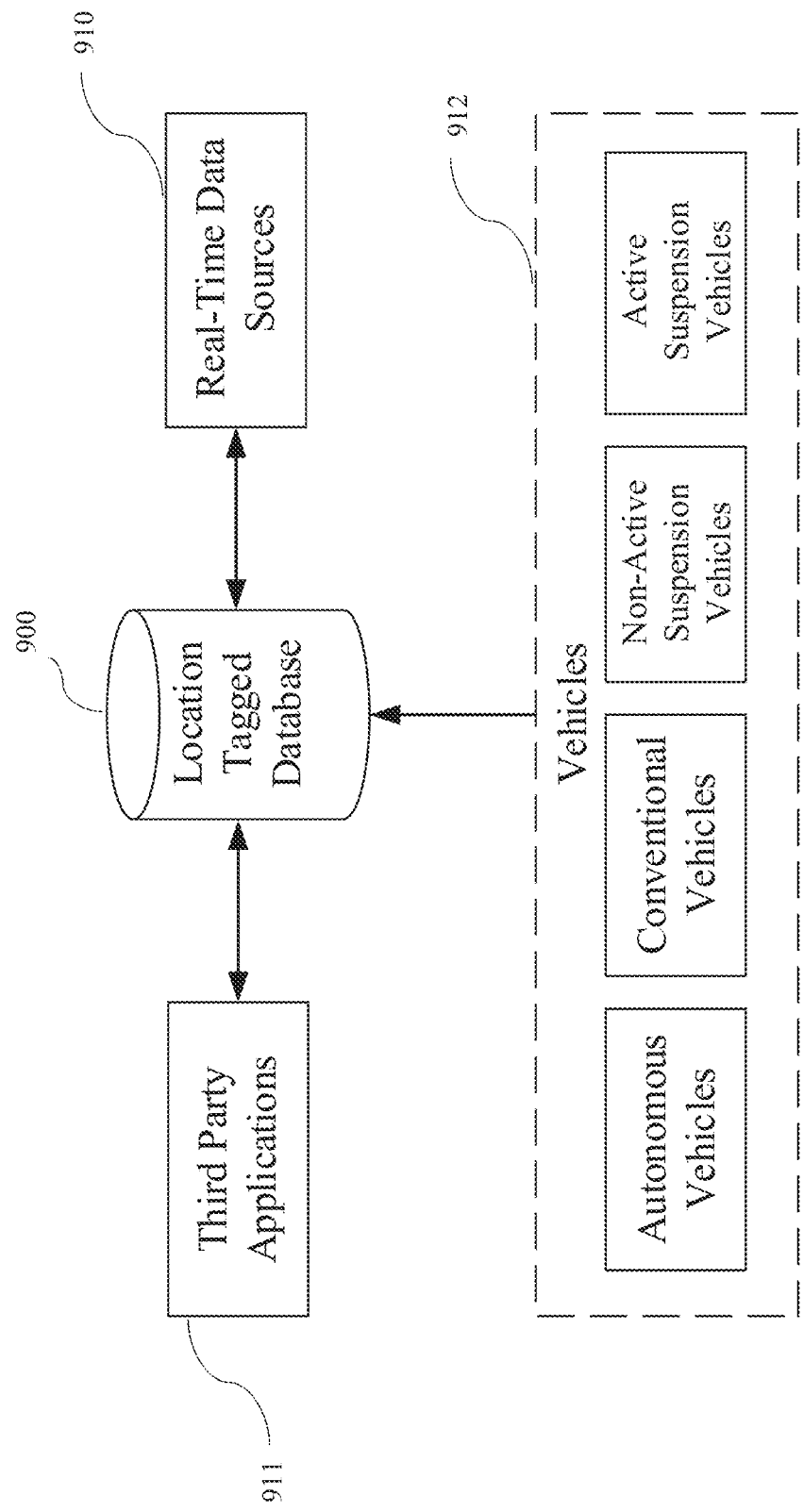
FIG. 38 illustrates a block diagram showing information exchange between a location tagged database and various data sources.

In some embodiments, the information in the LTD may also include, for example, traffic conditions and snow and ice cover obtained in real time from various sources, including but not limited to traffic reporting companies, municipalities, and/or police departments. In addition, data pertaining to road debris and/or short term road impediments or obstacles may be collected. In some embodiments, this data may be assigned a decay period and/or rate such that as the road impediment or obstacle is repaired, altered, or removed, data stored in the LTD may be updated after a period of time based on the number of reports that the impediment or obstacle is encountered by vehicles on the road. Any of this data may be supplied to any vehicle type such as autonomous and conventionally driven vehicles and vehicles with active, semi-active and passive suspension systems FIG. 38 illustrates an LTD 900 that is exchanging information with real-time data source(s) 910, third party applications 911, and multiple vehicles that may obtain information from various sources 912 such as controllers and/or sensors from autonomous vehicles, conventional vehicles, non-active suspension vehicles, active suspension vehicles, and/or any other appropriate source of information. The information exchange between the database and the vehicles may be in real-time and/or in batch form which may be transferred at a convenient time. For example, wireless communication and/or a physical internet connection may be used to transfer information between the LTD and the vehicles either continuously, as might be expected during use while driving, and/or when a vehicle is parked at an appropriate docking station or other type of connection. In certain embodiments, information transfer with one or more of these sources may be one directional or bidirectional.

Figure 39:
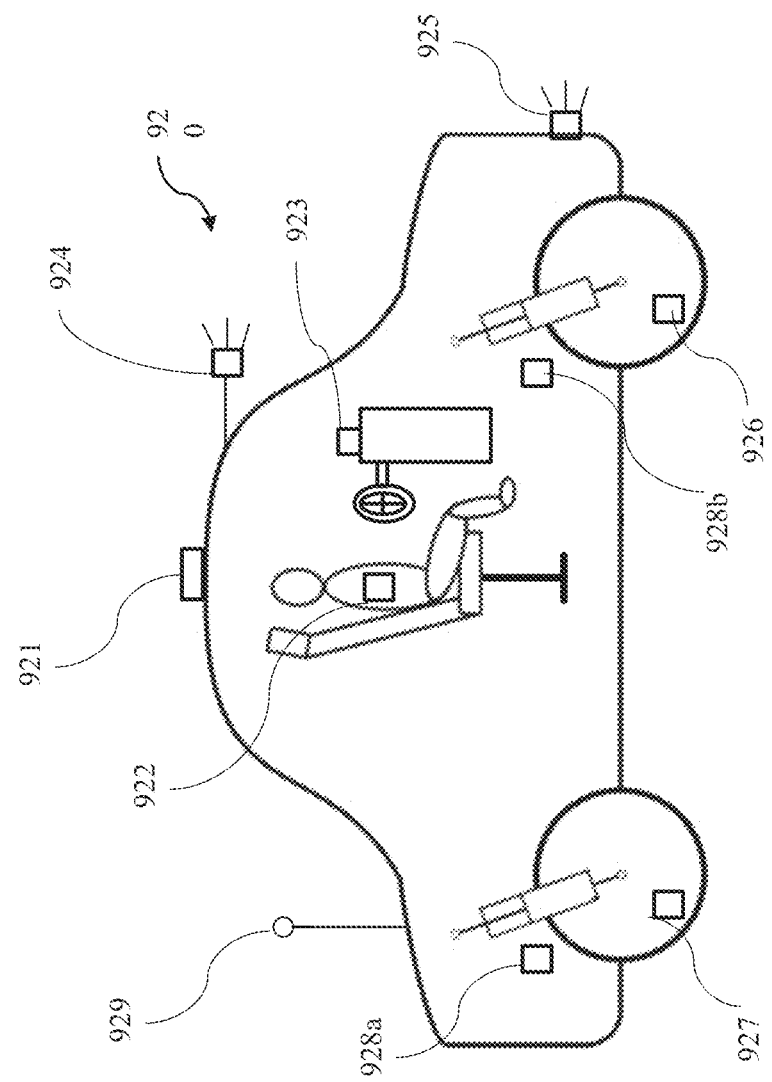
FIG. 39 is a schematic showing sensors associated with a vehicle for collecting information related to road inputs and vehicle occupants.

FIG. 39 illustrates an embodiment of an instrumented vehicle 920 that may collect and/or provide information about a road to an LTD. The information may be collected using sensors such as for example a GPS receiver 921, a human monitoring sensor 922 (e.g. accelerometers, worn devices, temperature sensors, etc.), a human machine interface 923 for reporting road events (e.g. a button or touchpad terminal for inputting information), optical sensors 924, Lidar 925, front wheel accelerometer 926, rear wheel accelerometer 927, chassis accelerometers 928a and 928b, and/or any appropriate sensor associated with either the vehicle and/or occupant located therein. As noted above, information may be exchanged, using a signal transmission/reception device 929, between a vehicle and a remotely located server and/or database, such as an LTD, using various types of communication including both physical connections and wireless communication including, without limitation, satellite communication, infrared, radio, microwave, Wi-Fi, and mobile networks the disclosure is not limited to any particular type of communication method.

Figure 40:
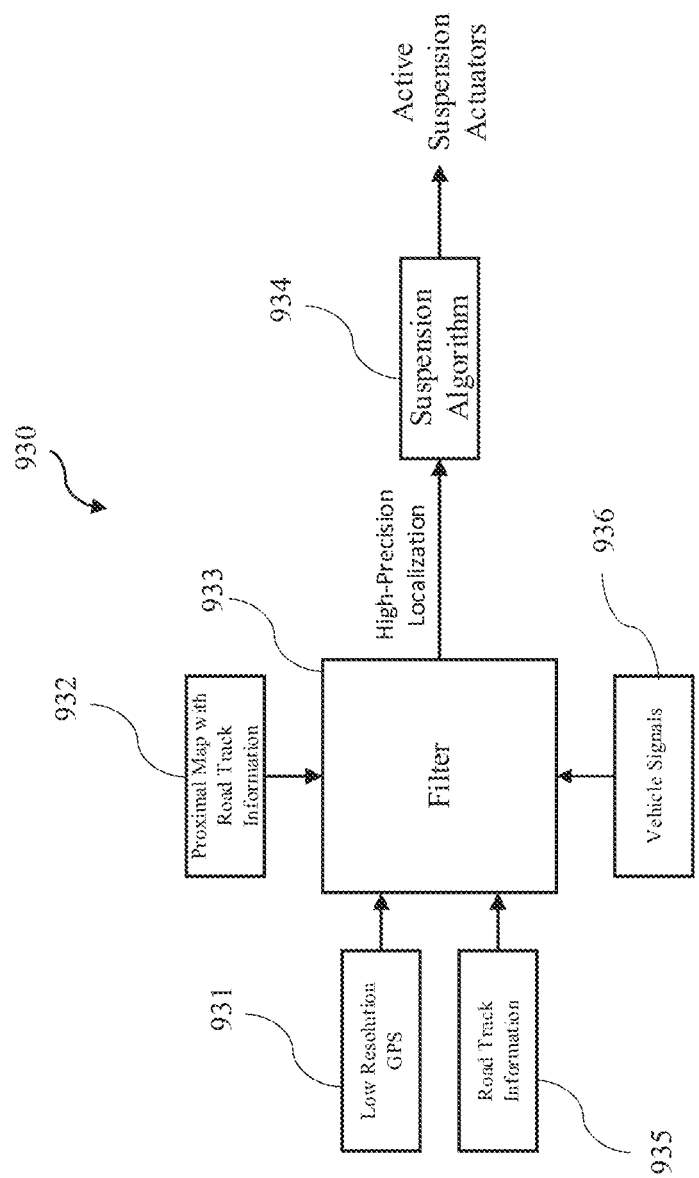
FIG. 40 illustrates a block diagram of an active suspension control system that receives information from low and high resolution sources.

FIG. 40 illustrates a block diagram of an embodiment of a controller 930 of one or more active suspension actuators of a vehicle. In one embodiment, low resolution GPS data 931 is collected and used to identify proximal information 932 associated with the segment of road the vehicle is located on. This proximal information may be obtained from a local database (i.e. an on vehicle database), a remote LTD, and/or a combination of the above. Sensor inputs 936 may include vehicle body accelerations, for example, from an IMU, speedometer readings, steering wheel positon, distances to objects, and other types of sensor data regarding the road a vehicle is traveling on may be compared to one or more patterns of features present in the proximal information 932. This sensed data may be compared to the stored patterns to identify matches between the sensed information and the proximal information by the road filter 933. This correlation between the sensed and proximal information may then be used to more accurately locate the vehicle within the road. This high precision localization may then be used to provide information to the suspension algorithm 934 in order to more effectively anticipate and respond to road characteristics.

Figure 41:
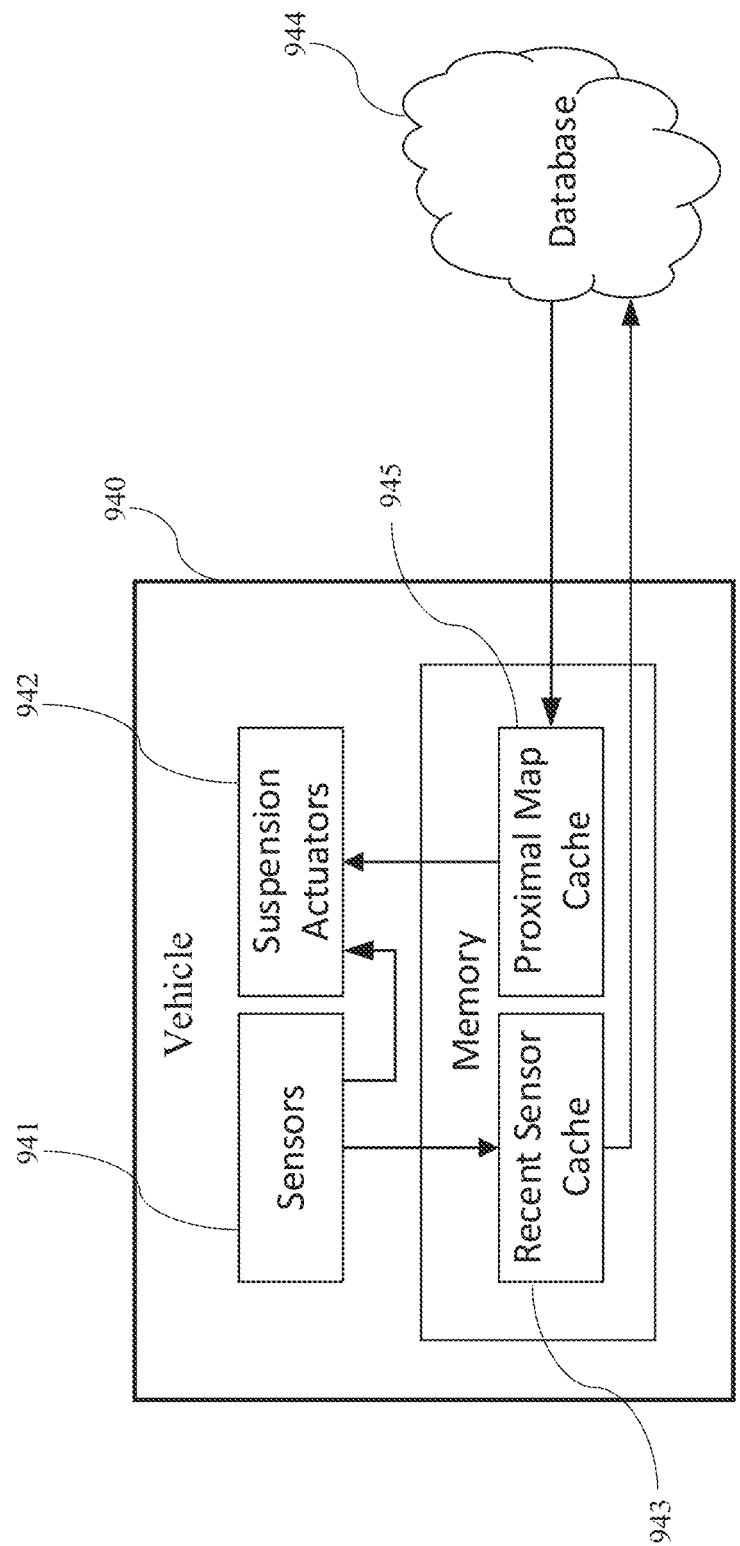
FIG. 41 illustrates a block diagram of an embodiment of a vehicle that collects and exchanges information with a database.

FIG. 41 illustrates a block diagram of one embodiment of the collection and exchange of information by a vehicle 940 with a database 944. In the depicted embodiment, sensors 941 collect information and provide at least some of the information to one or more suspension actuators 942 of an active or semi-active system. Some or all of the information collected by the sensors is then stored in a recent sensor cache 943. Some or all of the information sensor cache is also conveyed to a remotely located database 944, e.g. an LTD, in real time and/or at a convenient subsequent opportunity. Separately, information from the LTD may be received in the proximal map cache 945 of the vehicle and may be used in conjunction with the real time sensor data to control suspension actuators. As noted previously, any appropriate communication technique may be used to transmit data between the database and the vehicle.

Figure 42:
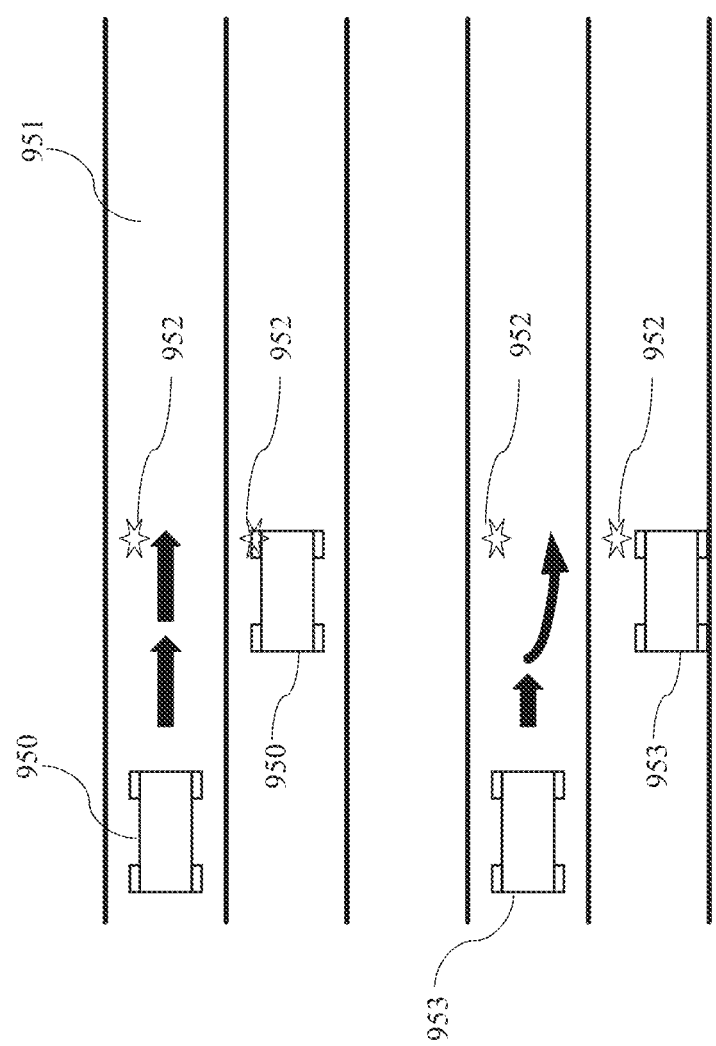
FIG. 42 illustrates the improved capacity of an autonomous vehicle to avoid road obstructions based on proximal map information.

FIG. 42 illustrates an autonomous vehicle 950 traveling down the center of a travel lane 951. In the depicted embodiment, the current travel vector of the vehicle 950 will impact with obstruction 952, which may be for example a pot hole, bump, or other feature. In contrast, vehicle 953, traveling along the same road with the same obstruction, may take evasive action, i.e. maneuver the vehicle out of a collision course with an obstruction. In one embodiment, the vehicle is able to take the noted evasive action using location specific information such as the proximal information and global positioning information noted above to identify upcoming obstructions within the path of travel. Using this information, as the vehicle approaches 952 the vehicle determines its position relative to the obstruction and determines a path of travel to avoid the obstruction while remaining within acceptable travel parameters. The path of travel may include moving within a single line, changing lanes, or any other appropriate vehicle maneuver. Once an appropriate path of travel has been determined, the vehicle controller may operate a steering system of the vehicle to change course so as to avoid the obstruction. Consequently, vehicle 953 may avoid the obstruction 952. This ability to evade obstructions may be used in conjunction with or instead of other obstruction avoidance techniques discussed herein.

Figure 10:
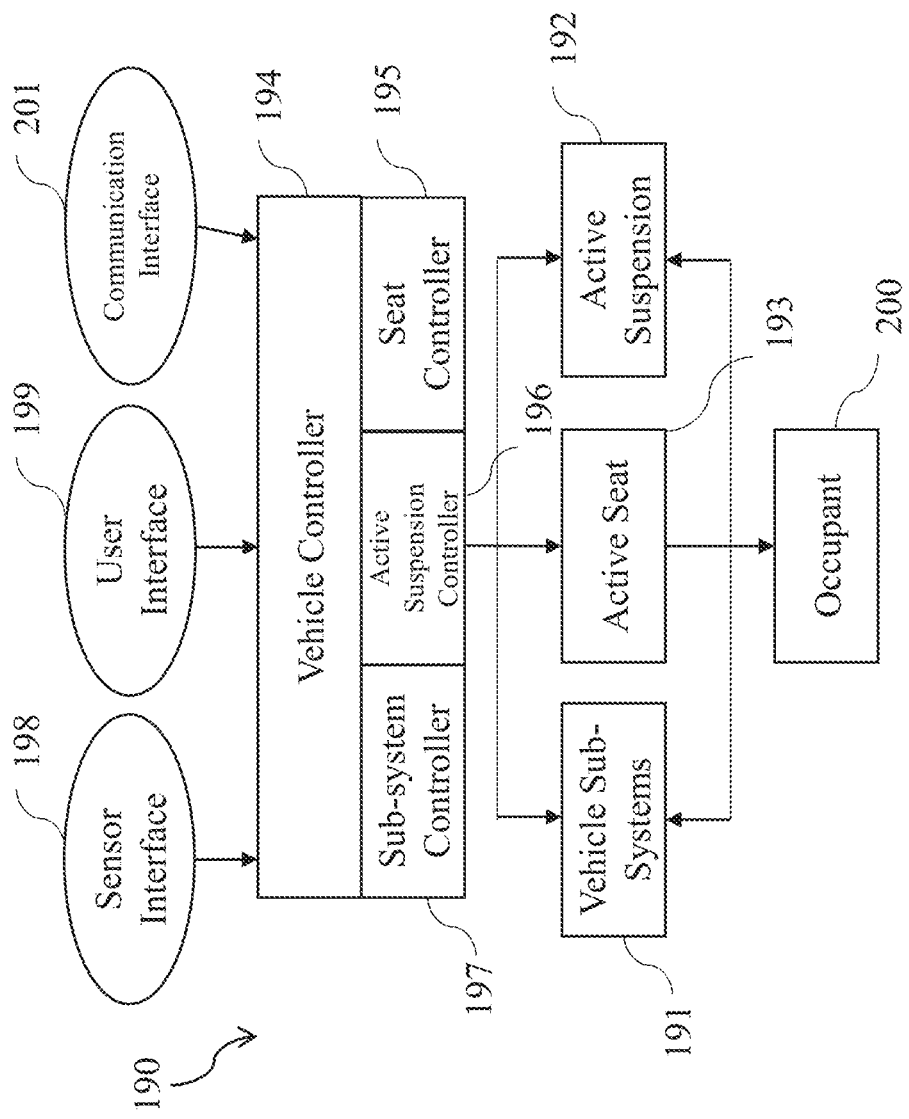
FIG. 10 is a block diagram of a control system for a vehicle for motion sickness mitigation.

FIG. 10 illustrates a block diagram of one embodiment of a control system 190 for an autonomous vehicle that is equipped with an active vehicle suspension system 192, an active seat suspension system 193, and/or one or more vehicle subsystems 191 (e.g. throttle, braking system, steering system, etc.). However, it should be understood that the any number of the various concepts described herein may also be implemented in a conventionally driven vehicle as well. In the depicted embodiment, a vehicle controller 194 may be a single integrated unit that encompass an active suspension controller 196, a seat controller 195, and a vehicle sub-systems controller 197 for controlling those functions (e.g. a throttling of the engine, braking, steering, etc.) of the vehicle. On the other hand, one or more of the sub-controllers may be housed separately from the vehicle controller. The vehicle controller receives sensor information from one or more sensors through a sensor interface 198 and also communicates with one or more vehicle occupants by means of one or more occupant inputs via a user interface 199. By controlling the active suspension system, the seat and other vehicle sub-systems, the vehicle controller is able to control the frequency and phase of road induced disturbances that are felt by an occupant 200. The controller may also be in electrical communication with a communication interface 201 to obtain information from an onboard database, other vehicles, and/or a central database. Again this information may be used by the controller to determine appropriate motion mitigation strategies and/or route planning at any given time and/or location.

Data may be received by a vehicle controller from various vehicle sensors and inputs including, for example, an accelerometer, a gyroscope, a load sensor, a laser or radar based range finder, an optical camera, an infrared camera, data received from vehicle occupant input, a combination of any of the above, and/or any other appropriate sensor. As noted above, user input may be in a variety of forms including, but not limited to, an indication that an autonomous vehicle mode is desired, an indication of passenger discomfort, an indication that a particular drive mode is desired (i.e. a sport mode versus an enhanced comfort mode). Information from one or more of these sensors may be fed into a pattern detection algorithm that resides in the vehicle controller 194. This pattern detection may be used to identify any desired event patterns related to vehicle motion including, for example, roll, pitch, heave, road surface irregularities, acceleration, braking, a combination of the foregoing, as well as any other appropriate type of motion. Patterns identified and the period over which they occur may be fed into the vehicle controller, a seat damper controller, and/or an active suspension controller. The appropriate controller may then command the vehicle, or sub-portion thereof, to take any corrective action needed such as, for example, altering vehicle speed and/or operating the suspension system to implement a desired corrective action. Again, corrective actions may include, for example, suppressing certain frequency bands to a greater degree and/or introducing energy (i.e. increased motion being transmitted to the vehicle body) in other frequency ranges as well as inducing motion within one or more portions of the vehicle, as well as any number of other strategies as the disclosure is not so limited.

In addition to monitoring a magnitude of disturbances in particular frequency ranges, pattern detection may also include monitoring an amount of energy consumed to mitigate motion within one or more frequency ranges for road induced disturbances. In such an embodiment, when an energy to mitigate disturbances within a particular frequency range used by an active suspension system, or other vehicle system, exceeds a threshold energy, the active suspension system may be controlled to mitigate motion within this frequency range to a greater degree. In some embodiments, the noted frequency range is a frequency range associated with motion sickness.

Figure 11:
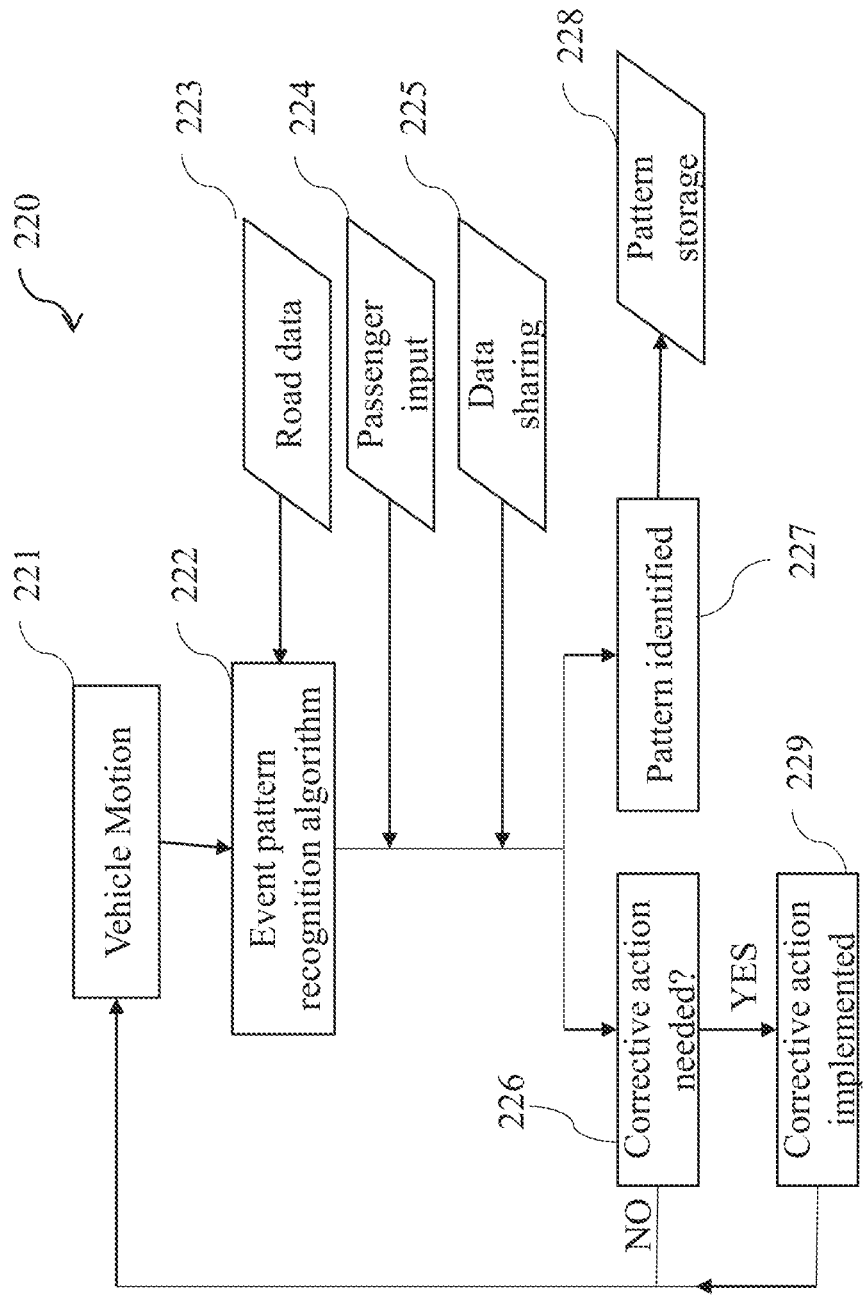
FIG. 11 is a schematic flow chart illustrating one embodiment of a motion sickness detection system.

Having described several exemplary systems that may implement motion sickness and road disturbance mitigation methods, an exemplary embodiment of a control method for a vehicle is illustrated in FIG. 11. The figure depicts a flow chart of a vehicle and/or suspension system control loop 220 being implemented. First, motion of one or more portions of a vehicle may be monitored at 221 using any appropriate arrangement of sensors including, for example, accelerometers oriented in desired directions, three axes accelerometers, gyroscopes, a vehicle velocimeter, IMUs, or any other type of sensor. These sensors may be sensitive to movements within a desired operating frequency range of the vehicle. As detailed further below, once the motion is detected by the sensors, a signal is transmitted to a controller of the vehicle and/or a motion mitigation system, such as a suspension system, to determine if the motions may correspond to an event pattern associated with motion sickness or other situation using an appropriate event pattern recognition algorithm at 222. The controller may also receive road data 223 that may be used to help identify event patterns and/or locations that may cause motion sickness. As noted previously, road data provided to the controller may include, but is not limited to, location related information such as traffic conditions, road features and topology, look ahead sensor data, speed limit ranges, and other appropriate types of information from any appropriate sensor or database.

At 226 information from one or more of the event pattern recognition algorithm 222, passenger inputs 224, and information from a database or separate vehicle that the vehicle is in communication with may be used to decide if one or more events have been present for a sufficient threshold duration and/or have a sufficiently severe magnitude that corrective action should be taken to mitigate the impact of these motions and/or situations on a vehicle occupant, see 226. Of course, while input from an occupant has been depicted as being considered in deciding whether or not corrective action may be needed, in some embodiments, motion sickness mitigation procedures may be used even without any feedback from vehicle passengers. For example, motion mitigation procedures may be implemented when a vehicle is traveling at speeds or under traffic conditions and/or within geographic locations, as determined through GPS coordinates, where the likelihood of motion sickness is elevated. Additionally, such mitigation procedures may be used continuously, for example for a particular trip, a portion of a trip, when the vehicle is used at particular times of the day, and/or for particular passengers.

Once it has been decided that an appropriate corrective action should be implemented, a controller of the vehicle and/or a sub-portion of the vehicle, such as a suspension system, may implement any appropriate motion and/or motion sickness medication strategy including those described herein at 229. Depending on the type, as well as severity, of an event and/or pattern, the corrective actions may either be taken immediately or after a predetermined threshold time period has elapsed and the event and/or pattern is still present. Various strategies that may be implemented include, but are not limited to, altering the performance characteristics of a suspension system within one or more frequency ranges associated with motion sickness, changing the speed of a vehicle over a particular road or changing the frequency of disturbances affecting the motion of the vehicle, as well as others described herein. Other strategies that may be used include, controlling vehicle acceleration, deceleration, turning rates, and/or turning radius to alter the frequency and/or magnitudes of pitch, roll, heave, lateral, and/or fore-aft accelerations affecting motion of the vehicle. Further, in some embodiments, if more than one vehicle occupant is suffering from discomfort, the vehicle control response may be tailored to, i.e. selected to appropriately address the motion sickness needs of, the passenger experiencing the most discomfort.

With regards to the passenger inputs noted above, in some embodiments certain high level modes may be available in an autonomous vehicle that can be selected by a vehicle occupant or automatically by the vehicle. A Stability Plus active suspension mode may be available where increased stability and comfort is provided. For example, occupants may request Stability Plus when an occupant is especially susceptible to motion sickness. Stability Plus may also be automatically implemented by the vehicle without occupant intervention if conditions are identified where there it is very likely, for example with greater than 75% likelihood that motion sickness will occur. In some embodiments a Traction Plus active suspension mode may also be selected by an occupant to provide increased road traction and a sport feel with increased feedback about road conditions. Traction Plus may be implemented automatically by the vehicle or requested by occupant indication, such as for example, when weather conditions are especially poor or there is a situation not adequately perceived by the vehicle, such as, for example, an oil spill. Occupants may also opt for increased traction to experience a more exciting or thrilling ride. An occupant may also select an Energy Plus autonomous vehicle mode to implement energy and/or power limits. Energy Plus may also be implemented automatically by the vehicle, for example, when the system determines that one or more portions of the system may not be functioning efficiently and/or energy needs to be conserved so that a particular trip can be completed. Additionally, an occupant may request an Energy Plus mode to conserve energy, for example, for environmental reasons.

One or more unique profiles may also be created and saved to a local and/or remotely located database to indicate personal suspension preferences previously input or determined for one or more occupants. For example, an occupant may be prone to motion sickness and may prefer a ride experience focused on comfort instead of speed. Each occupant can save a profile within the vehicle. Prior to the start of a trip, each occupant can indicate their presence to the vehicle, which will allow the vehicle to consider driving preferences based on the information stored in the local and/or remotely located database related to each indicated occupant before making decisions. In instances where individual seats are associated with separate secondary suspension systems. A performance profile can be set for each individual seat which will behave uniquely for each passenger according to personal preferences.

In addition to deciding whether or not to implement corrective actions on a vehicle, if an event or pattern is identified that is either associated with motion sickness at a particular location and/or a vehicle occupant indicates that the detected motions and/or events resulted in motion sickness, the vehicle may store this pattern and/or event at 227 and 228. Specifically, depending on the particular embodiment, the pattern and/or event may be stored both locally on a pattern and event database on the vehicle as well as being transmitted to a central server or database to supplement the location based information and/or patterns known to cause motion sickness for subsequent use in other vehicles as detailed above.

In addition to simply storing patterns, in some embodiments, when an occupant has indicated to a controller vehicle that they are experiencing discomfort and/or motion sickness above a preset threshold, data from one or more sensors indicative of one or more operational conditions of the vehicle and/or passenger conditions that may induce motion sickness are recorded and monitored. For example, using sensors situated inside the vehicle that track occupant motion, such as a camera, the vehicle may correlate passenger behavior with road occurrences. Other sensors that might be monitored include one or more sensors that monitor movement of one or more portions of the vehicle including the vehicle body and/or the passenger compartment. Appropriate types of motion sensors are listed previously above. Regardless of the particular sensors used, the detected events and/or patterns associated with the indicated occurrence of motion sickness may be uploaded into both a local storage and a remotely located server and/or database for subsequent usage. Therefore, these newly detected correlations may be used to better indicate to a vehicle situations that may cause occupant discomfort or motion sickness. Once these situations are identified, the vehicle may then take corrective action to prevent such motions from occurring again in the future, or at least mitigate their impact to one degree or another. For example, if a camera monitors head motions of an occupant, and a correlation is identified that undesirable head motion occurs at a particular location in a road at a certain combination of speed and occupant position, the vehicle will recognize and make adjustments to reduce head motion if the same location is visited in the future. This could be particularly useful for reducing vehicle discomfort associated with particular geographic locations.

It should be understood that events and/or patterns that may increase the likelihood and/or severity of motion sickness may be determined using any number of different methods for implementation in either the above described control loop and/or in other vehicle control systems. Several exemplary embodiments of methods and/or systems for detecting and identifying such events and/or patterns are detailed further below. However, while these various embodiments are described separately, it should be understood that these different embodiments may either be practiced individually, together, and/or in combination with any other appropriate detection method and system as the disclosure is not so limited.

As noted previously, in some embodiments, event patterns that affect the dynamics of a car and/or activities that are believed to increase the likelihood or severity of motion sickness are determined and stored a priori in a local database of a vehicle and/or remotely on a remotely located server/database in a manner where they may be accessed and/or retrieved by a vehicle controller. These event patterns may be determined empirically to cause motion sickness or deemed to do so by using predictive mathematical and/or empirical models. An event pattern is a series of events that occur over a period of time and affect the dynamic state of the vehicle during that period in a manner that affects an occupant in any number of ways. The impact on the occupant may be a function of a number of parameters such as, for example, the details of the vehicle motion and the activity being performed by an occupant of the vehicle. These event patterns, individually or as composites of multiple event patterns, may be used as templates for comparison during subsequent vehicle operation. These templates may be compared to event patterns that occur, in real time, during vehicle operation to identify events and/or patterns that should be mitigated in some form or fashion as detailed above.

In one embodiment, a particular event pattern, that occurs over a preset threshold time period, may be deemed to be likely to cause motion sickness based on, for example, the dynamics of a vehicle or movement of a passenger's head and/or torso. The models may involve empirical and/or mathematical relationships. For example, in an embodiment, one cycle of up and down motion of a vehicle body at a frequency between 0.3-0.4 Hz with a magnitude of 0.5 cm to 2 cm may be identified as a pattern that may induce motion sickness. If this pattern is repeated more than a preset number of times over a period of, for example, 5 minutes, a determination may be made that motion sickness is likely. Alternatively or additionally, a particular vehicle motion that results in side to side movement of a passenger's head at a frequency between 0.4-0.5 Hz with a magnitude of less than 2 cm may be identified as a pattern that may induce motion sickness. If this pattern is repeated more than a preset number of times over a threshold time period of, for example, 5 minutes, a determination may be made that motion sickness is likely. Of course, it should be understood that correlations associated with movements of an occupant's body at different frequencies both greater than and less than those noted above are also contemplated. For example, a control system may monitor the torso and/or a head of an occupant to determine if the occupant is being subjected to motions with frequencies associated with an increased likelihood of motion sickness including frequencies between or equal to about 0.05 Hz and 10 Hz as noted previously above.

In the above embodiments, the comparisons between the detected motions of the vehicle and/or occupant with one or more previously identified events and/or pattern templates may be based on instantaneous and/or average data that characterizes motion of the vehicle body, seats, and/or one or more portions of a passenger's body (e.g. torso, head, etc.) that occur over a period of time. If real time data from a vehicle matches or is similar to a previously obtained template over a certain period of time, for example up to 10 minutes, it may be used as an indication that there is a likelihood of motion sickness occurring on a particular route. Data obtained when developing the templates and during operation may be collected using one or more sensors such as, for example, cameras and accelerometers that capture the dynamics of the vehicle and/or one or more passengers. A determination of the likelihood of motion sickness may be based on the rate at which the patterns are repeated and/or the duration of the period of their occurrence.

In addition to the use of motion, a determination of increased likelihood of motion sickness in a vehicle occupant may be based at least partially on physiological parameters and/or direct inputs from the occupant. In one such embodiment, one or more cameras may be used for facial recognition of one or more passengers within the vehicle, in order to identify the passengers, as well as to measure head movements of the one or more passengers in the vehicle as noted above. Microphones (with speech recognition) and other communication interfaces may be used by the vehicle controller to communicate with passengers and for passengers to communicate with the vehicle. For example, a vehicle occupant may indicate the severity of motion sickness and/or a desired mode of operation to the controller which may then subsequently be used to determine appropriate motion and/or motion sickness mediation techniques to be implemented during vehicle operation. The physiological state of the one or more passengers may also be sensed including parameters, such as galvanic skin response at various locations on a person's body, temperature, heart rate, blood oxygen and carbon dioxide levels, hydration levels, and/or other metrics. Such physiological sensing may be conducted by the vehicle, or by wearable devices such as an electronic bracelet or smart watch with the appropriate sensors built therein. In one such embodiment where physiological symptoms conducted by the vehicle, the various sensors may be integrated into a seat that an occupant is located in such that the sensors may simply be in contact with the occupant simply by sending seated in and/or the seat may include portions that may be touched, such as in the case of electrodes grasped by an occupant's hands, to sense the desired physiological parameters of the occupant.

In some embodiments, a vehicle may be equipped with sensors and/or communication devices, such as a Bluetooth device, a Wi-Fi connection, a plug, or any other appropriate device capable of exchanging information with wearable devices (such as for example smart watches), or other equipment carried by individual passengers (such as for example smart phones and ipads). Such communication devices may also include sensors which may automatically collect data from individual passengers. Additionally or alternatively, information about passenger well-being may be collected by in-seat sensors or other sensors in, and/or on, the vehicle. Information exchanged with such devices, which may be bi-directional and/or occur privately so other passengers are unaware of it, may include commands initiated by a particular authorized individual or may include automatically collected health, physiological, wellbeing, and/or comfort information. Information collected may, for example, be used to determine if the person is feeling symptoms of motion sickness. The information may then be used by the vehicle to automatically adjust its operation to maintain the health, wellbeing and safety of vehicle occupants, and/or to respond to the commands from individual passengers. The vehicle may also communicate with a remote location for further guidance on how to respond to commands or information from individual passengers. In emergency situations, the vehicle may divert to, for example, the nearest appropriate hospital or police station and the hospital or police station may be notified of the situation before arrival.

Elaborating on the embodiment of a vehicle and/or suspension system controller receiving input from one or more occupants of a vehicle, a controller of a vehicle may receive information from one or more vehicle occupants indicating that at least one occupant is suffering from motion sickness. Additionally, the level of motion sickness of the passenger may be provided to the vehicle controller. The degree of motion sickness may be communicated, for example, by using a knob or a touch sensitive surface. In one embodiment, the degree of motion sickness may be measured using physiological sensors, such as by comparing galvanic skin response (e.g. measuring sweat) in the palm of the hand with that of the dorsal part of the hand and arm. Further, in some instances, a motion sickness condition may be characterized by a rapid onset palmar sweat response followed by subsequent hand and arm dorsal sweat response. Cameras and/or optical sensors may also be used to collect infrared information to determine skin temperature of one or more passengers.

As noted previously, in some embodiments, if one or more passengers reports discomfort, such as motion sickness, a vehicle may then retain a record of recent event patterns. Further, such event patterns may be used to update or supplement the vehicle's event pattern database/and/or may be shared with other vehicles and/or remote servers or database. In such an embodiment, event patterns may be recorded continuously such that when an occupant communicates to a vehicle and/or suspension controller that a motion sickness event has occurred, the previously occurring event pattern may be stored and identified as one that causes motion sickness in general and/or for a particular passenger. Depending on the particular embodiment, event patterns may be recorded continuously for any appropriate time including, but not limited to, 1 min. to 10 min. 5 min. to 10 min., 10 min. to 20 min., or any other appropriate amount of time including time periods both greater and less than those noted above.

In yet another embodiment, video monitoring of one or more vehicle occupants may again be used to determine the likelihood of motion sickness. However, in this embodiment, the eyes of a person looking at an object such as a computer screen, or other display, may be monitored and the relative movement of the person's eyes and the display may be determined. Based on this information, the amount of retinal slip an occupant is experiencing while viewing the display may be determined. The amount and/or the frequency of retinal slip and the duration of the period over which it occurs may be compared to predetermined thresholds for these quantities. Based on this comparison, motion sickness mitigation procedures may be instituted.

The Inventors have appreciated that it may be possible to mitigate motions transmitted to one or more portions of the vehicle by moving a mass in an appropriate correction to apply a force to the desired portion of the vehicle that opposes road induced forces and disturbances transmitted to that portion of the vehicle. Further, the inventors have recognized that the large mass of a battery of an electric and/or hybrid vehicle, makes up a significant portion of the vehicle's weight. For example, Electric vehicles (EVs) and many hybrid-electric vehicles (HEVs) require extensive onboard electricity storage capacity, and batteries used for this purpose are typically quite heavy. Specifically, in a Tesla Model S, the Lithium Ion battery pack weighs approximately 1,200-1,500 pounds, which represents approximately 25%-33% of the curb weight of the vehicle. Therefore, in some embodiments, movement of a battery relative to one or more portions of a vehicle, can be utilized to at least partially control the motion of the vehicle body, or sub-portion thereof, in order to improve the ride quality for the occupants and/or loads located within the vehicle. Of course, while moving a battery pack relative to other portions of the vehicle to mitigate motions transmitted to those portions of a vehicle has been discussed above, it should be understood that the current disclosure is not limited to only using batteries. For example, embodiments in which other components having a sufficient mass are used to mitigate motion transmitted to a particular portion of a vehicle are also contemplated as the current disclosure is not so limited.

In the above embodiment, the mass moved relative to one or more portions of the vehicle may have any appropriate mass. However, in one embodiment, the mass may be greater than or equal to about 20%, 30%, 40%, or any other appropriate percentage of a vehicle's weight. Correspondingly, the mass may be less than or equal to about 60%, 50%, 40%, or any other appropriate percentage of a vehicle's weight. Combinations of the above ranges are contemplated including, for example, a mass with a weight between or equal to about 20% and 50% of a vehicle's weight. Of course, masses with weights both less than and greater than those noted above are also contemplated as the disclosure is not limited in this fashion.

Figure 12:
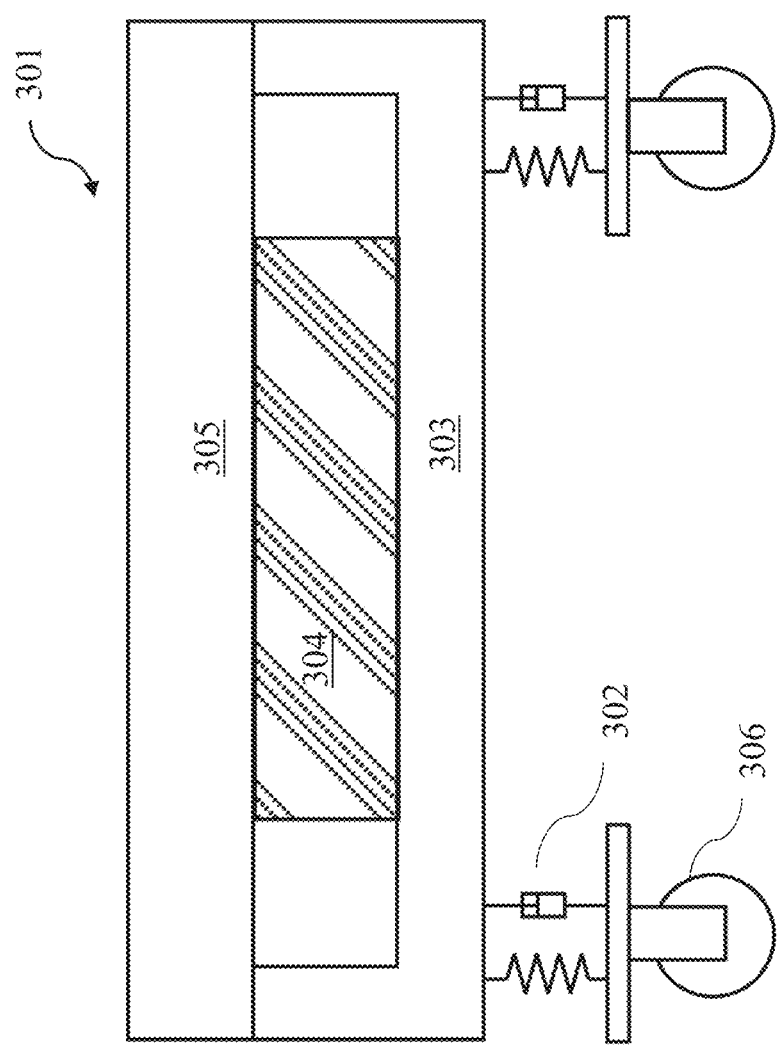
FIG. 12 is a schematic of an embodiment that illustrates the relative positioning of the battery of an electric car, the chassis or (undercarriage), and the passenger compartment or cab.

FIG. 12 illustrates a schematic of a prior art construction of an electric or hybrid-electric vehicle 301 where a vehicle passive or semi-active suspension 302 is disposed between one or more wheels of the vehicle and a corresponding vehicle chassis (or undercarriage) 303 such that the chassis or undercarriage is supported by the suspension. In similar fashion, the chassis or undercarriage 303 typically supports and is fixedly attached to a battery 304 located within the vehicle body. The vehicle also includes a passenger compartment 305 supported by the vehicle chassis.

Figure 13:
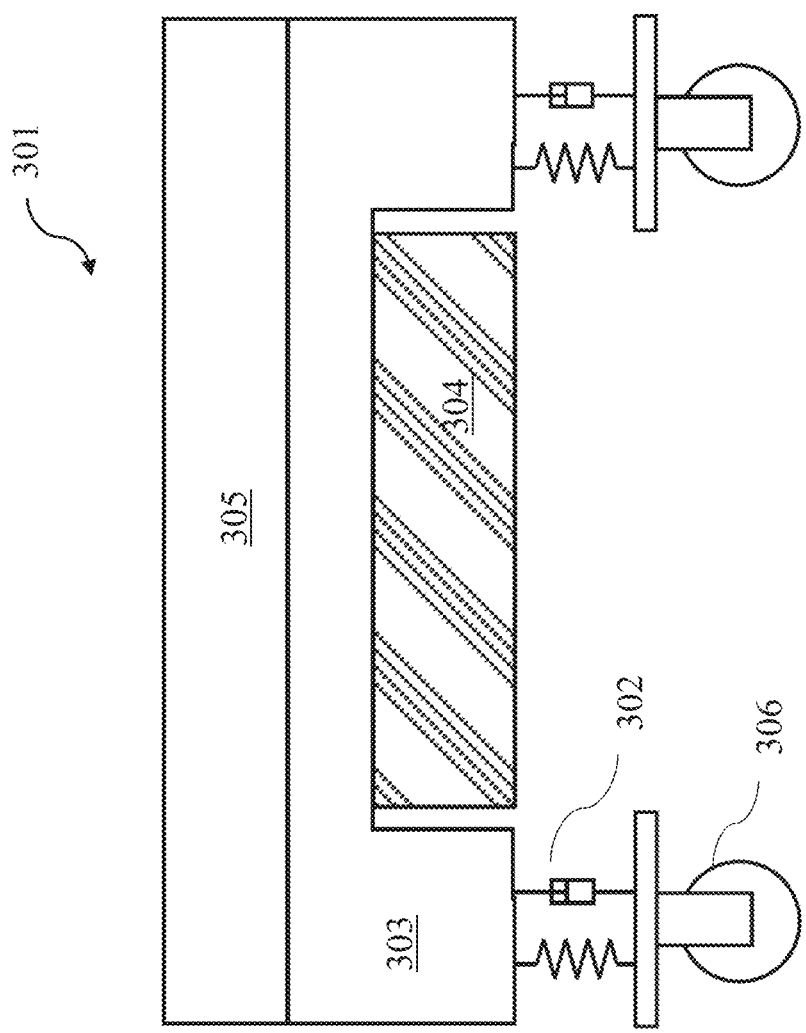
FIG. 13 is a schematic of an embodiment that illustrates an alternative relative position of the battery with respect to the chassis (or undercarriage) and the passenger compartment or cab.

FIG. 13 illustrates an alternative prior art construction of an electric or hybrid-electric vehicle 301. Again, in the depicted embodiment, a suspension system 302 is disposed between the chassis or undercarriage 303 and the one or more wheels 306 such that the suspension system supports the vehicle body. However, in this embodiment, a battery 304 is located under, and fixedly attached to, the chassis (or undercarriage) as might be done to facilitate easy access and/or replacement of the battery. The passenger compartment 305 is fixedly attached to the chassis (or undercarriage).

While two wheel assemblies are shown in the embodiments, each including a damper and a spring, it should be understood that other types of suspension systems may be associated with each wheel. For example, in typical vehicles, the suspension system may be a passive or semi-active suspension system. Additionally, electric vehicles and hybrid electric vehicles typically have three or four wheels, though vehicles such as electric or hybrid electric motorcycles with only two wheel assemblies are also contemplated.

Figure 14:
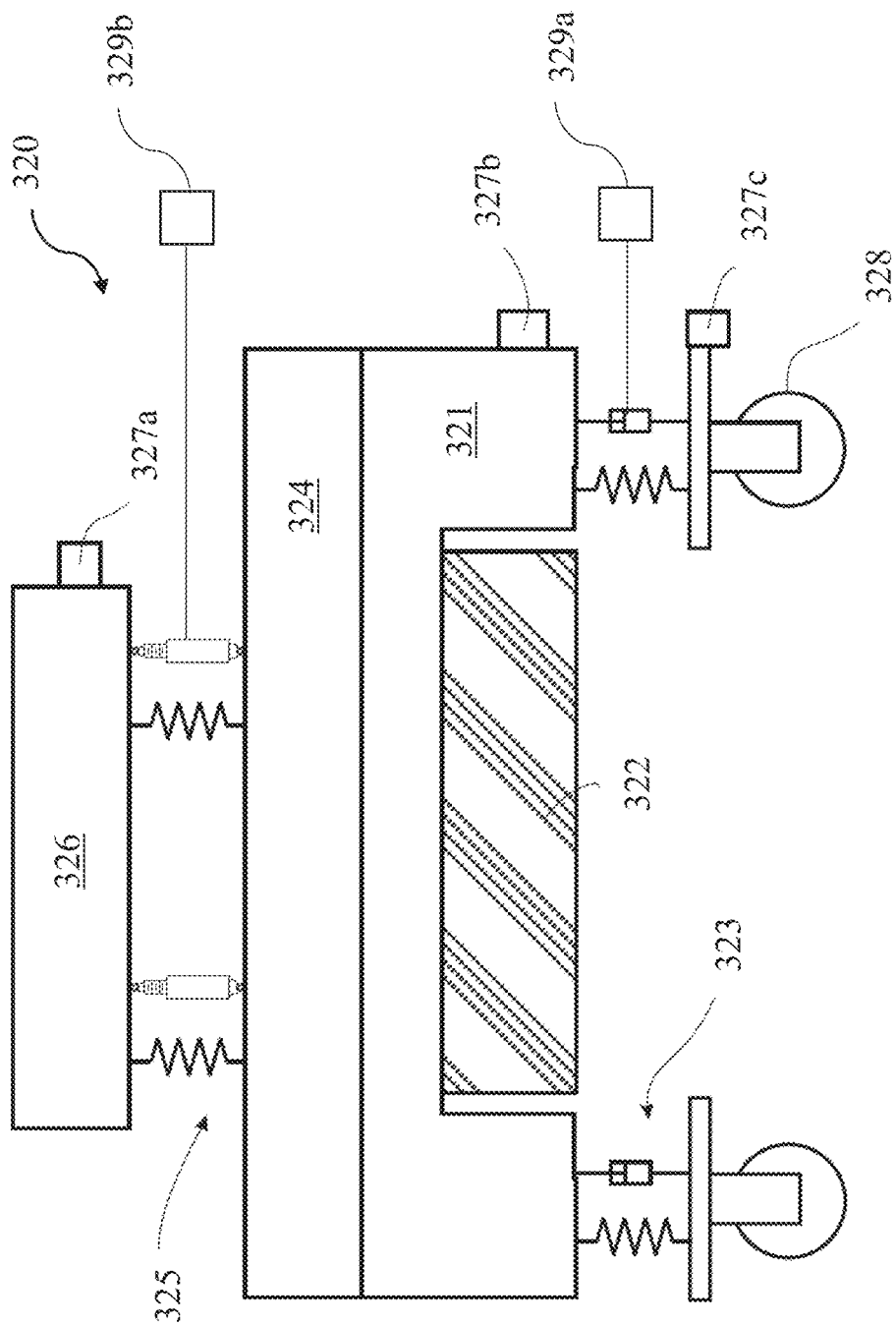
FIG. 14 is a schematic of an embodiment that illustrates the relative positioning of the battery with respect to the chassis (or undercarriage) and the passenger compartment or cab where a unit, in the passenger compartment, such as a chair and/or work surface is allowed to float relative to the passenger compartment or cab using an active suspension system.

FIG. 14 illustrates an embodiment of a vehicle 320 where one or more portions of a a vehicle body such as a chassis (or undercarriage) 321 as well as other associated components such as a battery 322, or other mass, are attached to, and supported by, a primary suspension system 323. In the depicted embodiment, the primary suspension system is disposed between the vehicle body and one or more wheels 328. While the primary suspension system is shown as a passive suspension system, it should be understood that the current disclosure is not so limited. For example, a passive, semi-active, or fully active primary suspension system may be used. Further, in some embodiments, the active suspension may be electrohydraulic or electromagnetic. Similar to the above vehicles, the vehicle also includes a passenger compartment 324 that is fixed relative to the battery and/or chassis assembly. Further, it may be desirable to include one or more secondary suspension systems 325 disposed between at least second and third portions of the vehicle such as a passenger compartment 324 and one or more separate structures 326 associated with the passenger compartment such as a chair and/or a work surface (e.g. a table or a desk) located within the passenger compartment.

In the embodiment depicted in the figure, the vehicle may also include one or more sensors 327a, 327b, and 327c which may be located either within an interior and/or on an exterior of a vehicle. Further, these sensors may be used to collect information, such as, for example, one or more of, the absolute values or relative acceleration, velocity and position of various portions of the vehicle including for example, the vehicle chassis (or undercarriage) 321, one or more wheel assemblies 327, the passenger compartment 324, and/or the one or more separate structures 326 associated with the passenger compartment 324. While the separate structure 326 is shown to be outside the passenger compartment 324 for the sake of clarity, it should be understood that the one or more structures may be located within and, in some embodiments, encompassed by, the passenger compartment 324.

One or more controllers, such as the suspension system controllers 329a and 329b may be in electrical communication with the primary and secondary suspension systems 323 and 325 respectively. Alternatively, a central vehicle and/or suspension system controller may be in electrical with the various suspension systems of the vehicle. Additionally, each suspension system may either be controlled by a central controller and/or a distributed control system including a plurality of controllers with each separate actuator and/or damper associated with a separate controller that, in some embodiments, may be in electrical communication with a central control system of the vehicle. In either case, a controller may operate the primary and/or secondary suspension systems, as well as any other suspension system of the vehicle, to control the motion of the structure, passenger compartment, and/or vehicle body. Further, depending on the embodiment, oscillations, or other motions, attenuated by the primary suspension system 323 and those attenuated by the secondary suspension system 325 may be over the same or different frequency ranges. For example, the primary suspension system may be used to primarily reduce motions in a frequency range that is greater than a primary frequency range of the secondary suspension system. In one such embodiment, the primary suspension system may reduce motions in a frequency range between or equal to about 2 Hz-20 Hz to a greater degree than the secondary suspension system. Accordingly, the secondary suspension system may be used to reduce motions in a frequency range between or equal to about the 0.5 Hz and 2 Hz to a greater degree than the primary suspension system. Of course, as noted previously, the primary and secondary suspension systems may be operated relative to each other in different frequency ranges both greater than and less than those noted above.

Figure 15:
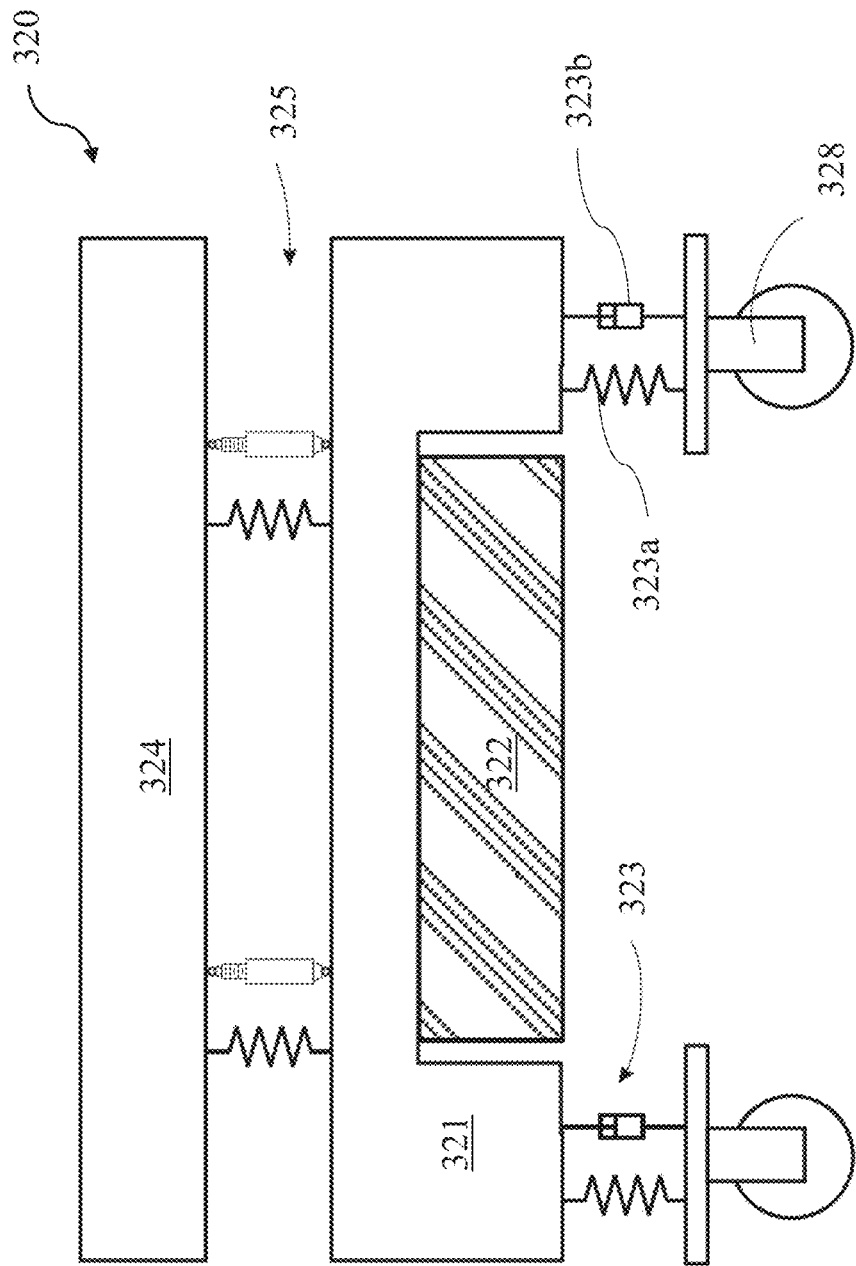
FIG. 15 is a schematic of an embodiment that illustrates the relative positioning of the battery with respect to the chassis (or undercarriage) and the passenger compartment or cab where the passenger compartment or cab is allowed to float relative to an assembly containing the battery and the chassis (or undercarriage)

FIG. 15 illustrates another embodiment of vehicle 320 where the chassis (or undercarriage) 321 is supported by primary suspension system 323. At each wheel assembly 328, a spring 323a and a passive damper 323b are interposed between the wheel assembly and the chassis (or undercarriage). Depending on the particular embodiment, the passive damper may be replaced by a semi-active damper and/or any appropriate type of fully active actuator. In addition to the primary suspension system, a separate portion of the vehicle such as the passenger compartment or cab 324, may also be supported by a secondary suspension system which may be a fully active suspension system. Though embodiments in which a passive and/or semi-active suspension system is used are also contemplated.

In the case of an electric, or hybrid electric, vehicle a vehicle battery 322 with a relatively large mass is associated with the vehicle body. Therefore, road disturbances transmitted to the vehicle body through the associated wheel assemblies may be at least partially attenuated by the large battery mass before they are transmitted to the passenger compartment or cab 324. Accordingly, the amount of damping or disturbance mitigation that may be required of a secondary active suspension system 325 may be less than in other embodiments. As a result, a smaller and less powerful secondary suspension system may be used. Of course, while the use of a relatively large battery mass has been described above for helping to mitigate motions transmitted to a passenger compartment, embodiments in which a different type of mass, such as a vehicle load and/or a portion of the vehicle, is used to help mitigate motion transmitted to the vehicle cab are also contemplated.

Figure 16:
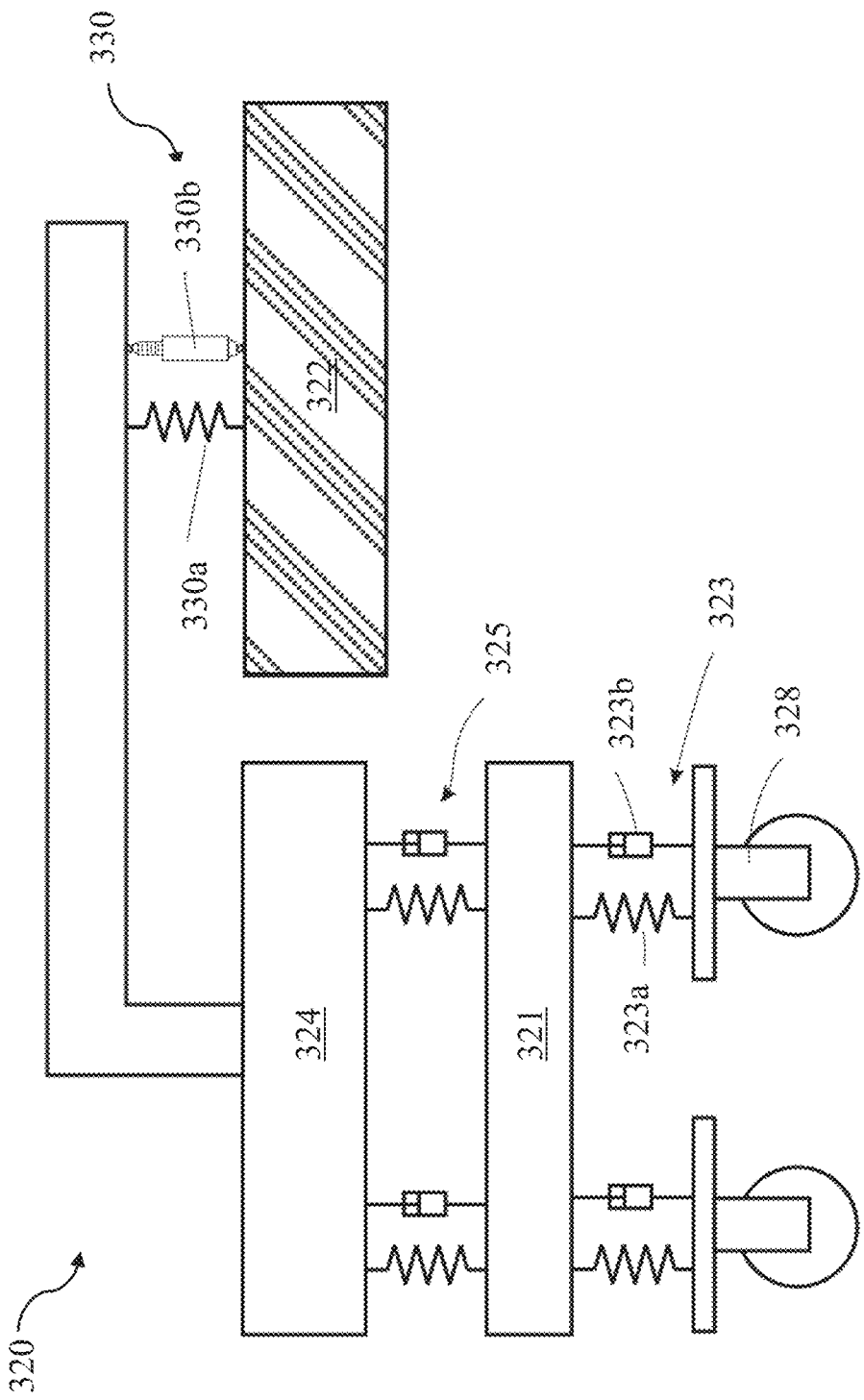
FIG. 16 is a schematic of an embodiment that illustrates the relative positioning of the battery with respect to the chassis (or undercarriage) and the passenger compartment or cab where the passenger compartment or cab is allowed to float relative to the chassis (or undercarriage) and the battery is suspended from the passenger compartment.

FIG. 16 illustrates an embodiment of a vehicle 320 where a chassis (or undercarriage) 321 is supported by primary suspension system 323. At each wheel assembly 328, a spring 323a and a passive damper 323b are interposed between the wheel assembly and the chassis (or undercarriage). However, it should be understood that the passive dampers may be replaced by a semi-active damper or any type of fully active actuator. The passenger compartment or cab 324 is supported by a secondary suspension system 325 which is interposed between it and the chassis (or undercarriage) 321. In this embodiment, the secondary suspension system is a passive system, although semi-active and fully active suspension systems may also be used.

In addition to the primary and secondary suspension systems, in the depicted embodiment, a large mass, which in this embodiment may be a battery 322 of an electric vehicle or hybrid electric vehicle, may be suspended from, or supported by, the passenger compartment or cab 324 using third suspension system 330 located between the mass and the passenger compartment. In one embodiment, the third suspension system includes one or more active actuator s 330b and one or more springs 330a. In the depicted embodiment, the actuator is an electromagnetic actuator although other active actuators may be used including, for example, an electro-mechanical and/or electrohydraulic actuator. Depending on the particular application, the actuator may be constructed and operated to reduce motions applied to the passenger cab within one or more frequency ranges such as Alternatively, the actuator may be replaced with a damper so that the battery mass operates as a tuned mass damper, but such a damper will be effective over a more narrow range of frequencies than is possible with an active actuator.

Figure 17:
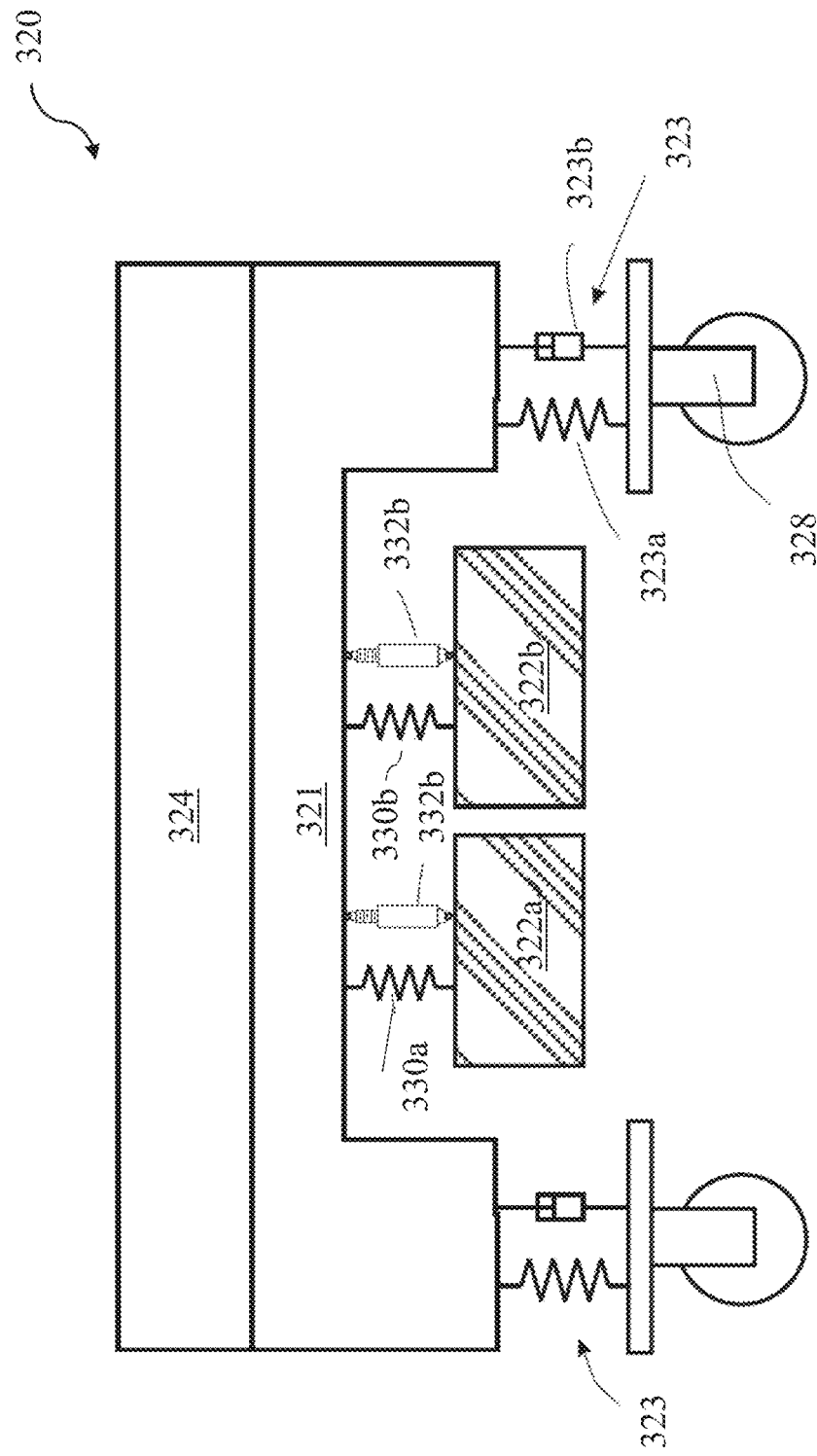
FIG. 17 is a schematic of an embodiment which illustrates where the chassis (or undercarriage) is supported by a suspension system, where the passenger compartment is fixedly attached to the chassis (or undercarriage), and where separate masses are suspended from the chassis or undercarriage.

FIG. 17 depicts an embodiment of vehicle 320 where the chassis (or undercarriage) 321 is supported by a primary suspension system 323. At each wheel assembly 328, a spring 323a and passive damper 323b of the suspension system are interposed between the wheel assembly and the chassis (or undercarriage). Of course, similar to the other embodiments, the passive dampers may be replaced by a semi-active damper or any type of fully active actuator. In this particular embodiment, the passenger compartment or cab 324 is attached to the chassis (or undercarriage) without a suspension system disposed there between. However, embodiments in which a secondary suspension system is located between the passenger compartment and chassis are also contemplated.

A mass, which in this embodiment may be a large battery, is divided into two or more masses 322a and 322b where each is suspended from, or otherwise supported, by the chassis (or undercarriage) 321. Each mass is attached to the chassis (or undercarriage) through a suspension system located between the masses and the vehicle body using, for example, springs 330b and 332b and by actuators 330a and 332a. Accordingly, forces exerted on the chassis (or undercarriage) may be at least partially mitigated by inducing a relative motion between the chassis and either a portion of the total mass (i.e. moving one or more individual masses or batteries) or the entire mass (i.e. moving all of the masses or batteries). Again this relative motion of the one or more masses relative to the chassis will apply a force to the chassis, or other portion of the vehicle it is associated with, which may be controlled to at least partially mitigate motion transmitted to the vehicle by road disturbances.

In addition to the above, in the depicted embodiment, the battery mass is shown as being broken up into two equal masses. Alternatively, the mass may be kept whole or it may be broken up into a plurality of masses with either equal or different masses as the disclosure is not so limited. For example, a large battery may be broken up into different battery packs with different total electrical capacities and masses, the same capacities and masses, and/or maintained as a single unit.

Figure 18:
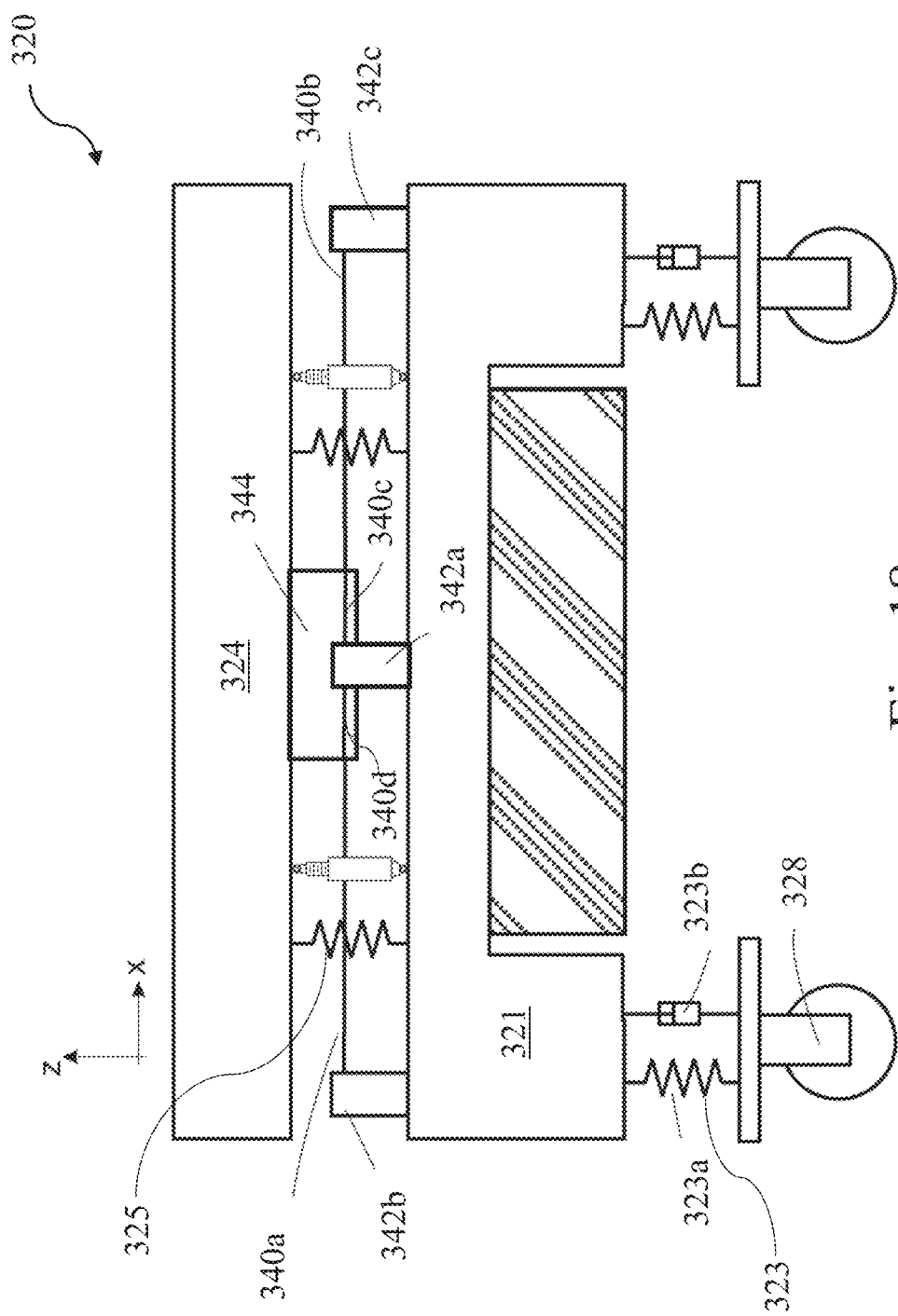
FIG. 18 is a schematic of an embodiment including a battery attached to the chassis and where the passenger compartment or cab floats with respect to the chassis (or undercarriage) in the vertical direction, but is constrained in at least one lateral direction.
Figure 19:
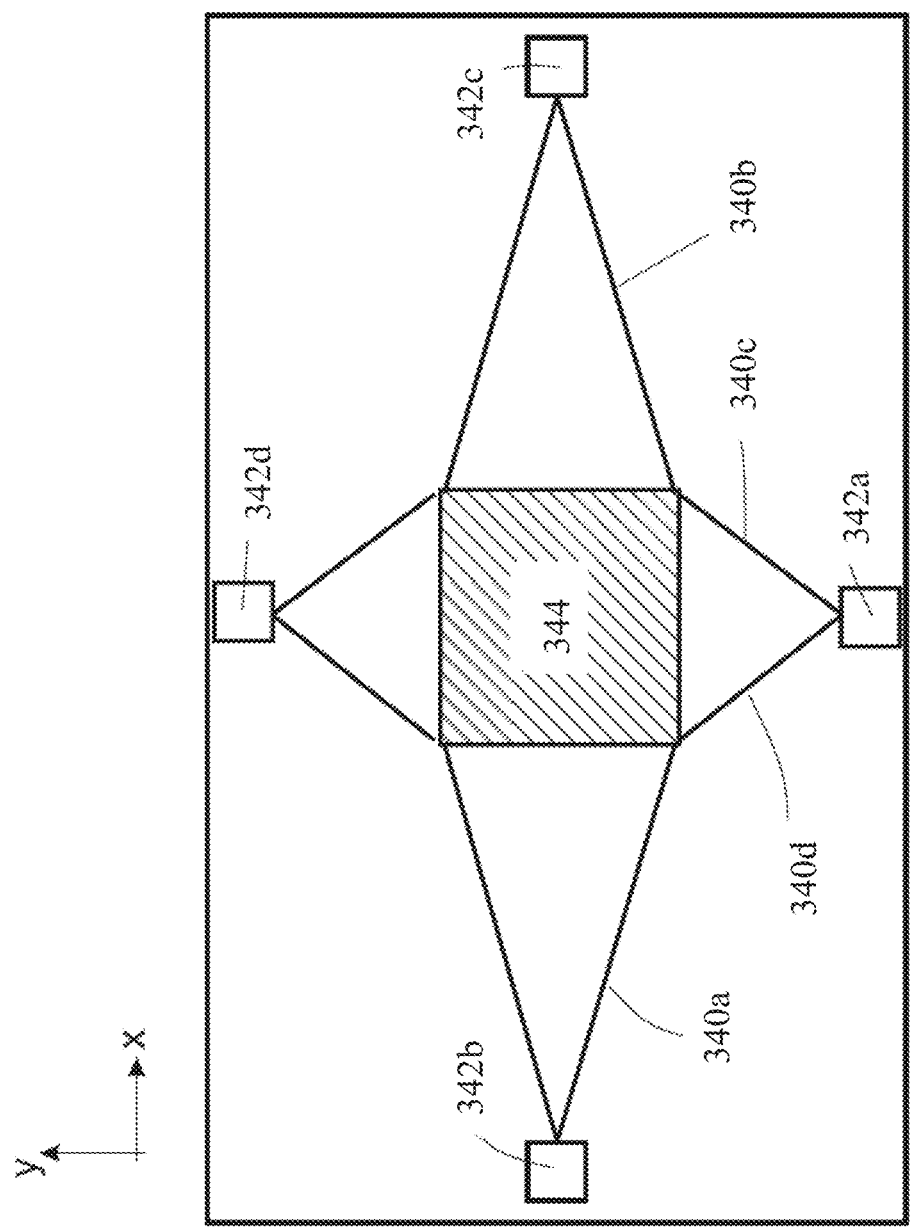
FIG. 19 illustrates the constraining mechanism of the embodiment in FIG. 18.

FIGS. 18 and 19 illustrate yet another embodiment of a vehicle 320 where the chassis (or undercarriage) 321 is supported by primary suspension system 323. At each wheel assembly 328, spring 323a and passive damper 323b are interposed between the wheel assembly and the chassis (or undercarriage) though embodiments in which semi-active and/or active suspension systems are used are also contemplated. In some embodiments, a secondary suspension system may also be located between the vehicle chassis and the passenger compartment or cab 324 of the vehicle. In addition to the various suspension systems, a lateral stabilization system may be used to reduce, or eliminate lateral motions relative to the ground of one or more portions of the vehicle. The lateral stabilization system in the depicted embodiment includes one or more cables 340a, 340b, 340c, and 340d that may be attached to and extend between posts fixed relative to the chassis 342a, 342b, 342c, and 342d as well as one or more posts 344 fixed relative to the passenger compartment or other portion of the vehicle.

FIG. 19 depicts the relationship of the stability cables and the four posts 342a, 342b, 342c, and 342d attached to a chassis (or undercarriage) and the post 344 that is attached to the passenger compartment or cab. In the depicted embodiment, the four posts fixed relative to the chassis are located towards a center of each side of the vehicle chassis, though any appropriate location may be used as well. Correspondingly, the post fixed relative to the passenger compartment is located towards a center of the passenger compartment, though again other appropriate locations may also be used. One or more cables 340a-340d extend between the posts associated with the chassis and the one or more posts associated with the passenger compartment. In this particular embodiment, two cables extend between each post of the chassis and the central post associated with the passenger compartment.

The cables may be sufficiently stiff to reduce, or prevent, lateral movement of the passenger compartment relative to the vehicle chassis. This may either be due to appropriate tensioning of the cables as well as their structural properties and/or one or more springs and/or actuators may be located in line with the cables to provide a desired amount of stiffness to the cables. In one embodiment where actuators are located in line with the cables, the stiffness, and corresponding lateral stabilization of the passenger compartment relative to the chassis may be dynamically varied. For example, the tensioning of one or more cables relative to the other cables may be used to displace the passenger compartment in a desired direction.

The above embodiment uses posts associated with various portions of the vehicle, such as the chassis and passenger compartment, for attaching one or more cables. However, it should be understood that any appropriate attachment point to a particular portion of a vehicle may be used including, but not limited to, clamps, interlocking components, through holes, interferences between portions of the vehicle portion and an end of a cable, or any other appropriate configuration capable of attaching a cable to a vehicle portion as the disclosure is not so limited.

Figure 20:
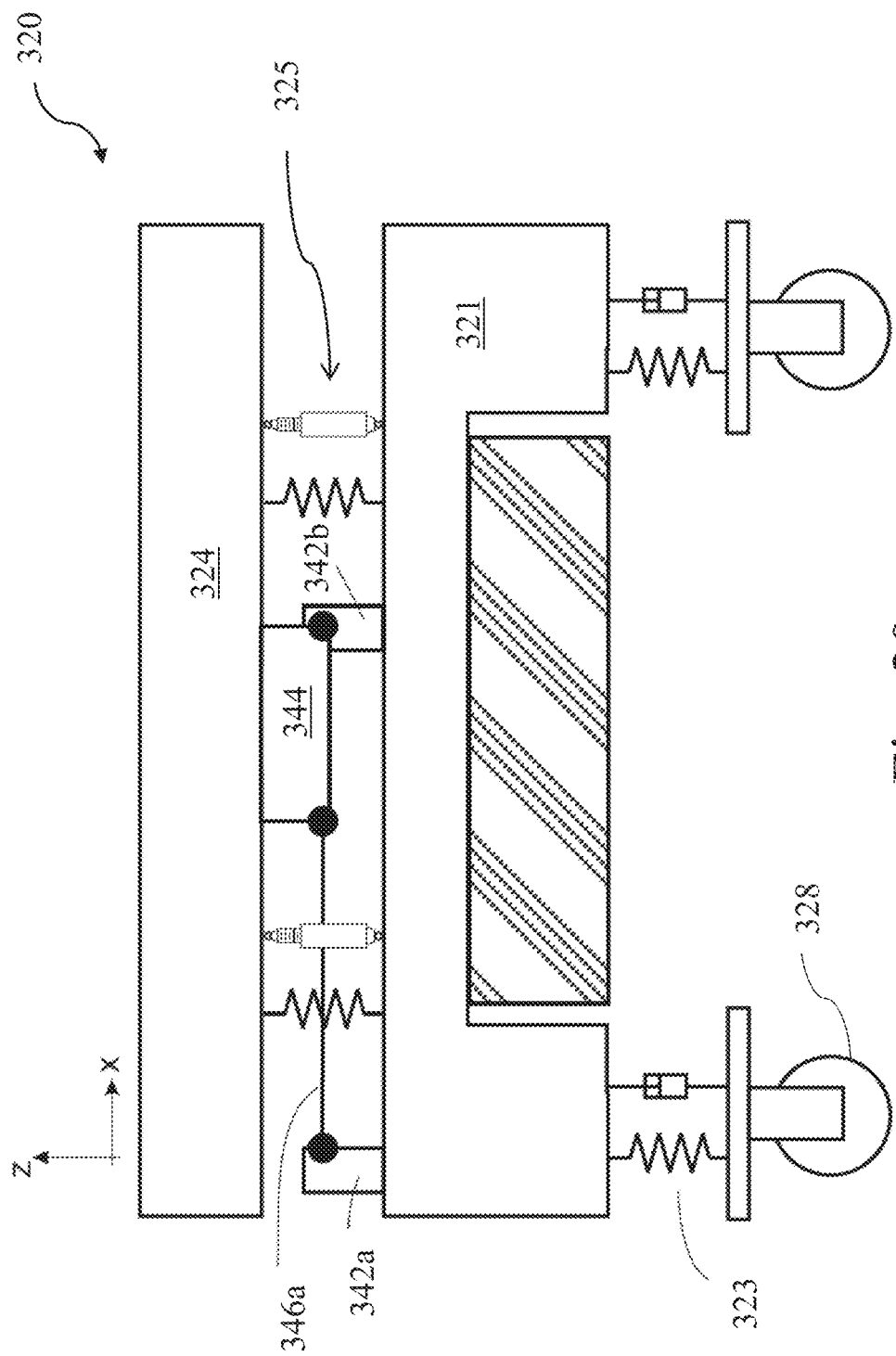
FIG. 20 is a schematic of another embodiment that illustrates that the battery is attached to the chassis and the passenger compartment or the cab floats with respect to the chassis (or undercarriage) in the vertical direction, but is constrained in at least one lateral direction.
Figure 21:
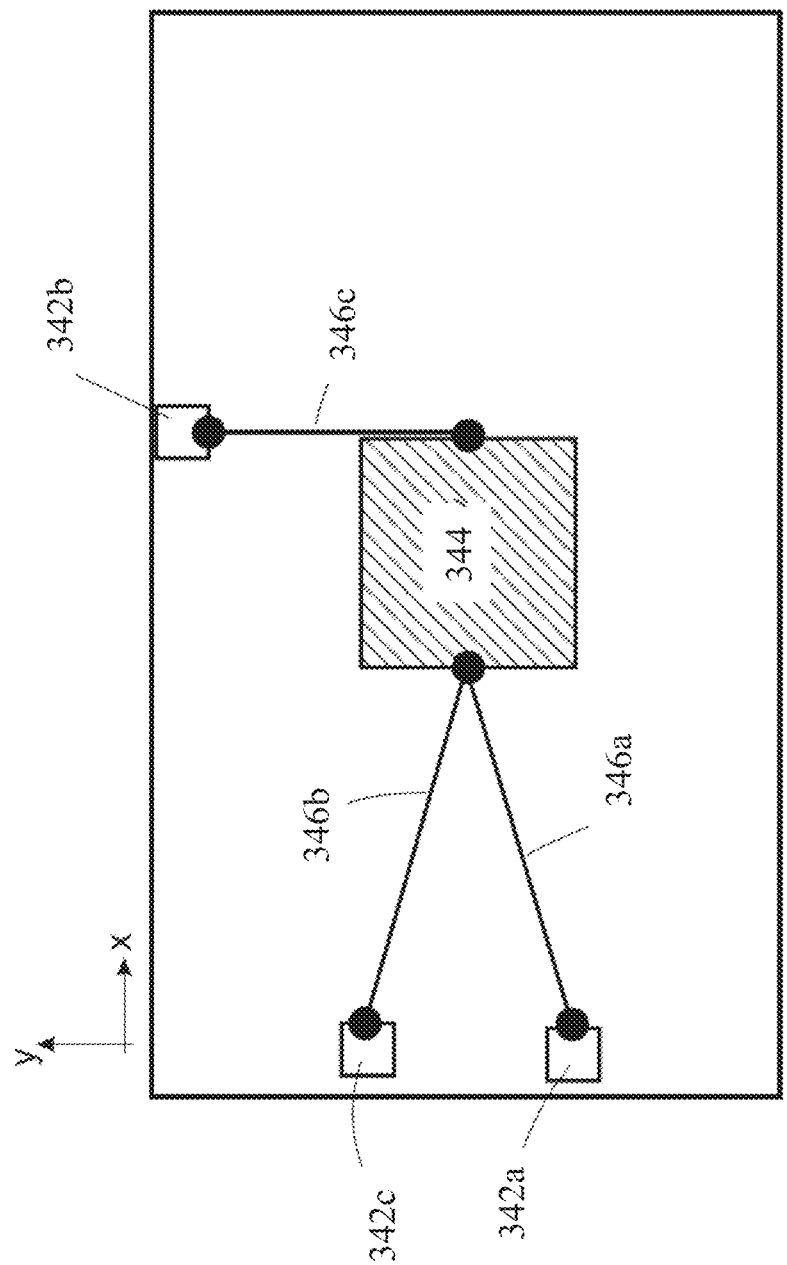
FIG. 21 illustrates the constraining mechanism of the embodiment in FIG. 20.

FIGS. 20 and 21 illustrate another embodiment of vehicle 320 where a chassis (or undercarriage) 321 is supported by primary suspension system 323 and a passenger compartment 324 that is at least partially supported by a corresponding secondary suspension system 325. The depicted embodiment also includes a lateral stability system. However, instead of including a series of posts and cables, one or more ball joint linkages 346a-346c extending between one or more posts 342a-342c associated with the vehicle chassis and the one or more posts 344 associated with the passenger compartment may be used to restrict movement of the passenger cab in in the lateral x and y directions relative to the ground while still allowing movement in the vertical z direction relative to the ground. Depending on the particular embodiment, the ball joint linkages may correspond to rods or other rigid structures extending between ball joints connected to the posts or otherwise attached to the chassis and/or passenger compartment. Further, depending on the embodiment, the ball joints may include some amount of friction to provide a desired response, though it should be understood that the ball joints may be designed to provide any desired performance characteristic as the disclosure is not limited to any particular ball joint design.

Figure 22:
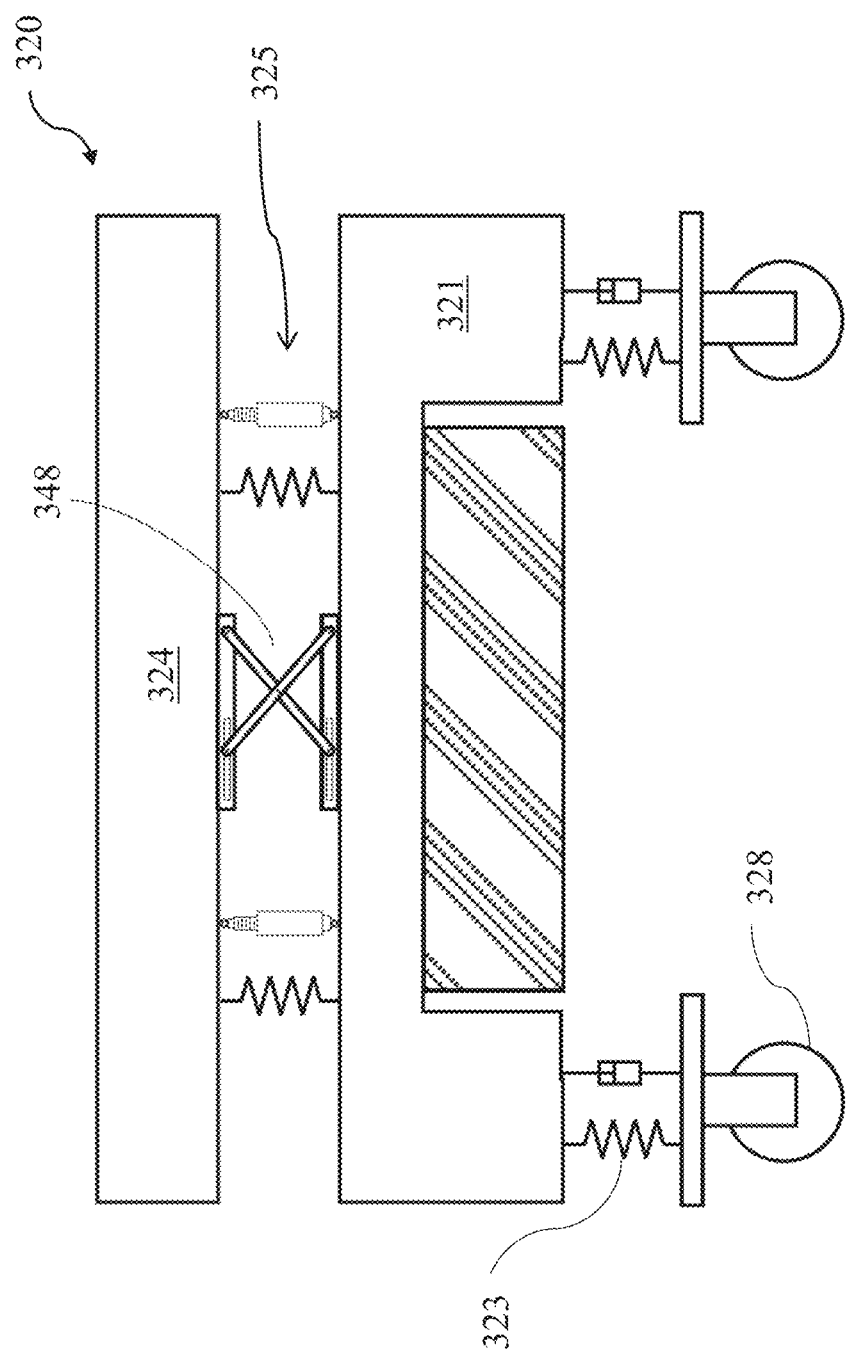
FIG. 22 is a schematic of still another embodiment that illustrates that the battery is attached to the chassis and that the passenger compartment or cab floats with respect to the chassis or undercarriage in the vertical direction, but is constrained in at least one lateral direction.

FIG. 22 depicts yet another embodiment of a vehicle 320 including a primary suspension system 323 located between a vehicle chassis 321 and one or more wheels 328. Additionally, a secondary suspension system 325 may be located between the vehicle chassis and a passenger compartment 324. However, in this particular embodiment, a scissor linkage 348 is also located between, and attached to, the passenger compartment and the vehicle chassis. The scissor linkage permits movement of the passenger in the vertical z direction, but limits, or eliminates, motions in the lateral x and y directions relative to the ground. To facilitate movement in this type of linkage, rubber gaskets or similar material gaskets may be used at each joint.

Again, while the above embodiments have been primarily directed to vehicles including batteries and/or autonomous vehicles, it should be understood that non-electric vehicles including another large mass may also be controlled in a similar manner to the embodiments disclosed above. Additionally, the various control systems and methods described herein may be used with any of an autonomous, a semi-autonomous, and/or a conventionally driven vehicle as the disclosure is not so limited.

Depending on the particular embodiment, the suspension systems described herein may correspond to any number of configurations. For example, in some embodiments, suspension systems may be configured with three or four spring/damper or spring/actuator pairs supporting the corners and/or sides of a platform or structure. Alternatively, for example, six actuators may be configured in a hexapod arrangement and may be used to control the motion of a platform with six degrees of freedom. Different suspension configurations may also be used in the same vehicle. For example, active suspension actuator/spring pairs may be interposed between the vehicle body and each wheel assembly to control the relative motion between the vehicle body and the wheels. In the same vehicle, for example, six active actuators may be arranged in a hexapod arrangement and interposed between the vehicle body and the passenger compartment to control the motion of the passenger compartment relative to the vehicle body. Additionally, in some embodiments, a hexapod system, or other appropriate suspension system, may be used to control the motion of a structure in the passenger compartment as well.

Figure 23:
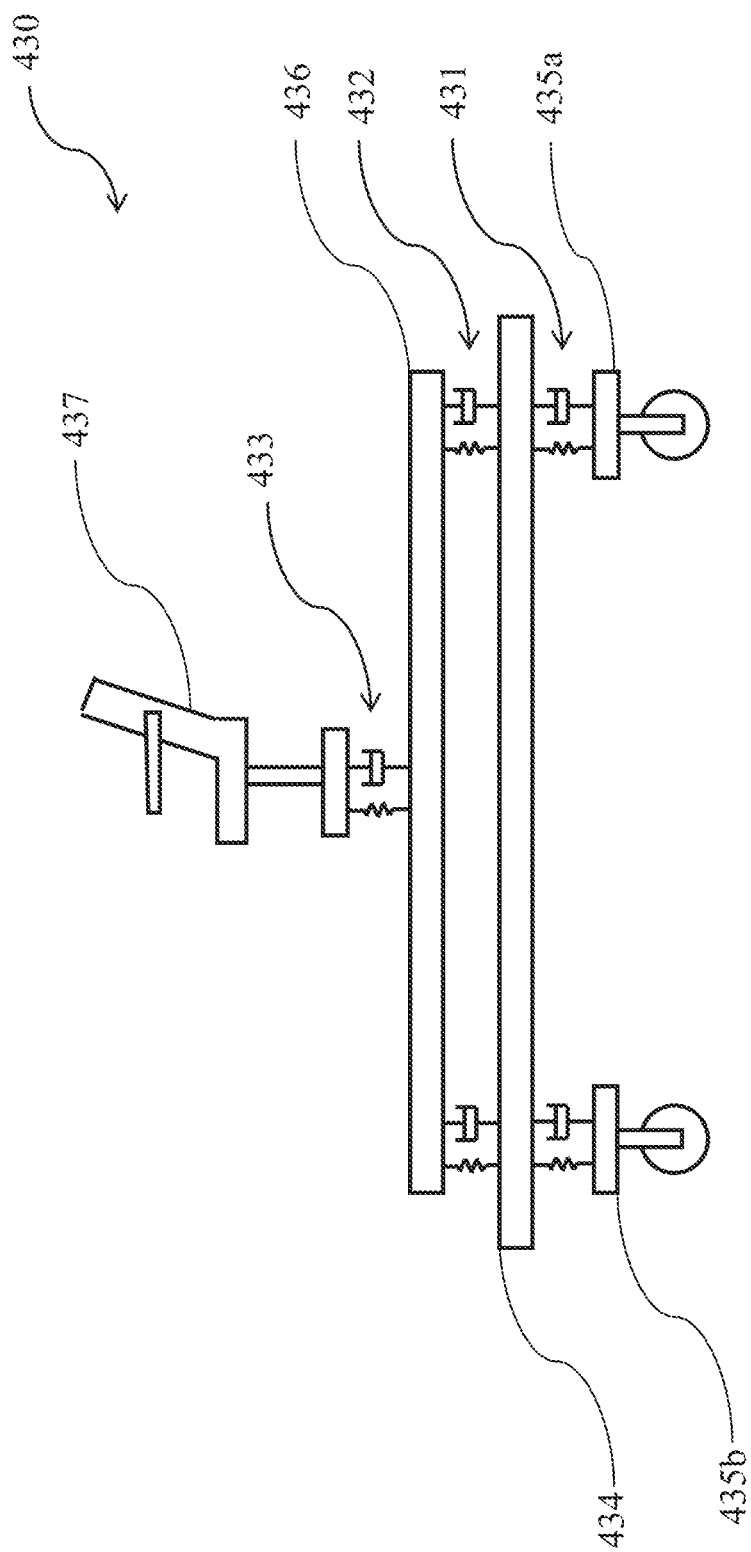
FIG. 23 is schematic representation of an embodiment of a system including multiple suspension systems.

FIG. 23 illustrates a schematic of a vehicle 430 with a first primary suspension system 431 disposed between a chassis 34 and one or more wheel assemblies 435a and 435b of the vehicle. In this particular embodiment, a second and third secondary suspension systems 432 and 433 may also be used to isolate different portions of the vehicle from motions transmitted thereto through the chassis. Specifically, the second suspension system 432 is interposed between the chassis and a passenger compartment and the third suspension system supports a structure 437 which is located within the passenger compartment such as a passenger seat. Again, the various suspension systems may be active, semi-active, passive, and/or appropriate combinations of the forgoing. Also, for active suspensions systems the damper/actuators may be electro-hydraulic, electro-magnetic, electro-mechanical, or any other appropriate type of active system. Additionally, the various suspension systems may be operated in concert or independently as well as either in the same frequency ranges, different frequency ranges, and/or in partially overlapping frequency ranges as the disclosure is not so limited.

FIG. 24 illustrates a hexapod mechanism with six actuators 41a-41f. The hexapod may be used to control the motion of an associated structure that it supports with 6 degrees of freedom. Again, a hexapod mechanism may be used to support, for example, a passenger compartment, a seat, a desk, or any other appropriate structure located within or forming a portion of the vehicle.

FIG. 25 illustrates one embodiment of a structure 450 that includes a seat 451 and/or a work surface 452 supported by dedicated suspension system 453.

In autonomous vehicles, passengers are typically unaware of when the vehicle is going to perform certain maneuvers and even the nature of what those maneuvers will be. For example, passengers of an autonomous vehicle may not know when or in what direction the vehicle is going to turn, when it is going to decelerate or speed up, and when it is going to change lanes. Also, occupants of an autonomous vehicle may be more likely to be facing away from the direction of travel or be occupied with other tasks. These conditions may lead to vehicle occupants feeling disconnected from vehicular motion and driving decisions which may lead to an increased likelihood of motion sickness. Therefore, to reduce the occurrence and/or severity of motion sickness in occupants of a vehicle, it may be desirable to provide one or more cues to one or more vehicle occupants regarding upcoming vehicle maneuvers and/or road conditions. For example, in some embodiments, an autonomous vehicle may be operated to provide various cues or information to passengers about upcoming maneuvers in order to increase occupant comfort. As detailed further below, any number of different cues might be used to communication information to a vehicle occupant including, but not limited to, vehicle pitch, roll, and/or heave. In some embodiments, information about impending or current maneuvers may also be communicated to passengers by other means such as, for example, by providing visual, acoustic, haptic and/or tactile cues. In this way, a passenger may be aware of what to expect before or while the vestibular system reacts to vehicle maneuvers.

In one embodiment, the above noted warnings or cues may be provided whenever the vehicle is operating autonomously or under certain circumstances, such as for example, if it is determined that certain event patterns are present that may be conducive to motion sickness for at least one occupant in the vehicle. These visual, acoustic, haptic and/or tactile cues may be provided using a display in the vehicle, light arrays, sound system speakers, an active suspension system, and/or other devices and modalities. Additionally, as detailed further below, in some instances, displays used for presenting information to the occupants may be controlled to shift a location of images presented on the display to better correspond with movement of a vehicle and/or occupant with the vehicle. This transformation may occur based on accelerometer data from a centralized inertial measurement unit (IMU), sensors from an active suspension system, and/or sensors monitoring movement of an occupant's body and/or their eyes.

In addition to the above, depending on the particular embodiment, passengers may be warned of all vehicle events and/or maneuvers or they may be informed regarding a subset of events and/or maneuvers that may, for example, be expected or predicted to produce discomfort, such as motion sickness, above a predetermined threshold level.

During operation, the overall path (e.g. road choices) that an autonomous and/or a semi-autonomous vehicle will take is typically determined before the vehicle proceeds on the path. This knowledge can be used by a vehicle controller to forewarn vehicle occupants about certain maneuvers which may help to alleviate or reduce the occurrence of motion sickness within the vehicle occupants. In one such embodiment, for example, vehicle occupants may be informed of a direction and/or magnitude of an upcoming turn by, for example, the controller causing the vehicle to gradually "lean into" the turn (i.e. roll toward the center of the turn) a certain distance before the turn begins. However, roll in the opposite direction, away from the center of the turn, may also be utilized. This "lean" may communicate to passengers that the vehicle is about to turn as well as the direction of the turn. The interval by which this cue precedes the turn and the degree to which the vehicle rolls may be set by an occupant or selected by the controller based on the speed of the vehicle and/or the magnitude of the turn based on rules established prior to the turn. Similarly, in a related embodiment, an active suspension system may be used to pitch the vehicle in either a fore or aft direction when anticipating an acceleration or deceleration. For example, a vehicle may be pitched in a fore direction when it experiences a forward acceleration and/or the vehicle may be pitched in an aft direction, i.e. lean back, when anticipating a braking event. Such leaning maneuvers may, for example, be conducted prior to and/or during the control input to the vehicle, and may be sustained or modified over time, and in some embodiments may continue beyond the control input in the vehicle.

While any appropriate time duration and magnitude may be used in the above embodiment, in one embodiment, an anticipatory roll and/or pitch of the vehicle may be between or equal to about 1 to 3 degrees which may be in the direction of an anticipated turn, i.e. positive roll. Further, the anticipatory notice may be given between or equal to about 1 to 3 seconds before the expected event. Of course angles and durations both greater and less than those noted above may also be applied as the disclosure is not so limited.

FIG. 26 illustrates the rear view of an embodiment of an autonomous vehicle under three different conditions. In all three cases the vehicle is moving forward. Vehicle 460a depicts a vehicle with an active suspension system traveling a straight course down a road where no cue is given to a vehicle occupant. Conversely, vehicle 460b illustrates the vehicle active suspension system rolling the vehicle to the right so as to signal to the occupants that a right turn is imminent, while vehicle 460c illustrates the vehicle active suspension system rolling the vehicle to the left so as to signal to the occupants that a left turn is imminent. In some embodiments, vehicle occupants may prefer and/or the vehicle may provide, cues that are opposite in direction to those in FIG. 26. Additionally, other motions, or other types of feedback, may be used to indicate any number of different vehicle maneuvers as the disclosure is not limited in this regard.

As noted previously, in some embodiments, haptic signals, i.e. signals that may be sensed by individuals through their sense of touch, may be at least partially generated by one or more active suspension actuators inducing motion in at least a portion of a vehicle to generate vibrations and/or bumps perceptible to one or more occupants of the vehicle. These haptic warnings may be given in addition to, or instead of, visual and/or acoustic warnings. Additionally, these haptic signals may be more easily perceived in a situation where there is a great deal of ambient noise or a driver is hard of hearing or is otherwise distracted. Therefore, these haptic signals may be used to communicate various types of information to the vehicle occupants and/or driver. For example, during a lane change maneuver, one or more active suspension actuators may be used to introduce vibration of a predetermined constant or variable frequency and/or amplitude to warn a driver that there is an approaching vehicle in the lane being entered. The approaching vehicle may be detected using any appropriate type of sensor including, but not limited to, cameras, radar, LIDAR, ultrasonic, infrared range detectors, or any other appropriate sensor. Additionally, these warnings may be directional. For example, if the driver is moving into a lane to the right of the travel lane and a car is approaching in that lane, one or more actuators on a side of the vehicle directed towards the approaching vehicle (i.e. the right side) may be activated by a controller to introduce the desired vibration to warn the driver of both the approaching vehicle and it's direction.

The frequency and amplitude of a motion induced in a portion of a vehicle may be selected by a controller based on the level of danger involved. For example, if an accident is highly likely if a maneuver, such as a lane change or turn, is completed, the vibration may be more intense, such as having a higher amplitude and/or frequency, than if the danger is not as severe. For example, the frequency and/or amplitude may also be varied depending on, for example, the vehicle speed, relative velocity of approaching vehicle, and/or distance to approaching vehicle. Warnings may also be given under other circumstances when a vehicle is in danger of crashing into an obstruction such as when a vehicle is backing up and/or parking. In such an embodiment, vibrations and/or a bump may be induced by the actuators, for example that are nearest the obstruction. The vibrations and/or bump may be applied with increasing frequency and/or magnitude as the obstruction is approached by the vehicle and/or for larger velocities of the vehicle towards the obstruction. Other circumstances where haptic warning may be given are, for example, when a vehicle is backing out of a driveway. Specifically, the left rear actuator of a vehicle may be activated if there is a car approaching from the left while the right rear actuator may be activated if a vehicle is approaching from the right. In yet another embodiment, the active suspension system may be use to convey a "drowsiness alert" to a driver of a vehicle. This alert may come in the form of a heave, roll, pitch, and/or a combination of these movements. Further, the drowsiness of a driver may be determined through sensors monitoring one or more of erratic steering, acceleration, and/or braking inputs as well as lane drifting of the vehicle. Therefore, once one or more of these monitored quantities exceeds a threshold level, the "drowsiness alert" may be applied to the vehicle using one or more active suspension system. In yet another embodiment, the active suspension system of a vehicle may be used to warn a vehicle operator when the vehicle is overloaded or a load is out of balance as sensed using one or more load sensors associated with the wheels and/or sensors associated with the active suspension system itself.

In some embodiments, vehicle occupants may be informed or warned by, for example, haptic signals or audible signals generated by the active suspension system. For example a virtual rumble strip may be used to simulate physical rumble strips, by causing at least a portion of a vehicle to vibrate at a predetermined frequency under certain situations. Virtual rumble strips may be used, for example, to alert a driver that the vehicle is drifting out of a travel lane. The induced vibration may be at a rate, for example, between or equal to about 30 Hz to 80 Hz with magnitudes between or equal to about 0.1 cm and 0.5 cm though other frequency ranges and magnitudes both greater and less than these ranges may also be used. In some embodiments, the haptic signals may be pulsed, with the length and time between the pulses proportional to vehicle speed. An active suspension system may induce these vibrations by rapidly changing the forces applied to the associated portions of the vehicle such as the wheels and chassis of a vehicle. In some embodiments, when the vehicle is operating in an autonomous or semi-autonomous mode, there may be instances where the vehicle may need to return control to the driver for reasons such as sensor fault data, poor location sensing, conflicting information, undefined situation. In such situations, the active suspension may activate the actuators to create motion to alert the driver, such as for example, toward the front of the vehicle (e.g. a forward pitch, vibrations of the forward actuators, etc.) to guide the driver's attention to the road ahead.

In the above embodiments, different frequencies may be used to convey different information. Additionally, vibrations may be induced in one or more structures in the vehicle or the entire vehicle. For example, individual segments of the vehicle such as the steering wheel or one or more arm rests of an occupant's seat may be made to vibrate with other actuators to provide cues to the occupants of an autonomous vehicle prior to when the vehicle comes to an abrupt stop, makes a turn, or performs another maneuver.

In addition to providing haptic cues to one or more vehicle occupants, in some embodiments, an active suspension system of a vehicle may communicate with a person by implementing certain movements that can be interpreted as gestures by a person outside the vehicle. For example, a detector may be used to read a personal identification device being carried or worn by a person, and/or a facial recognition device may be used to identify a person in the vicinity of the vehicle. The vehicle's response may include, for example, a gesture that resembles kneeling or other welcoming motion. To perform this gesture and communicate the greeting, the active suspension system may be used to adopt a posture where the front corner of the vehicle nearest the person is lowered to simulate a kneeling posture. While such gestures may be used with any vehicle, in embodiments where the vehicle is an autonomous vehicle, such a gesture may be made when picking up a passenger. Additionally, other gestures may be used such a high frequency vibration as a greeting or message that the vehicle is at its destination or needs to be refueled. Movements may also be induced in the vehicle body to direct the attention of one or more occupants to another communication device for additional information such as a display, a telephone with an incoming call or message, and/or any other appropriate device of interest. Additionally, a vehicle gesture may be commanded in a vehicle to help a person find a vehicle in, for example a parking lot. Gestures may also be used to, for example, signal the start of a vehicle (such as an electric vehicle), to identify correct ride sharing vehicle at a pickup point, to confirm a transaction, to confirm if a vehicle fuel tank is full or the battery is charged, to confirm if vehicle tires are, or are not, properly inflated and/or to indicate other safety concerns.

In some embodiments, an autonomous vehicle may be equipped with entry assist. Based on a user profile, communication with a vehicle through wearable technology, vehicle access technology, or other personal identification technology, or by receiving a command from a person inside or outside the vehicle, a vehicle may be placed in an entry assist mode. Entry assist operating mode may include placing the vehicle in a particular position where entry is made easier. For example, if a person intending to enter the vehicle has an injury, or is disabled, the vehicle may be lowered to a height where entry by the person may be less strenuous.

In some embodiments, vehicle sensors such as optical or infrared cameras located within and outside the vehicle may detect gestures of occupants and/or persons located outside of the vehicle as commands or signals. For example, occupants may use certain predetermined and/or prerecorded hand or body gestures to lock or unlock doors. Additionally, in some embodiments, such gestures by recognized persons made be used to also alter various settings in the vehicle. Persons may be recognized as having authorization to make these changes either through facial recognition, an input pass code, a pass code gesture detected by the vehicle, or any appropriate type of identification method and/or device.

In addition to using vehicle gestures for greetings and communicating information, in some embodiments, the active suspension system of a vehicle may be used to induce motion in a vehicle that is at least partially covered with snow in order to clear at least some of the snow from the vehicle. The induced motion may be a rocking or shaking motion at various frequencies in one or more bands ranging from about 1 Hz to 10 Hz, although other frequencies both greater than and less than those noted above may be used as the disclosure is not so limited. This snow removal process may be controlled from outside the vehicle by, for example, means of a key fob or a cell phone application in wireless communication with the vehicle through a blue tooth or a wireless network connection. In some embodiments, the snow clearing routine or algorithm may actuate other vehicle devices such as defrosters and HVAC system when activated in addition to operation of the active suspension system. Depending on the embodiment, the induced motion may include at least one motion type. For example, a routine or algorithm can first turn on defrosters and warm HVAC, then a first low frequency large body motion may be induced, and then a higher frequency smaller amplitude frequency may be induced.

Figure 27A:
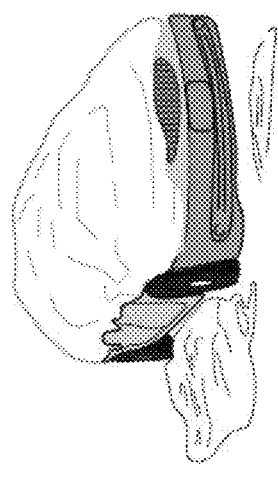
FIGS. 27A-27D are a series of schematics of an active suspension system being used to "shake" off snow from a vehicle.
Figure 27B:
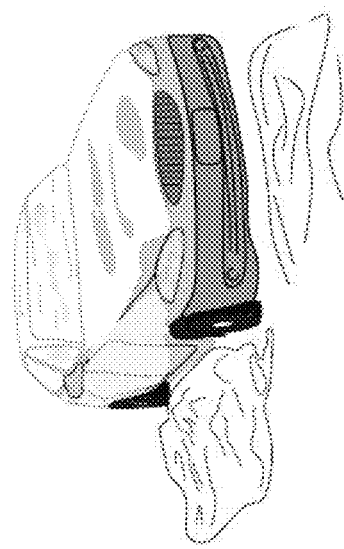
Figure 27C:
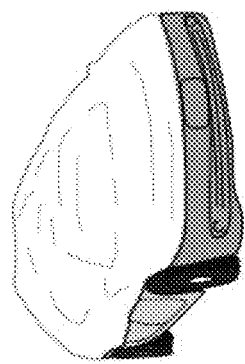
Figure 27D:
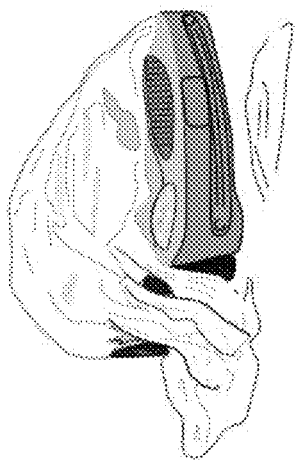

FIGS. 27A-27D illustrate how an active suspension system may be used to "shake" off snow from a vehicle. FIG. 27A shows the vehicle prior to the start of the shaking motion. FIGS. 27B-D illustrate the vehicle with different degrees of snow removal due to shaking and or rocking of the vehicle with the active suspension system during the shaking process. It should be understood that the various movements and gestures noted above may be accomplished by actuating one or more actuators of the active suspension system either together, singly, in succession, or in any other appropriate manner to produce the desired gesture or movement. The gestures may be preprogrammed by the vehicle manufacturer, selected or designed by a vehicle operator using, for example, a user interface. Of course, the use of one or more active suspension systems to communicate information may be in addition to, or instead of, other means of communicating information to a person, inside or outside the vehicle, including a sound source, a light source, and/or a tactile signal generator.

In some embodiments, one or more gestures may be activate by a vehicle occupant and/or driver pressing a button, physical or electronic, in the vehicle. Such a button may be located at any convenient location in the vehicle such as, for example on the dashboard, arm rest, a console, and/or a steering wheel.

In some embodiments, in certain circumstances, a vehicle may assume a posture when activated, either automatically or in response to a signal or command from a vehicle operator, or other authorized person. These circumstances may include for example, when the vehicle is parked and/or locked. The posture assumed in this case may be that suspension system (which may include a height adjustment actuator) lowers the vehicle closer to the ground in order to for example achieve a sporty look. In other embodiments, the vehicle may be raised depending on vehicle operator and/or owner preference.

Figure 28:
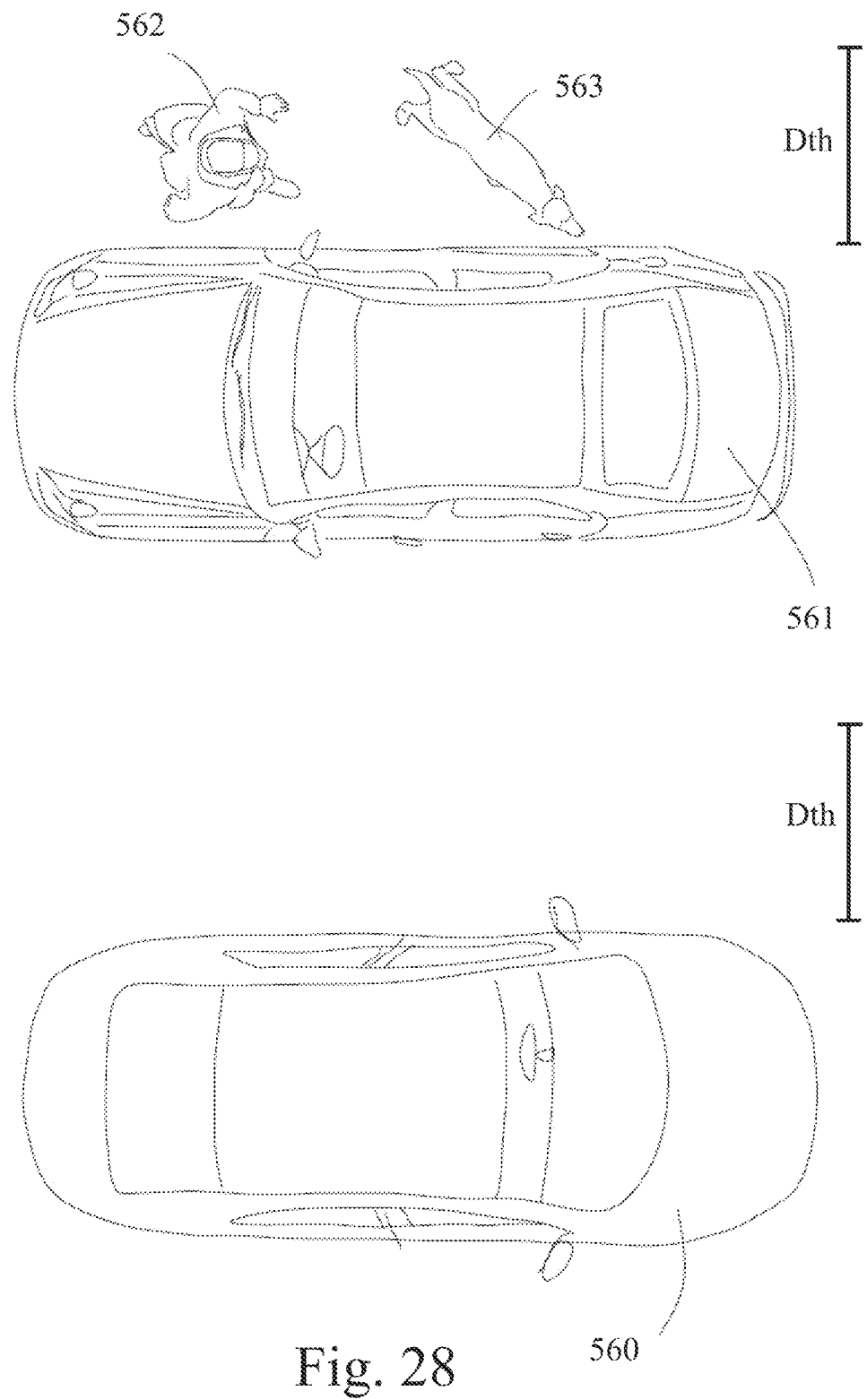
FIG. 28 is a schematic representation of a vehicle, a person, and an animal in close proximity to a vehicle that uses an active suspension system to induce motion in the vehicle body.

In some embodiments, when an active suspension system is used to move the vehicle while it is parked and/or while it is moving, sensors may be used to determine the proximity of people, animals, or stationary objects such as walls or other cars relative to the vehicle. Under circumstances when a person, animal, or object is within a certain threshold distance from the vehicle, the motion induced by the active suspension system may be limited or disabled. FIG. 28 illustrates two vehicles 560 and 561. Various proximity and infrared sensors may be used to detect presence of inanimate objects and people or animals within a certain distance from the vehicle. For example, sensors in vehicle 561 may be used to disable or limit the capability of the active suspension system to induce motion in the vehicle because of the presence of a person 562, a dog 563, and/or the other vehicle being within a threshold distance $D_{th}$. Additionally, in some embodiments, the active suspension system may be prevented from inducing motion in the vehicle if one or more doors and/or one or more windows are open. Alternatively, in another embodiment, the amplitude of the motion induced by the active suspension system may be limited to a preset threshold if one or more doors and/or one or more windows are open.

Figure 29:
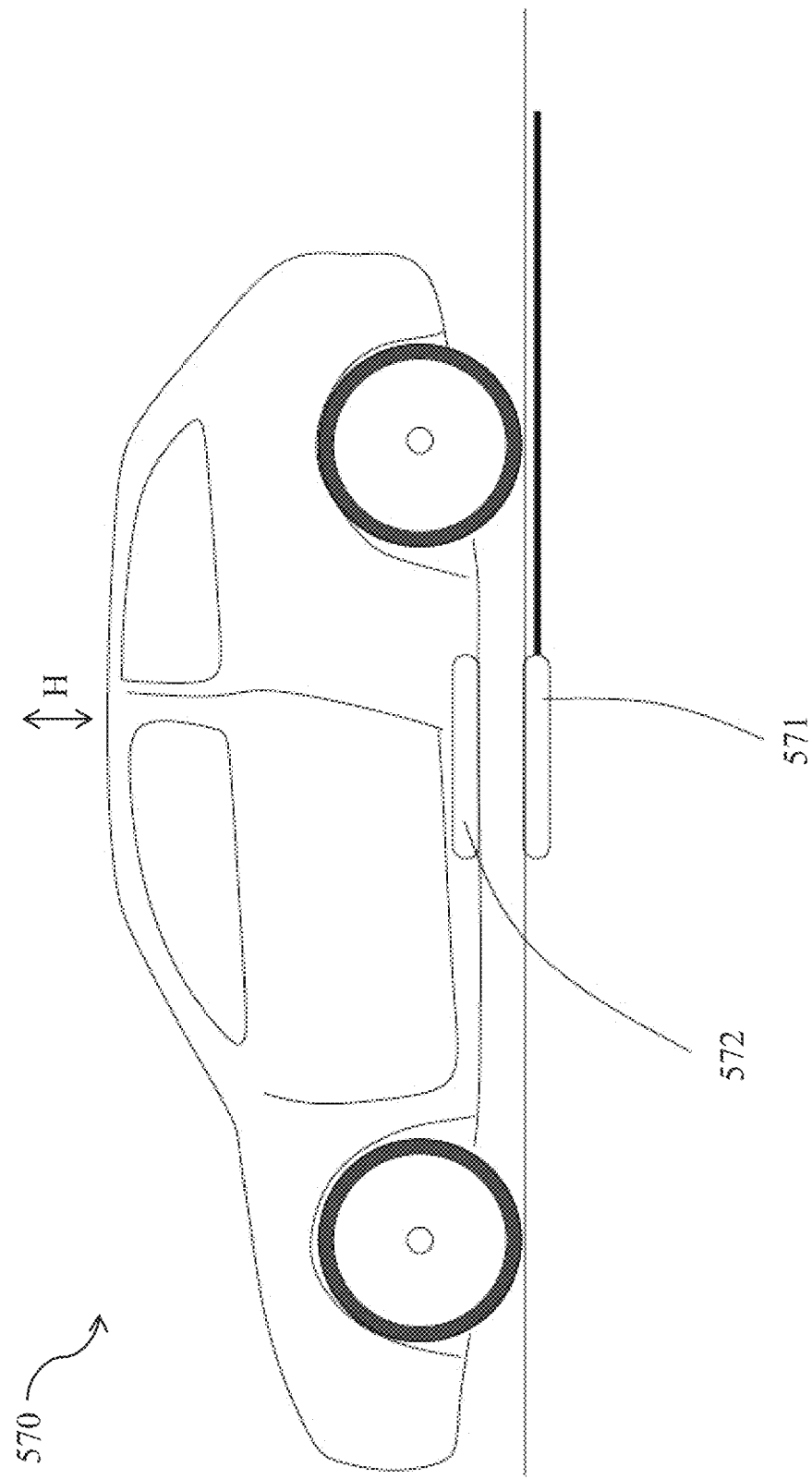
FIG. 29 is a schematic representation of an electric vehicle equipped with inductive recharging coils and an active suspension system.

As described above, an active suspension system may be used to control both movement and positioning of one or more portions of a vehicle. Further, in some embodiments, electric vehicles or other types of vehicles may be equipped with an inductive recharging coil that is mounted, for example, on the undercarriage of the vehicle. During a wireless charging process, this coil receives electrical energy from a primary coil mounted on a road surface or parking space. In response to determining an appropriate proximate primary coil, the vehicle's active suspension system and/or height adjustment system may be used to lower the vehicle from a first height to a second height closer to the ground to bring the coils into closer proximity for a more efficient charging process. FIG. 29 illustrates one embodiment of an electric vehicle 570 equipped with inductive recharging coils. Specifically, coil 571 is embedded in, or disposed on, the road or parking surface, while the secondary coil 572 is attached to the vehicle. An active suspension system and/or vehicle height adjustment system may be used to lower the vehicle to achieve more efficient energy transfer between the coils during charging. Subsequently after charging, the active suspension system and/or vehicle height adjustment system may be used to raise the vehicle to a normal operational height. This selective change in the vehicle height is illustrated by the two sided arrow H in the figure.

Through the use of sensors coupled to one or more vehicle systems, failure or abnormal operation of one or more vehicle systems may be detected and communicated to vehicle occupants, and/or communicated to a remote location. Through the use of pattern recognition related to long term component behavior, the performance of one or more major components may be monitored. For example, if the thermal behavior of a pump within an active suspension system is monitored long term and is observed to operate outside a normal range for at least a threshold time period, it may be flagged as being in a possible fault condition. Error reports may be communicated to the vehicle occupants, for example if a suspension component should be replaced, through in-vehicle notifications or through an error report sent to a mobile device or email. In another embodiment, a controller of the vehicle may transmit an error report to a remotely located server and/or database where it may be stored and/or compared with reports from other vehicles and/or earlier reports from the same vehicle to identify possible failure modes.

In some embodiments, an autonomous vehicle may be configured to store a historical record of the performance and response characteristics of one or more suspension and/or other components, such as for example, an actuator pump. This data may include, for example, the torque generated by the electric motor of an actuator as a function of various vehicle operating conditions and environmental conditions. The collected data may also include, for example, hydraulic motor speed, power produced by an actuator (instantaneous and average), power consumed by an actuator (instantaneous and average), vehicle body acceleration, pressure in the damper, hydraulic oil temperature, steering wheel position, damper position, vehicle position (yaw, etc.), brake pedal position, and wheel speed (linear and angular). Collected data may be in either the time or frequency domain. For example, data collected at a certain point in time may be compared to data collected at an earlier time, to data collected after repairs or component replacement, factory-stored data in a lookup-table, and/or to data collected when the vehicle was new. Data collected at one wheel may also be compared to data collected at one or more other wheels of the vehicle. For example, the data collected at a back wheel may be compared to data collected at a front wheel on the same side of the vehicle after a time offset that is dependent on vehicle speed. For example, after an event and performance metric of the first wheel has been determined, the known distance between the wheels may be used to identify the corresponding time period where the second wheel encountered the same event. The data associated with the identified time period of the second wheel may be compared with the corresponding data from the first wheel. Then, based at least partially on these comparisons, various flags may be set, warning lights illuminated, and/or other warning devices used to inform occupants or repair personnel about possible malfunction or faulty operation. For example, unexpected differences between recorded performance metrics such as differences in applied pressures, force, durations of applied forces, rates of change in applied force, and/or any other appropriate metric may indicate faulty operation of one or both of the portions of the active suspension system associated with the noted wheel assemblies.

In some embodiments, certain components in the system may also be configured to compensate for a poorly performing component. For example, if it is determined that there is increased leakage in a hydraulic pump of an actuator, the system may cause the pump to operate at higher speeds under certain operating conditions to compensate for the leakage in addition to possibly communicating the condition to a vehicle occupant and/or operator using an appropriate indicator light and/or user-interface.

In one embodiment, an active safety suspension system may include multiple active suspension actuators configured to detect a fault condition and/or abnormal operation of one or more of the actuators. Abnormal operation of an actuator may be caused by, for example, loss of partial or total power to the actuator controller, degradation of the actuator itself, communication breakdown between various elements of the system, and/or a sensor malfunction. This abnormal operation may lead to undesirable or unsafe vehicle performance, such as for example, understeering or over-steering. Upon detecting an abnormal operation of an actuator, the active safety suspension system may alter the operating characteristics of one or more other active suspension actuators to compensate for the underperforming unit. For example, if due to the loss of power to one actuator controller, that actuator may then be operated in a mode such that it performs as a semi-active or passive shock absorber. The vehicle controller and/or suspension system controller may subsequently operate one or more of the other actuators in a semi-active or passive operation mode as well.

In one particular embodiment, one or more sensors on a wheel assembly may be used to detect when a wheel is out of balance or out of round. An out of balance wheel is an assembly of all the rotating components in the un-sprung mass including the tire, the wheel, the wheel hub, and the brake rotor, plus smaller but important components such as the fasteners connecting the wheel to the hub, the valve stem and pressure sensor in the tire, wheel speed sensor components, and other appropriate components. The out of balance wheel assembly may be considered out of balance because of the mass distribution in the radial direction from the center of mass is not aligned along the axis of rotation of the wheel assembly, causing uneven centrifugal forces when the wheel is rotating. An out of round wheel is a tire and wheel assembly whose radial distance from the axis of rotation of the wheel assembly is not constant as a function of angular position about its axis of rotation.

As the wheel assembly rotates, its mass moves in a substantially circular path around the axis of rotation. The presence of a mass imbalance causes a corresponding centrifugal force imbalance to appear on the hub. The centrifugal force will have a preferential direction that will appear to rotate with the angular position of the wheel assembly around the axis of rotation. If the vertical component of this force is measured, it will appear to have a strong sinusoidal component synchronized with the angular position of the wheel assembly, thus creating cyclical force with a "once per revolution" or first order harmonic pattern.

Typically for high-end vehicles, wheel assemblies (including the tire) are calibrated using a wheel force balancing machine. This requires the tire to be mounted on a wheel, inserted into a machine that spins the assembly while under load in a way that is similar to the way it is loaded when the vehicle is traveling on the road (thus, loaded with the static force of the vehicle through the tire contact patch and the hub). The machine then measures the force exerted by the wheel assembly on the hub while it rotates, and determines the amount and position of any balancing weights required to correct the imbalance. The technician will then remove the wheel assembly from the machine, and attach counterweights at the location indicated by the machine and in the magnitude indicated. In some cases, it also determines the optimal angular orientation of the tire with respect to the wheel, and the tire will then be dismounted from the wheel by the technician and remounted in a different orientation to minimize the imbalance forces. The same process can be performed while the vehicle is running if the vehicle is equipped with a force-sensing hub assembly.

In some embodiments, an angular position and magnitude of a force imbalance may be determined by using the one or more sensors which may include one or more accelerometers and/or angular position sensors associated with a wheel assembly. The position and size of one or more weights to provide a balanced wheel may be determined by a vehicle control system so that an imbalance may be corrected without having to remove the wheel from a vehicle. If the vehicle is equipped with an active suspension system, the wheel imbalance may also be at least partially corrected by applying a force to the wheel in a direction substantially opposite the cyclical force applied to the vehicle body by the wheel. Therefore, this may counterbalance the cyclical force caused by the imbalance and reduce disturbances input to the vehicle body during operation. In order for the imbalance to be effectively reduced, or eliminated, the actuator of the wheel with the imbalance may apply a similar force directed in an opposing direction to the force generated by the imbalanced wheel during a corresponding time portion for each rotation of the wheel. Accordingly, the frequency and magnitude of the applied force will increase with increasing vehicle speed and correspondingly decrease with decreasing vehicle speed. Further, in some embodiments, a phase locked loop (PLL) may be used to properly time the application of the actuator force to reduce or cancel the centrifugal force due to the wheel imbalance. Using a wheel angular position sensor, such as for example an anti-lock braking sensor, and a model of the wheel assembly as a mass on a spring, the cyclical nature of the imbalance force in one specific direction (for example, the vertical direction as measured by a motion sensor oriented in the vertical direction, or any direction as measured by a force-sensing hub assembly) may be determined and thus the underlying imbalance force vector's magnitude and angular position as it rotates may be calculated. Using a PLL, the calculated imbalance force's angular position (or "phase") may be determined and averaged. Each of these will be heavily influenced by motion induced by the road, but will average out to a value that will be detectable if the imbalance force is of significant enough amplitude to rise above the normal noise floor of the signal. In some embodiments imbalance in the wheel force can also be cause by an imperfection in the tire construction.

An out of round wheel will typically show a pattern of motion that appears more like a cyclical road imperfection, and as such has a different character from an imbalanced wheel. In many cases, an out of round wheel may cause cyclical forces that have higher order harmonic content rather than just first order harmonics. This may enable a detection algorithm to monitor the forces on a wheel assembly to detect an out of round behavior, and treat it differently from a force imbalance.

In some embodiments an active suspension system may be used to diagnose an imbalance or out of round condition on each tire without having to remove tires from the vehicle and create a force to at least partially and/or temporarily compensate for the imbalance and/or an out of round wheel. This allows the vehicle to remain in operation, at least temporarily, without the normal discomfort and/or tire damage associated with imbalanced wheel assemblies, but at the same time the system may diagnose the condition and warn vehicle operator to request service at the next convenient time. In some embodiments, upon detection of a wheel imbalance and/or an out of round wheel, the system may indicate the condition to a vehicle operator using an indicator, a signal, or any other appropriate output observable to the operator. Additionally, the system may determine and output appropriate remedial actions to take for the particular wheel to competent service personnel. For example, data may be output to a hooked up diagnostic system and/or may be transmitted to a display viewable by the service personnel. The transmitted data may include various parameters including, for example, what magnitude and/or angular position of counter weights may be used to remedy a wheel imbalance. The typical process of having to unmount and rebalance wheels may thus be avoided, and the process of rebalancing one or more vehicle wheels may be achieved more quickly and at lower cost. It should also be noted that the simple fact of cancelling the imbalance through the use of an active suspension force also automatically diagnoses the position and magnitude of one or more counterweights.

In some embodiments, an autonomous vehicle equipped with an active suspension system may self-diagnose malfunctions and/or abnormal operation of one or more actuators by inducing one or more predetermined excitation motions to one or more portions of a vehicle. The active suspension system and/or one or more sensors may then monitor the resulting response in the vehicle and/or one or more subsystems. Based on this information the system may make a fault determination. In some embodiments, if such a fault determination is made, the system may: notify occupants and/or operators using an indicator, display, and/or user interface; schedule a repair appointment with a repair facility; and/or remove the vehicle from service.

In one embodiment, the active suspension can continuously monitor the system's response transfer function without even inducing any additional motion other than what is being induced as part of the normal operation of the system. A system model may track the behavior of the actuator and all of its sensors, for example using a Kalman filter to estimate the system parameters and track their changes with time and environmental factors.

In another embodiment, the active suspension may be used to induce a motion that is too small to be detected by the occupants in the vehicle, but large enough to be detected by at least one or more sensors of a system. The resulting motion may then be compared to a target motion. Taking into account all the other conditions present in the vehicle and actuator at the time, i.e. actuator performance, vehicle load, load distribution, temperature, and other appropriate parameters, the data from one or more sensors may be used to diagnose and/or predict possible system faults. For example, in some embodiments the active suspension system may be used to create a relatively high frequency motion, for example at 40 Hz, every time a particular event happens, after predetermined time intervals, and/or after a request is received. For example, in one embodiment when a vehicle comes to a full stop a motion may be excited in the vehicle using an active suspension system. Under these conditions, and taking the system operating parameters into account, the motion detected by one or multiple sensors may be compared to the target or expected motion. One or more discrepancies between the expected and actual output of one or more sensors may be used as a fault indicator or operation of at least a portion of the vehicle beyond acceptable tolerances. In some embodiments this information may be used as a prognostics tool.

Alternatively or additionally, in some embodiments, the active suspension may be used in a diagnostic mode to move the suspension through its full range of motion. This can be achieved even with an active suspension of limited force capability by identifying the resonant frequency of the suspension. In a first step, a pattern of motion may be created. This may for example be a motion of only the front of the vehicle, or a motion of only the rear of the vehicle, or a motion in the roll direction, or any other combination of motion. Then in a second step this motion may be induced at a frequency below the expected resonance of the system and at a small amplitude, and to measure the resulting motion by using one or more sensors present in the system. For example, one or more suspension position sensors may be used for this purpose. Then in a third step the frequency may be gradually increased to determine the frequency at which the motion is the greatest. This frequency may be close to the resonant frequency of the system for that specific pattern of motion, and may be entirely determined by the system mass distribution and the compliances involved in this motion. In a passenger vehicle, this may be determined by the main suspension springs, roll bars, and the vehicle's mass distribution. This may be used to determine any significant changes in spring behavior and thus to diagnose the components, as long as the mass distribution is known (for example, if the vehicle is empty and the amount of fuel in the gas tank is known). The system may then be moved in the given pattern at the frequency resulting in the highest output motion. The amplitude of excitation may then be gradually increased until the output no longer changes. This will indicate the full range of motion of the vehicle, and can be used to detect any mechanical interferences, and any inconsistencies in the motion pattern that could be the result of sensor and/or actuator malfunction. This can then be repeated for multiple patterns, to isolate functional problems to a single source of interference or malfunction.

In some embodiments, an active suspension may be used to actuate a vehicle to excite other sensors in the vehicle. For example, the central vehicle inertial measurement unit (IMU) that is present in many vehicles can be calibrated and validated by using a known motion condition (such as for example a predetermined motion while the vehicle is standing still) and comparing the resulting sensor signal to the signals from other sensors that correlate with this motion under those conditions. For example, when the vehicle is standing still (and thus there is no input from the road or the driver), the motion sensed by the suspension position sensor should closely correlate with motion sensed on the vehicle body (at the IMU, or at any other acceleration sensors or position sensors on the body). The motions detected by the suspension position sensors and body acceleration sensors may also correlate with each other in a way that is consistent with their mounting location and orientation on the vehicle. This allows for example to detect any change in orientation of a given sensor, or any change in its mounting.

In some embodiments the above methods may be applied to autonomous vehicle sensors. In one embodiment, the vehicle could test its LIDAR, RADAR, LASER, and other position sensors while parked in a garage or near an obstacle. Moving the vehicle using the active suspension actuators would allow the vehicle to calculate an expected signal change from an outward looking sensor that detects an obstacle. If the change in the signal is inconsistent with the motion of the vehicle, a malfunction of the sensor may be detected. This is especially true if the malfunction is persistent, and if the sensor system is redundant enough to be able to eliminate any other causes of the inconsistency. For example, a LIDAR system could be correlated with a vision-based system such as a camera. When moving the vehicle in a known manner, the two sensors may show a relative motion of a detected obstacle that is consistent with each other. This test could be run in a controlled setting, for example at a repair shop with a given lighting and a given obstacle at a specified distance, but it could also be run on a regular basis when the vehicle is parked in a safe location, with the proper caveats for ruling out "false positive" fault detection when the test validity is uncertain. In some embodiments, the test result could for example be used to set an internal warning flag, and if this warning flag persists through multiple tests under multiple different conditions, then it can be used to raise a flag for the vehicle to be tested at a certified repair shop.

In some embodiments, energy needs for the active suspension system, taking into account regeneration, may be predicted along with available energy level, both of which may be used to determine an optimized ride quality that can be delivered on a given road for a particular trip.

In some embodiments, a vehicle equipped with an active suspension system may project electrical power needs of the system based on a planned route. Power needs may be calculated based on, for example, the topography, road surface conditions, distance, elevation changes, historical data collected by the vehicle itself and/or by one or more other vehicles, comfort and/or performance requirements that are in effect, and auxiliary power requirements, such as for example HVAC based on known external temperatures and a desired internal cabin temperature. Based on this information, the vehicle may allocate available energy for the route ahead based on the projected energy needs and/or instantaneous power requirements for some or the remainder of the trip. The projection may also take into account opportunities to refuel/recharge the vehicle. In some embodiments, the vehicle may communicate with a refueling/recharging station to reserve a refueling/recharging slot timed for the anticipated arrival of the vehicle. Additionally, the vehicle may use a password or other unique identification means, that may be assigned by the recharging/refueling facility, to gain access to the station upon arrival. In some instances, the refueling/recharging station may include a station where at least a portion of the battery pack is replaced or supplemented.

In some embodiments, a trip energy usage plan may be developed that accounts for the tradeoff between various parameters, such as, for example, speed, route and lane selection, traffic conditions, available on-board energy, refueling/recharging opportunities, energy regeneration potential of the suspension or braking systems, comfort settings, and motion sickness avoidance requirements.

In some embodiments, a selection of routes based on such criteria may be presented to vehicle occupants so they may choose. The vehicle or occupants may opt to take a route that conserves the most energy. For example, an energy conserving route would constitute selecting a route based, at least partially, on the amount of energy required by the active suspension system to prevent occupant discomfort or to compensate for road conditions as well as the expected energy consumption for driving a vehicle through that route. The energy requirements needed for a particular driving route may be calculated in any number of ways using parameters such as expected vehicle speed, travel distance, elevation changes along the route, road conditions, energy requirements for operating a suspension system of the vehicle along the expected road conditions in one or more operating modes, as well as any other appropriate parameter. Similar to the above noted embodiments, this information may either be stored locally on the vehicle or may be wirelessly transmitted to the vehicle from a remotely located server and/or database for subsequent use in estimating the desired information. During range-critical trips (e.g. trips involving additional charging stops) and/or time-sensitive trip deadlines, energy rationing may be implemented on one or more a vehicle's system to reduce energy consumption and ensure sufficient energy is available for a desired trip, or portion of a trip. For example, in instances where there is insufficient energy to complete a trip while providing full motion sickness suppression, the vehicle may be operated in a mode where the suspension system provides a reduced motion sickness mitigation mode. In another embodiment, if an autonomous vehicle is travelling empty, for example while the vehicle is on the way to pick up a load and/or passengers, the vehicle may relax or disable suspension control algorithms intended to increase passenger comfort in order to conserve energy.

In conventionally driven vehicles, active suspension actuators may be used to improve road feel and steering response for the driver, as well as to improve comfort for all occupants. Frequently, these two sets of demands are in conflict. Specifically, performance characteristics of suspension systems that make the vehicle more responsive and enjoyable to drive often conflict with requirements that provide a comfortable ride for passengers. For example, suppressing road induced motion in a vehicle at low frequencies, such as frequencies below 1 Hz, may increase passenger comfort by, for example, reducing the likelihood of the occurrence of motion sickness. However, in conventionally driven vehicles, if the vehicle does not respond to road input at these low frequencies, the vehicle's steering may appear disconnected from the road. This behavior may be quite disturbing for a driver. In certain embodiments where a vehicle may periodically be driven but sometimes operated autonomously, low frequencies, such as less than 1 Hz or less than 0.5 Hz, may be suppressed to a greater degree in an autonomous mode than when the vehicle is operated in a conventionally driven mode.

In one embodiment, an autonomous vehicle includes an active suspension system that includes at least one actuator and a vehicle control system that operates the vehicle in an autonomous state and in a conventionally driven state. In the autonomous state, the active suspension system may be operated in a first mode where the active suspension system may not give as much weighting to road feel and drivability requirements and may focus instead on increased passenger comfort and passenger experience. When the vehicle is operated in the conventionally driven state the active suspension system may be operated in a second mode where the active suspension system may provide the driver with a desired level of road feel and drivability. In addition to the above, in the first mode the transmissibility of road disturbances between a road and a structure in the vehicle is less than the transmissibility of road disturbances between the road and the structure for a first frequency range associated with motion sickness such as between 0.05 Hz and 10 Hz.

In another embodiment, an autonomous vehicle, may selectively operate in an autonomous state and a conventionally driven state. The autonomous vehicle may include both a first structure and a second structure which may correspond to one or more different portions of the vehicle. The relative motion between the first structure and the wheels may be controlled by a first suspension system. Similarly, the relative motion between the first and second structures may controlled by a second suspension system. In some embodiments, one or more of the first and the second suspension systems may be active suspension systems.

Vehicles may be exclusively conventionally driven vehicles, autonomous vehicles or multi-modal vehicles. Multi-modal vehicles may selectively operate as conventionally driven (with a driver) vehicles in certain modes and as autonomous vehicles in other modes. Some vehicles may operate as primarily conventionally driven vehicles with various degrees of driver assist or as primarily autonomous vehicles with various degrees of driver intervention.

In embodiments, an electronically controlled suspension on a vehicle has different operating modes for human drive and autonomous operation, wherein the vehicle may switch between suspension operation modes when the vehicle switches between human driver and autonomous operation. In embodiments, an occupant in the vehicle may select between human driver and autonomous operation, and the vehicle may alter the control mode of the electronic suspension automatically. In embodiments, the electronic suspension may be either a semi-active suspension or a fully-active suspension. In embodiments, operating modes may comprise of different algorithms, different parameter settings, and/or other modifications to the control system for the electronic suspension. For example, an active suspension system may reduce motion transferred to at least one portion of the vehicle from road disturbances to a greater degree in one or more frequency ranges, such as those associated with motion sickness, when operated in an autonomous driving mode then when the vehicle is operated in a conventionally driven mode.

In some embodiments, when an autonomous vehicle is operated in a conventionally driven mode, the active suspension system may maintain a negative to zero vehicle roll during some or all turns. Negative roll is defined as a roll away from the center of rotation that normally occurs in conventional vehicles as a result of centrifugal forces. Positive roll is defined as a roll in the opposite direction, i.e. into a turn and towards the center of the turn. A negative to zero roll is typically preferred by drivers of a vehicle. However, in an autonomous mode, passengers may prefer a positive roll in some or all turns. Therefore, during autonomous operation, an active suspension system may maintain the vehicle body in a zero to positive roll. This switch between the two modes may occur, for example, automatically as a result of sensory input indicative of the switch from conventionally driven to autonomous operation, or as a result of a command or signal from a vehicle operator or occupant.

In addition to the above, the inventors have appreciated that eye movement caused by a person's visual ocular reflex (VOR) may lead to motion sickness when an occupant of a vehicle in motion is reading or focused on an image or object in a vehicle. This may be caused by disparity between the shift in the focal point of a reader's eyes as a result of VOR and the actual position of the text, image or object that is being focused on. The VOR adjusts the focal point based on the assumption that the object being focused on, such as a computer screen, or other display, is inertially fixed. However, in a moving car, this is typically not true. Therefore, in one embodiment, an image on display within a vehicle may be moved in a manner that at least partially negates the retinal slip occurring in the eyes of a vehicle occupant who is reading from, or watching a video on, the display.

In some embodiments, this conflict between the position of an image on a display and the changes in an occupant's focal point due to VOR may be alleviated by reducing the movement of a vehicle body in the frequency range between 1 Hz and 10 Hz. Additionally or alternatively, the movement of a one or more sub-portions of a vehicle and/or a passenger compartment of the vehicle may be mitigated in this frequency range as well. For example, a seat, a desk, and/or work surface may include a suspension system that mitigates motions of these structures within this frequency range.

Figure 30:
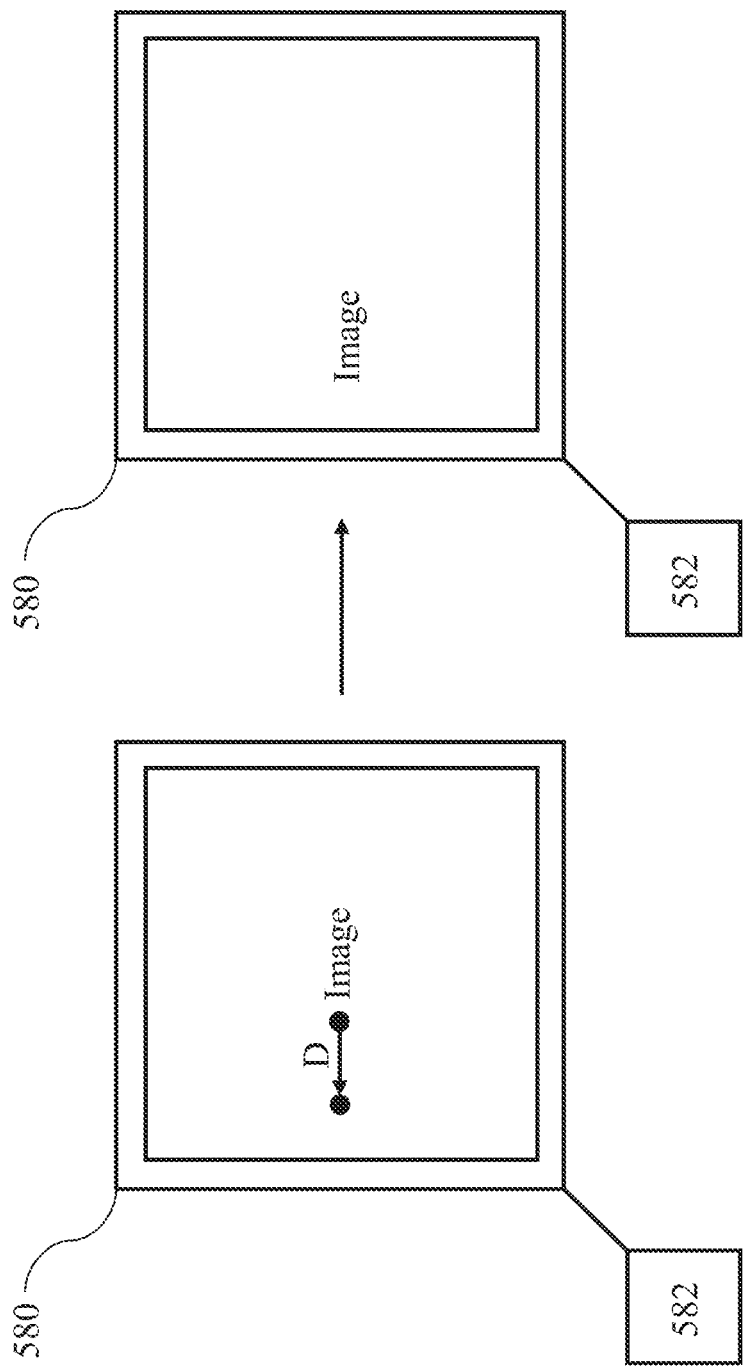
FIG. 30 is a schematic representation of a display moving an image to compensate image position for an occupant's visual ocular reflex.

In addition to the above, and as shown in FIG. 30, in one embodiment, an image on a display 580, such as on a computer or interface screen, may be moved by a distance D to at least partially compensate for an expected VOR of an occupant which may help to mitigate the likelihood of motion sickness in the occupant. For example, a display controller 582 may determine the amount of movement D anticipated for an occupants focal point at a given frequency due to the expected VOR of a vehicle occupant by, for example, using a transfer function between head movement and vehicle movement that may be either empirically or statistically determined.

The movement of the image may also be determined by, for example, determining a transfer function between the imaged movement in the inertial space and the movement of the vehicle. The system creating the image may then be used to induce motion in the image that compensates for the disparity in the anticipated position of the image as a result of the VOR and motion induced by the vehicle. For example, in the case of text on a computer screen, the image may be moved to mitigate the disparity between the anticipated and actual position of the text within a particular frequency range.

Due to an occupant's vision typically being able to compensate for movements below about 1 Hz, in some embodiments, an image displayed on a display may only be moved to compensate for motions with a frequency range between or equal to about 1 Hz and 10 Hz, 2 Hz and 10 Hz, or any other appropriate frequency range including ranges both greater than and less than those noted above as the disclosure is not so limited.

In some embodiments, a synthesized image may be projected within the interior of a vehicle and made visible to occupants to provide a reference point that may minimize discomfort, such as, motion sickness or disorientation. For example, a synthesized image or reference frame may be a realistic looking image displayed to vehicle occupants to alter occupant perception of external surroundings and vehicle motion. For example, a synthesized horizon may be projected onto a surface or display within the vehicle. The horizon projected onto, or otherwise displayed on, a surface may be moved relative to the surface to track actual movements of the car and provide a reference of movement to occupants within the vehicle.

In some embodiments, a trip summary may be provided via a smart phone app to show benefits of an active suspension system. In some embodiments items that may be included in the trip summary are for example: total suspension travel, driver aggressiveness, road roughness profile, route driven on a map display, energy In some embodiments, a map may display road roughness on the recent trip. In some embodiments, the benefits of using an active suspension system on the recorded route may be calculated and displayed by the system. The benefits may be calculated, for example, by using the weighting factors described in in ISO standard 2631-1 published in 1997.

In yet another embodiment, sensors may be used to detect an imminent or possible crash or accident. This may be done by comparing the projected trajectories of the vehicle as well as surrounding objects, obstructions, and/or other vehicles. If there is a sufficiently high likelihood such as a percentage probability greater than a threshold percentage, actions may be taken to prepare the vehicle and occupants for a crash in order to mitigate the effect of such an occurrence on vehicle occupants. For example, seats may be repositioned relative to the identified or expected impact vectors and the locations of in-vehicle airbags. Certain airbags and safety devices may be armed and/or deployed, while others that are not properly aligned with one or more occupants may be disabled to avoid unnecessary deployment or unwanted deployment. For example, an airbag adjacent to an unoccupied seat and/or an airbag that an occupant is improperly oriented towards may be disabled. In some embodiments, vehicle airbags may be deployed pre-crash so that force and velocity of deployment may be reduced relative to airbags that are deployed after a vehicle starts decelerating after contact is made in a crash. The timing of deployment may be determined using the expected time of the crash determined using the intersecting travel vectors as well as a time for deploying the one or more airbags.

In some embodiments, each occupied seat within the vehicle, depending on its position, may orient, secure and lock in a way that minimizes the effects of an impact upon the occupants. For example, the seats may be oriented towards and locked in the closest forward or rearward facing direction relative to the vehicles direction of travel. Sharp objects or hard surfaces may be retracted and/or airbags or other safety devices may be repositioned. Therefore, in the event that vehicle sensors detect that a crash or accident is imminent, one or more components that could come into contact with a vehicle occupant may be placed in an accident mode. In such an operation mode, such components may be retracted or moved out of the way to avoid injury. The rate and/or degree of deployment of safety devices such as, for example, air bags, may also be adjusted to account for the severity of the anticipated impact.

In some embodiments, if vehicle sensors detect that a crash or accident is imminent, occupants may also be notified to brace for impact or to assume a particular position or to fasten seatbelts. Occupants may be made aware of such procedures at the beginning of a ride or when a new passenger enters the vehicle. The methods by which occupants can brace themselves for an impact that will provide the best chance of promoting passenger safety may be explained automatically to any new occupant by means of a video presentation. Such instruction may be disabled if the system recognizes that all passengers have already received instruction or if requested to do so by one or more occupants. If a systems detects the presence of a child seat or young children in the vehicle, special instructions may be given. The system may also test if a child seat is properly secured and notify occupants if an unsafe condition exists.

Figure 31:
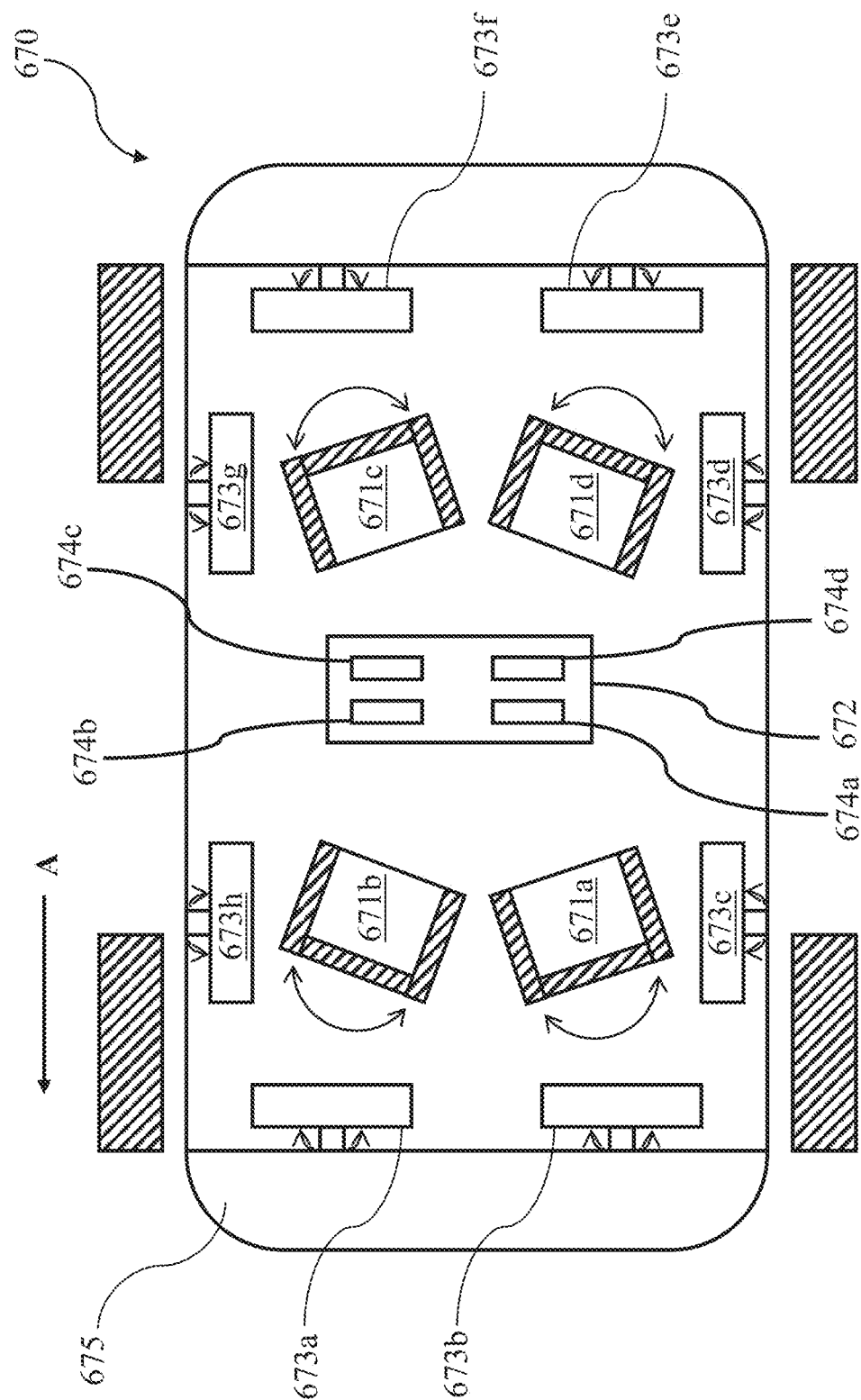
FIG. 31 is a schematic representation of an embodiment of a vehicle preparing for an imminent crash.

FIG. 31 illustrates one embodiment an autonomous vehicle 670 that implements the above noted methods and features. In the embodiment, the vehicle includes four passenger seats 671a-671d, a work surface 672, air bags 673a-673h and work surface embedded air bags 674a-674d. If the vehicle is moving in a direction A and is about to collide with an object, the autonomous vehicle system may align the seats so that they are facing in the closest forward or backward direction and lock them into position before the collision. Alternatively, if there is sufficient time, the seats may be adjusted to the most advantageous position for effect of the impact vector, e.g. the seats may be oriented towards or away from the expected motion from the crash. Simultaneously certain airbags may be armed to deploy and certain air bags may be disabled. For example if seats 671a and 671c are occupied and positioned as shown, only airbag 674d would be armed and the remaining airbags may be disarmed.

In addition to using active suspension systems to mitigate motion sickness during vehicle operation, the inventors have recognized that one or more active suspension systems located within an operational road vehicle may also be used to create a more realistic environment for a multimedia experience depicted on a display integrated with, located within, and/or displayed adjacent to the vehicle. For example, such a method may be used for playing video games, observing movies, and/or enhancing a video reality experience.

In one embodiment, a vehicle, equipped with one or more sensors, may be used to record road-induced effects in a vehicle. These recorded effects may include, for example, wheel (unsprung mass) motions and/or vehicle body (sprung mass) motions which may include roll, pitch and/or heave. The recorded information may include relative displacement between one or more wheels or wheel assemblies and one or more points on the vehicle body. The recorded effects may include velocity and/or acceleration of one or more points on the vehicle and/or a wheel assembly. The vehicle used for collecting the data may be equipped with, for example, a passive suspension system, a semi-active suspension system, or an active suspension system. Road-induced effects may include any displacement, velocity or acceleration experienced by a vehicle body (sprung mass) or wheel assembly (unsprung mass) as a result of traveling on a road or other driving surface.

A different vehicle equipped with an active suspension system may subsequently be used to at least partially replicate the recorded driving-induced effects while the vehicle is parked or stopped either indoors or outdoors. For example, the active suspension system of a parked vehicle may induce motion in one or more portions of a vehicle body to simulate the motion previously recorded by the same vehicle or by another vehicle while traveling on a road or other surface. In some instances, the motion of the parked vehicle may be modified by mitigating some recorded road-induced effects or by artificially adding to them.

Various pre-recorded road-induced effects, such as for example, vehicle roll, pitch and/or heave may be replicated by using an active suspension system. Such replication may be considered "playback" of the pre-recorded road-induced effects. Additionally or alternatively, pre-recorded road-induced accelerations such as fore-aft and lateral accelerations may be replicated by using platforms or other support mechanisms that may support and move the vehicle in those directions. Within the constraints of the active suspension, the active suspension may also induce the sensation of certain lateral and fore/aft accelerations by pitching or rolling the vehicle. During this process, the road-induced effects may be replicated in a parked or stopped vehicle to match the pre-recorded effects.

In some embodiments, the active suspension system may duplicate the recorded roll, pitch and/or heave precisely. In some embodiments, precise replication may mean replication of a pre-recorded road-induced quantity, such as for example, vehicle body or wheel: displacement, velocity, acceleration, or jerk, or vehicle: roll, pitch, heave, roll rate, pitch rate, roll acceleration, pitch acceleration, with an error range of less than or equal to about 1%, 5%, 10%, or any other appropriate percentage of the recorded motion.

In some embodiments, displacement or force that would need to be applied by one or more of the active suspension actuators in order to replicate certain pre-recorded effects may be beyond the capability of one or more components of the active suspension system. It also may be determined that the degree of replication of road-induced motion should be limited for other reasons as well. In such cases, the pre-recorded data may be pre-filtered to limit actuator motion or force commands to be within predefined threshold limits. For example in some embodiments, the maximum active force and/or the maximum displacement command sent to an actuator controller may be limited to a desired threshold in compression and/or extension. Therefore, in some embodiments, where the pre-recorded data is pre-filtered to limit one or more quantities that are being replicated, the quantity may simply be clipped when it reaches a certain threshold value. Alternatively, a rate of change of the quantity may be transitioned to avoid discontinuities of slope that would introduce artificial high frequency excitations to the system. For example, replay commands may be limited so that an actuator does not strike hard physical stops, but slows gradually as it approaches the ends of its compression and/or extension strokes. The word "gradually" may include staying within a predetermined threshold of the rate of change of the quantity while the desired force and/or distance quantity is kept within its threshold as well.

When implementing the above noted methods, in some embodiments, during motion replay a power or energy consumption of one or more actuators may be limited by one or more controllers to a predetermined maximum value. For example, the energy consumption of one or more actuators may be limited to avoid overheating components of the system. In some embodiments, other sensors such as temperature sensors may be used as feedback mechanisms to limit the actuator output as well to again avoid exceeding a threshold temperature of the systems.

Figure 32:
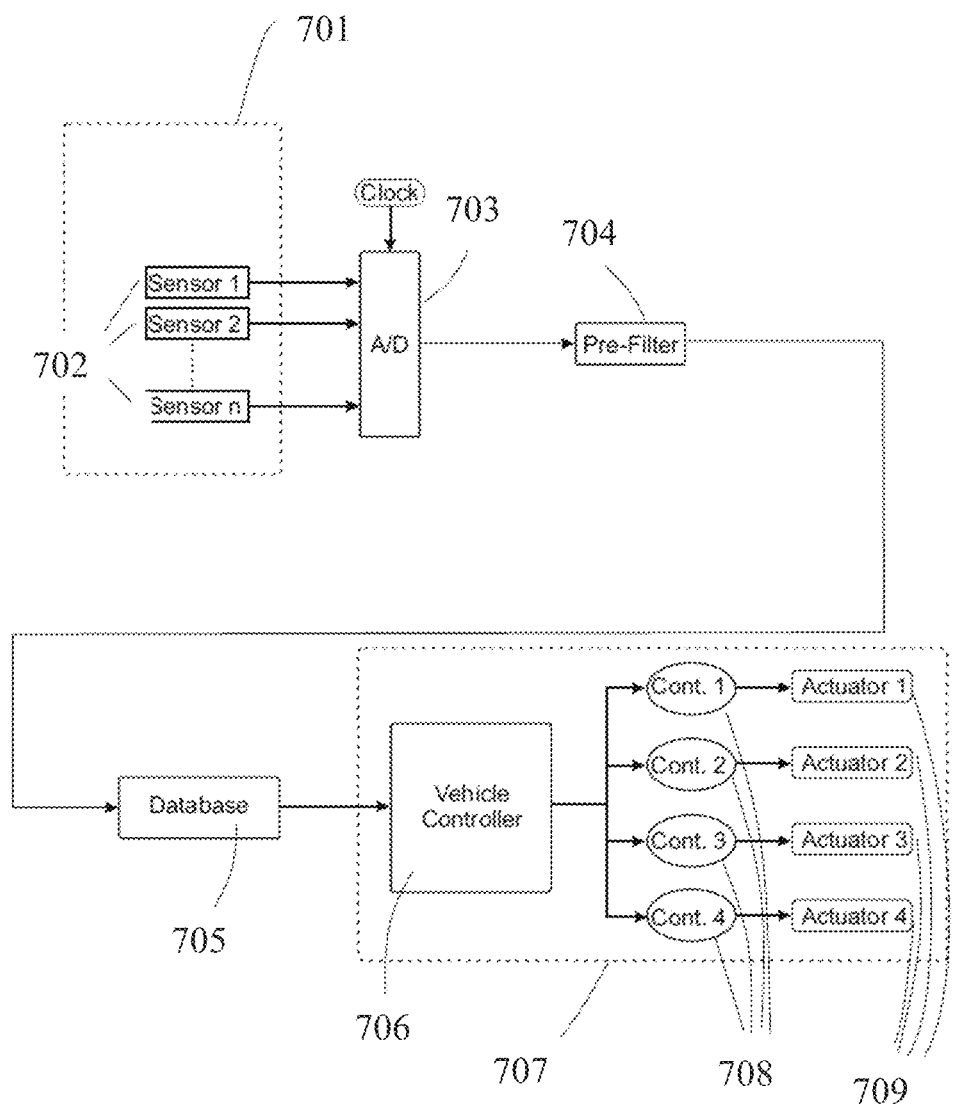
FIG. 32 is a functional block diagram of an embodiment of a system capable of conducting road data collection, pre-filtering, and replay.

FIG. 32 illustrates a functional block diagram for an embodiment of a system for road data collection, pre-filtering, and replay. Vehicle 701 is equipped with one or more sensors 702, such as, for example, an inertial motion unit (IMU), accelerometers, and/or displacement sensors. The data from the sensor(s), if in analog form, may be digitized by a data acquisition system 703.

The capacity of any actuator of an active suspension system is never unlimited. For example, the range of travel and force output of an active suspension actuator is typically capped below either an operational and/or physical threshold. Therefore, the segment of data collected by the instrumented vehicle 701 that is to be replicated may be pre-filtered by a pre-filter 704 to remove aspects of the data that are beyond a threshold capability of one or more actuator(s) 709 of the vehicle. The pre-filtered data may be stored in a database 705 where it may be accessed by an active suppression system controller or vehicle controller 706 of second vehicle 707. The second vehicle 707 may either be the same vehicle, or a different vehicle, from vehicle 701 that was used to collect the road data.

The data accessed by controller 706 is converted into a series of force commands and supplied to the corner controllers 708 associated with the separate actuators of the active suspension system at regular time steps. When these force commands are implemented using the four actuators 709, the road-induced effects (after pre-filtering) are replicated. In this embodiment, each actuator is connected to one wheel assembly of the vehicle. In some embodiments, one or more wheel assemblies may not be attached to an actuator and/or a single wheel assembly may be attached to multiple actuators.

In some embodiments, when road-induced effects are replicated, a vehicle with an active suspension system may be used as a platform for conducting motion sickness tests. Road-induced motion may be replicated in a parked vehicle and one or more test subjects sitting in the vehicle may be exposed to the motion. For example, the vehicle may be used as a testbed to test motion sickness control algorithms under repeatable conditions. In some embodiments, test subjects during motion sickness tests may be requested to perform certain tasks such as, for example, reading from a book, a typed page, a computer or a smart phone. In some embodiments, during the test, the reading material may be secured to the vehicle or otherwise made to move with the vehicle. Alternatively, the reading material may be held by the test subject or moved in a manner to at least partially compensate for vestibular ocular reflex (VOR).

Figure 33:
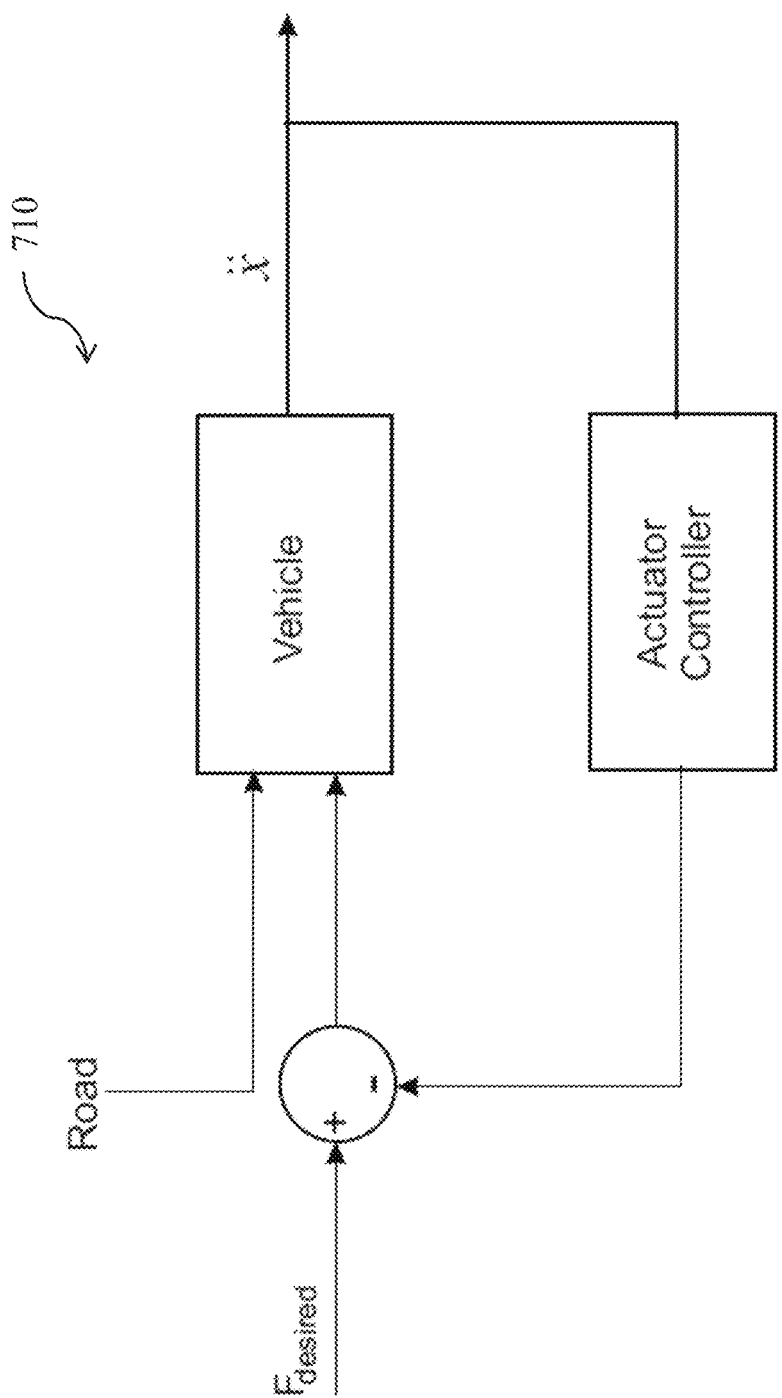
FIG. 33 is a block diagram of an embodiment of a controller reacting to "road input" during playback.

FIG. 33 illustrates a block diagram of a control loop 710 implemented by a controller reacting to replay "road input" transmitted to the controller during playback. In addition, the controller also may implement motion mitigation algorithms at the same time to reduce motion induced by the "road input" on the vehicle. In some embodiments, the road playback isn't pre-filtered in order to mitigate the amount of motion. Rather, the actuator controller acts in real time on the simulated road input induced motion in order to reject the input disturbance and control the body in the desired manner as if the vehicle was traveling on a road. The controller may implement a control scheme similar to that detailed in FIG. 11 above. Therefore, the road (i.e. pre-filtered force commands) imparts some disturbance to the vehicle system. This disturbance is measured with onboard sensors and is mitigated with the feedback through the controller in order to achieve the desired mitigated force command.

Figure 34:
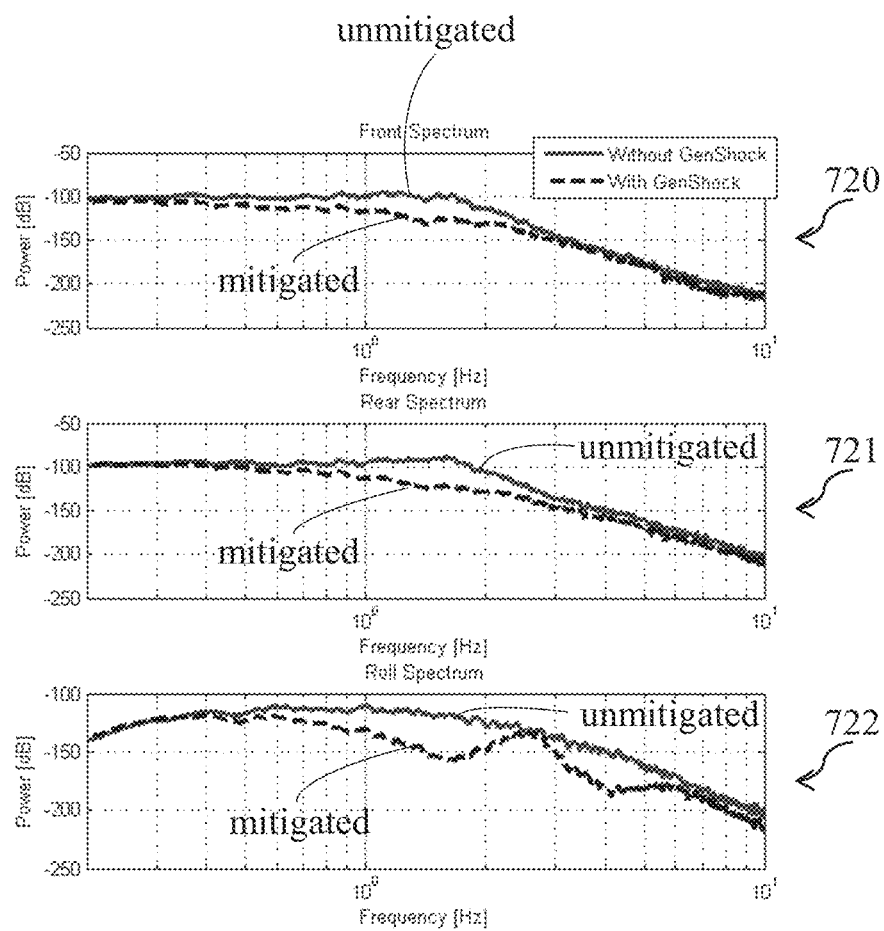
FIG. 34 compares graphs of mitigated and unmitigated frequency spectrum of motion.

FIG. 34 shows a comparison of the mitigated versus unmitigated frequency spectra for different types of motion including front heave motion 720, rear heave motion 721, and roll motion of a vehicle. As shown in the graphs, energy in the 0.3 Hz-2 Hz range is mitigated in the front heave spectrum. However, for rear heave motion, the mitigation is in the 0.3 Hz-6 Hz range. Further, mitigation in the roll spectrum is in the 0.3 Hz-10 Hz range. Of course different motion mitigation performance in different frequency ranges for different suspension systems and/or modes of operation are also contemplated.

In some embodiments, the active suspension system of a vehicle may be used to induce certain vehicle body and/or wheel motions using either predetermined and/or pre-recorded motions while the vehicle is operating at one or more speeds on a vehicle dynamometer. In this way, the effect of vehicle body movement may be studied while the vehicle powertrain is operating at various speeds. Similarly, in some embodiments, pre-recorded road-induced and/or artificially generated vehicle body and/or wheel motion may be generated in a climate chamber for additional studies as well.

In some embodiments, certain motions may also be induced in a vehicle body or a portion of a vehicle with an active suspension system to produce motion that will "rock" a baby to sleep.

In addition to replicating motion, in some embodiments, an active suspension system of a vehicle may be used to induce certain vehicle body and/or wheel motions when the vehicle is parked, for example, in a parking lot, garage, or at another convenient location. These motions may be at least partially synchronized with at least one aspect of a video being observed by one or more occupants of the vehicle. Video may be displayed on displays, for example, attached to the dashboard, seat back, and/or any other location in the vehicle. Alternatively a display may correspond to a display placed on a surface in the vehicle and/or is part of a virtual reality headset, such as for example, an Oculus Rift device. In some embodiments, the system may be integrated into or used with an electric vehicle, wherein electric power may be provided without operating an engine.

The at least partial synchronization of the video with vehicle body movements may be based on a motion track provided, for example, by the producer of the video or a third party. In some embodiments, information used during playback may be at least partially generated by using a vehicle with active suspension. The vehicle motion may be generated by a person using an interface such as, for example, a joystick, a keyboard, or a touch sensitive computer screen for controlling the active suspension system. Vehicle motion may be generated by such a person while watching a video. Motions commanded by such a person may be recorded for later playback. During playback, the active suspension system of a vehicle may be used to cause the vehicle to move in similar fashion and relative timing with the video being displayed.

In some embodiments, the active suspension system may be used to induce certain motions in a vehicle to enhance the occupants' experience while listening to music, watching a video or playing a video game in a vehicle. These motions may be induced in response to a pre-recorded motion track accompanying an audio and/or video recording. They may also be in response to commands given by one or more players of the video game in the vehicle using one or more controller inputs.

In some embodiments the vehicle may be made to respond to music by simulating dancing motions or producing sound that mimics a subwoofer using one or more active suspension systems of the vehicle.

Figure 43:
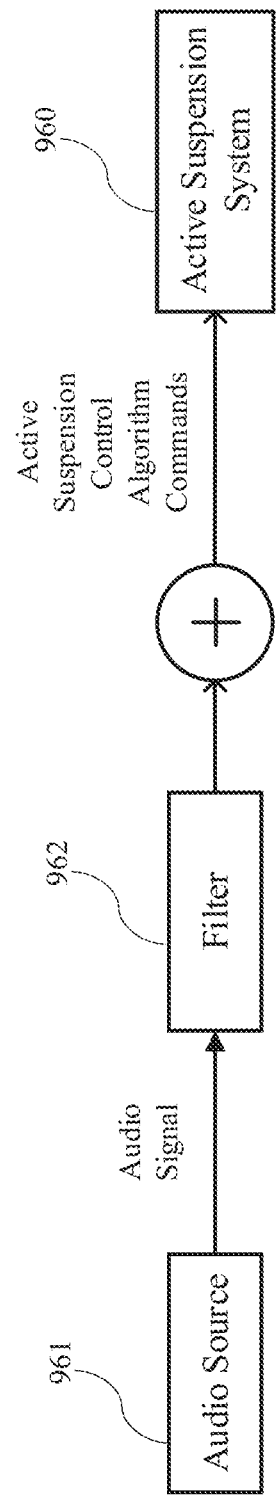
FIG. 43 depicts an audio enhancement system for use in a vehicle using an active suspension system to simulate a high energy subwoofer.

FIG. 43 illustrates a block diagram of an embodiment where an active suspension system 960 is used to cause a vehicle to perform as a subwoofer of a music system. Audio source 961 produces an electronic audio signal that is received by filter 962 which acts as a low pass filter and provides the low frequency content of the audio signal to the active suspension system. In this embodiment, the active suspension system produces low frequency vibration in the vehicle body in response to this filtered audio signal by using one or more suspension system actuators. An active suspension control may operate the active suspension to induce motion in the vehicle to produce these audible vibrations may be produced while the vehicle is stopped and/or while the vehicle is traveling over a road where the active suspension system controls vehicle motion as well as performing the function of a subwoofer. In the embodiment in FIG. 43, the filtered audio signal input into the active suspension controller and played through the active suspension system may augment low frequency vibrations to produce an increased level of low frequency sound. In some embodiments, the low frequency content of the audio signal provided to the active suspension system may be less than or equal to about 300 Hz, 200 Hz, 100 Hz, 80 Hz, 60 Hz, 50 Hz, or any other appropriate frequency. Correspondingly, the frequency input to the active suspension system controller may be greater than or equal to about 10 Hz, 20 Hz, 30 Hz, 40 Hz, or any other appropriate frequency. Combinations of the above ranges are contemplated including a low frequency range played through the active suspension system ranging from about 10 Hz and 300 Hz and 10 Hz to 80 Hz. Of course, frequencies both higher and lower than those noted above, including sub audible frequencies may also be used as the disclosure is not so limited.

In some embodiments, vehicle movement may be choreographed with video game (such as for example one that involves car racing). The movements may be synchronized with video being observed on a virtual reality device such as, for example, the Oculus Rift.

The user interface used to interact with the active suspension system may include, for example, a joystick, a keyboard, leap motion sensor, or a computer touch screen. Alternatively, some of the control devices may include one or more of the vehicle's controls such as the steering wheel, brake, throttle, and/or horn may also be used as inputs to communicate commands to the video game. In some embodiments, when various control devices of the vehicle, such as for example, the steering wheel, are used as an interface for the video game, their normal functions may be disabled. In some embodiments, other devices of the vehicle may be used as outputs to provide additional feedback to the video gamer. For example, air vents or the HVAC system may be activated to blow air in synchrony with actions in the video game. Alternatively or additionally, the air conditioning or heating system may be turned on to more closely simulate the game environment.

In an embodiment, a video game that includes a vehicle in a virtual world (for example, a car, spaceship, airplane, truck, motorcycle, etc.) may use the active suspension of a real operational vehicle to simulate a motion of the simulated vehicle in the virtual world. The person playing the game may utilize a user interface, which may include the controls of the physical vehicle the active suspension is installed on (for example, the steering wheel, brakes, throttle), to cause the virtual world vehicle to turn, accelerate, or perform another maneuver. The right side and/or left side actuators, for example, may then be used to tip the car in a manner that would be expected from the maneuver. For example, if the person playing the video game commands the vehicle to swerve to the left, the actuators may be used to tip the car to the right to a degree that corresponds with the speed of the simulated vehicle navigating a turn.

In some embodiments, vehicle movement may by induced by a controller of the active suspension system operating an active suspension in response to a variety of inputs from the virtual reality game, including for example: road surface condition including roughness, virtual vehicle accelerations (roll, pitch, heave), virtual vehicle RPM's, virtual vehicle gear positions, game sounds, and virtual vehicle health/condition.

In some embodiments, an active suspension system may be made to move in response to music rhythm (real-time algorithm such as for example Winamp). Algorithms may analyze raw audio data in real time to generate vehicle movements. In some embodiments an active suspension system may be used to "visualize" music.

Figure 44:
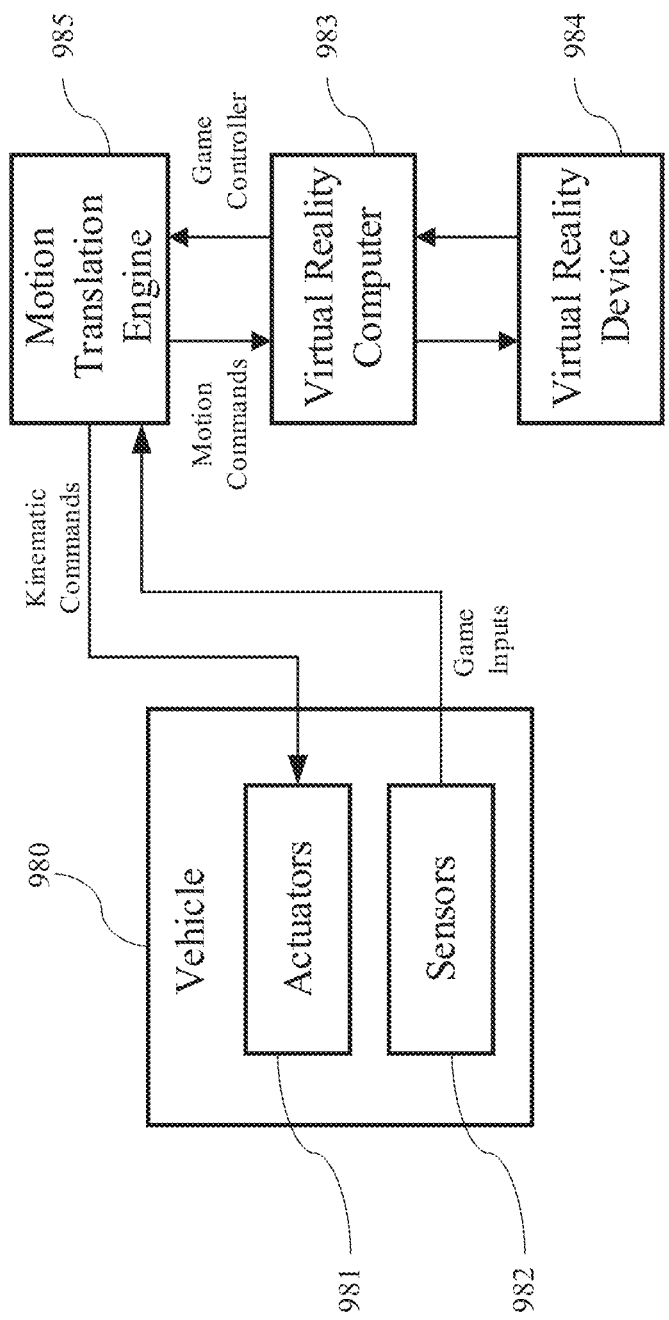
FIG. 44 illustrates a block diagram of a vehicle working in coordination with a virtual reality device.

FIG. 44 illustrates a block diagram of an embodiment of a parked vehicle 980 with an active suspension system that includes active suspension actuators 981 and a suite of sensors 982. A virtual reality computer 983 may be used to produce video and/or sound that can be viewed and/or heard by using a virtual reality device 984. Simultaneously, the virtual reality controller may cause the motion translation engine 984 to provide kinematic commands to one or more actuators of the vehicle causing it to move in a coordinated fashion with what is being viewed and/or heard by the user of the virtual reality device.

Sensors in the vehicle may be used to receive commands from one or more vehicle occupants. In response to these commands, one or more sensors may provide game inputs to the motion translation engine that in turn provides motion commands to the virtual reality computer which may alter what is being viewed and/or heard by the user of the virtual reality device.

Figure 35:
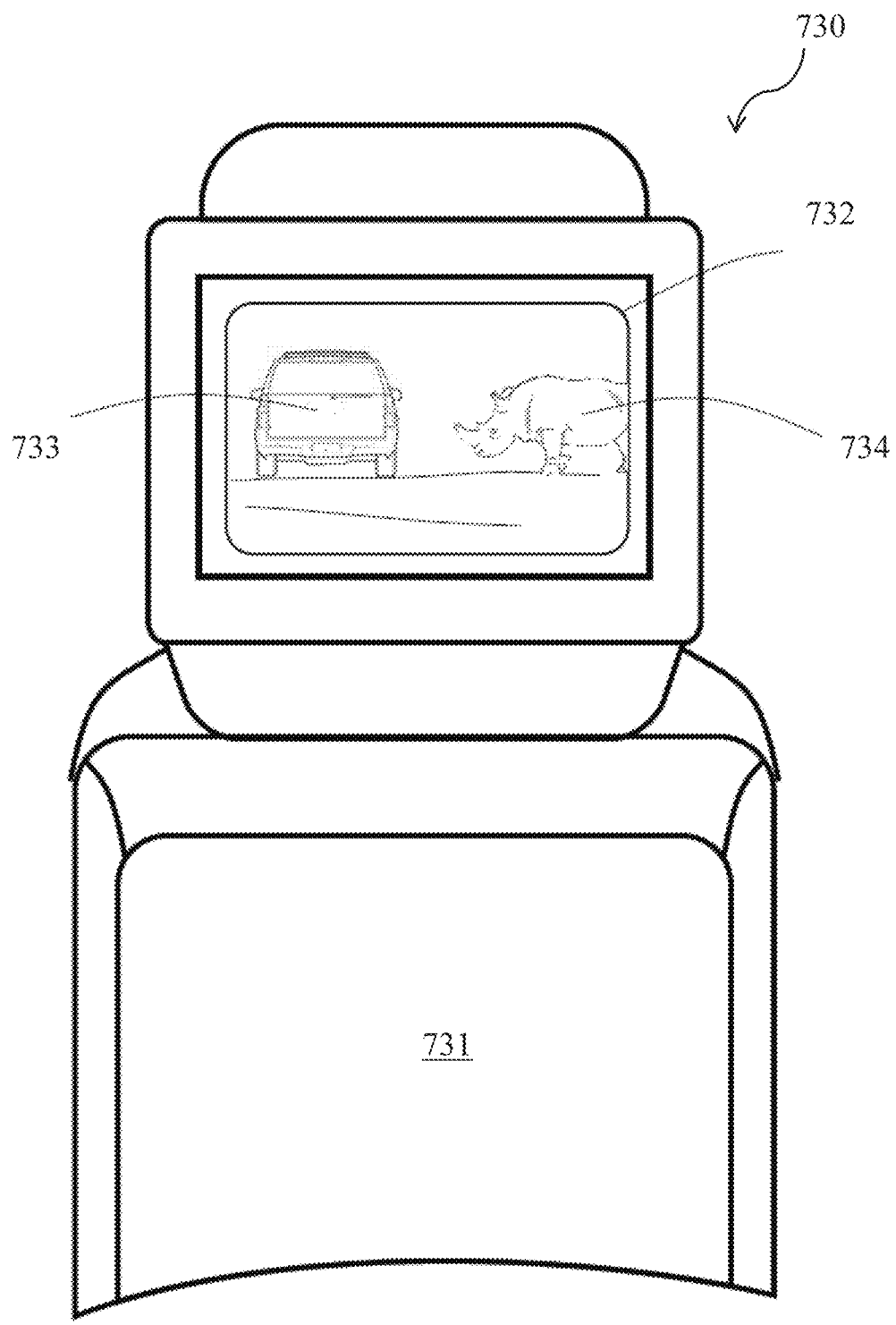
FIG. 35 is a schematic representation of a vehicle seat that includes a video display.

FIG. 35 illustrates the rear view 731 of a vehicle seat 730 in a vehicle that includes a video display 732. Being shown on the video display is a video scene with an image of a vehicle 733 being approached by a rhinoceros 734.

Figure 36:
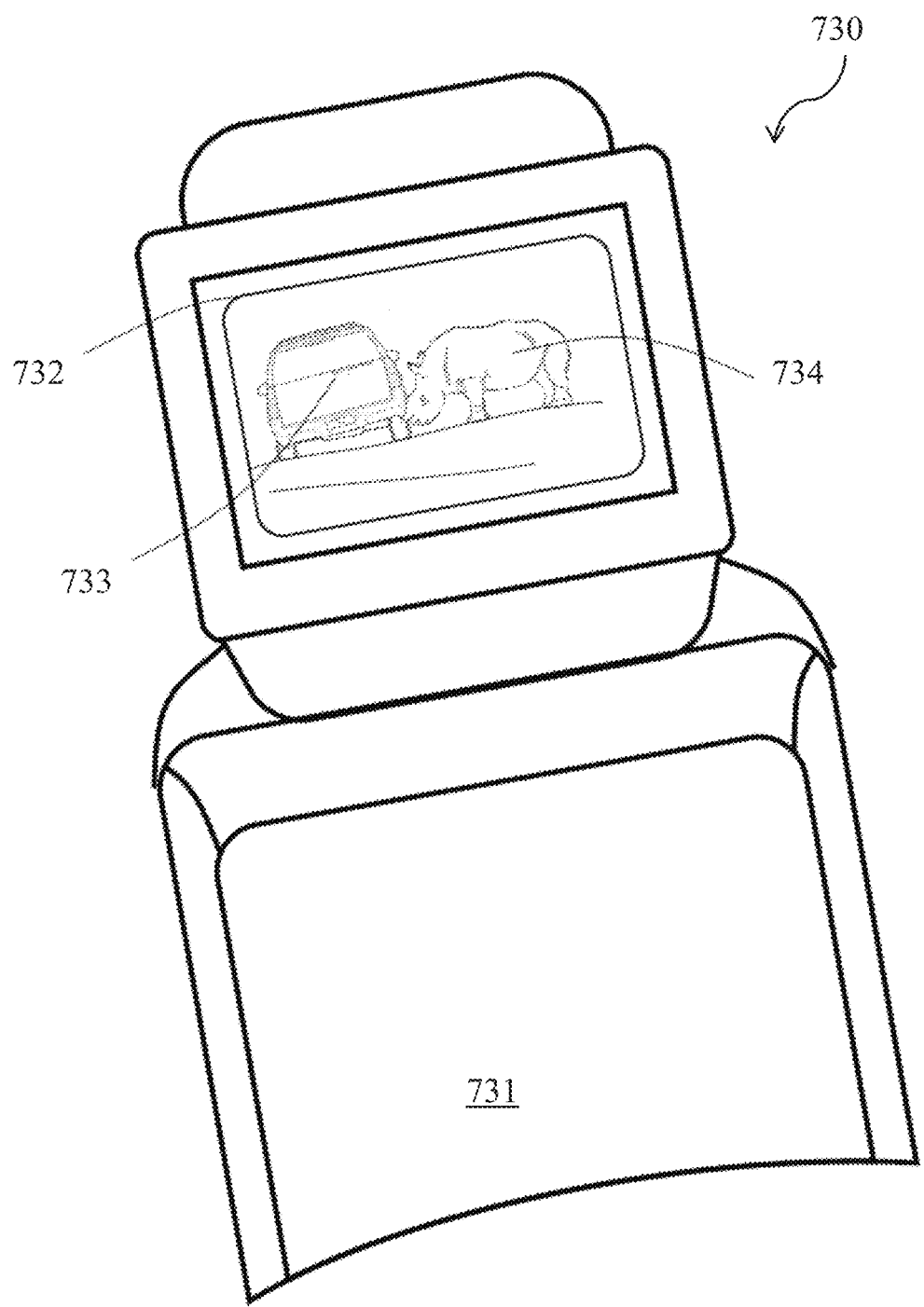
FIG. 36 illustrates the seat of FIG. 35 after the position of the vehicle has been altered in response to what is being shown on the video display.

FIG. 36 illustrates the seat 730 of FIG. 4 after the position of the vehicle has been altered in response to what is being shown on the video display. The scene being shown on the video display has changed from the scene in FIG. 4. Here the rhinoceros 734 has struck the vehicle with such force as to cause the vehicle 733 to lurch to the left. As a result, the active suspension system of the vehicle simultaneously has tipped the vehicle, by applying a roll motion to the vehicle, in which the video is being watched, to the left, creating the illusion that the real vehicle was struck by a rhinoceros as was the vehicle 733 in the video. The active suspension system may time the tipping motion, of the real vehicle, based on a motion track provided with the video or otherwise previously generated while watching the video in the vehicle.

In a somewhat related embodiment, video may be recorded of a vehicle's surroundings while road effects data is being collected. In this way, during replay of road-induced motion in a parked vehicle, a person in the car may also watch the video of the road where the road effects data was obtained. For example, a vehicle may be used to record effects induced in the vehicle while it is traveling over cobblestones.

In this manner, a vehicle with an active suspension system may be used to demonstrate the effectiveness of the system in mitigating road-induced motion. For example, in a dealership showroom, a potential customer may sit in a vehicle when motion induced in the vehicle while traveling over cobblestones, or another road surface, is replicated. The induced motion may then be mitigated by using certain actuator control algorithms as described herein. This experience may be made more effective by showing a video of traveling over cobblestone road during both the mitigated and unmitigated cases.

Figures 45, 46:
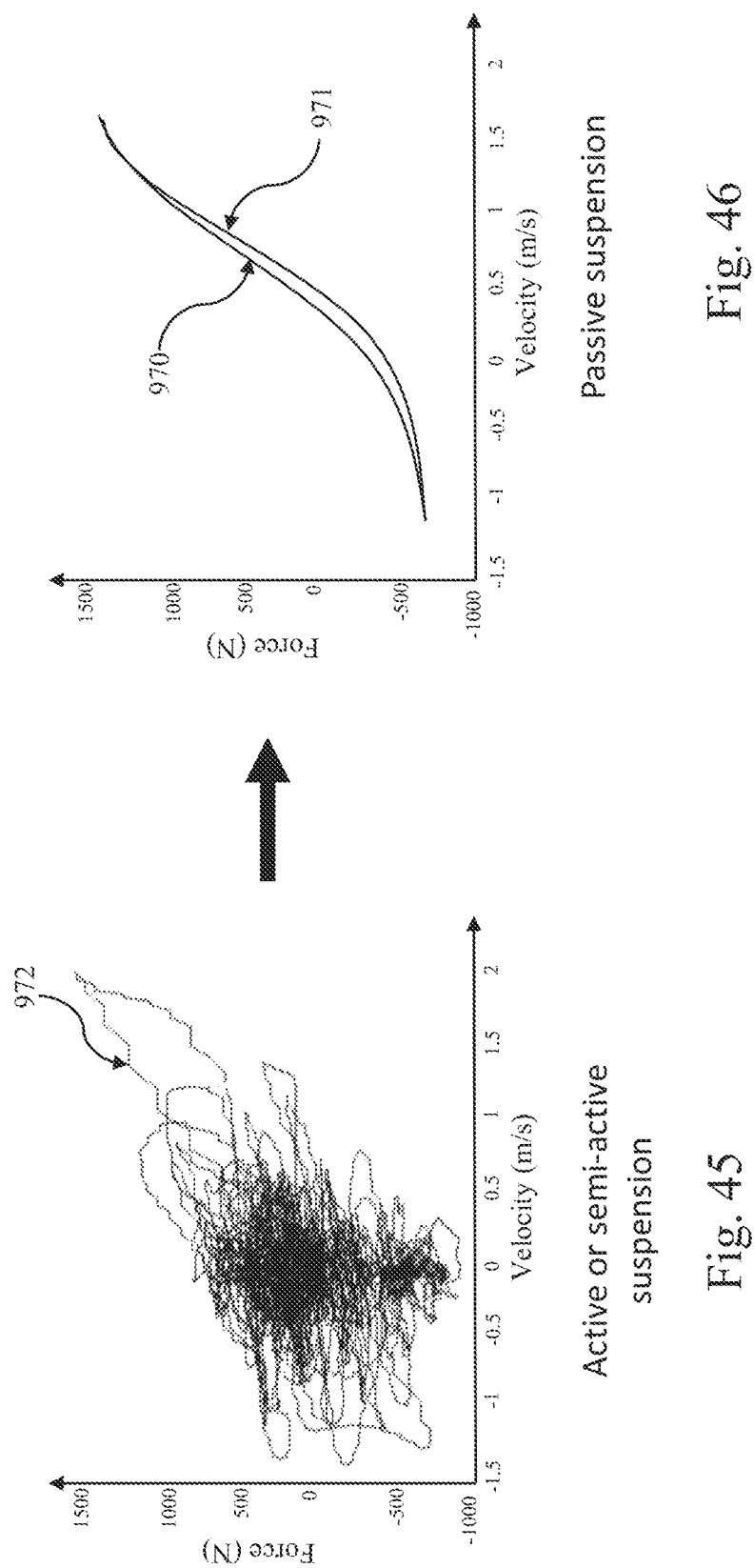
FIG. 45 depicts a force/velocity plot of an active suspension actuator.
FIG. 46 depicts a force/velocity plot of a passive automotive damper.

In some embodiments, the controller of an active or semi-active suspension system may be used to cause the active or semi-active suspension to mimic a passive suspension system. In FIG. 46, curve 970 shows the force/velocity relationship of a passive automotive damper during compression, while curve 971 shows the force/velocity relationship during extension. As can be observed, both of these curves are single value functions and the difference in the two curves is typically caused by hysteresis. Curve 972 in FIG. 45 illustrates a typical force/velocity behavior of an embodiment of an active suspension system where the active suspension system is seen to achieve an almost unlimited combination of force and velocity. Because of this ability, the controller of an active suspension system or that of a semi-active suspension system (not shown) can cause those systems to replicate the force/velocity profiles of curves 970 and 971. The active suspension system may also be commanded to compensate for differences in the spring constant of the springs in the suspension system. Mimicking the performance of a passive suspension system may be used as a marketing tool during, for example, demonstration rides for potential customers at a vehicle dealership. In this manner, a salesman could easily demonstrate the benefits of an active suspension system using a user interface to switch back and forth between active and passive suspension performance for the benefit of the customers.

In some embodiments of an active suspension system, a human machine interface (HMI) may be used to provide increased information to vehicle occupants about the performance of an active suspension system, either when the vehicle is stopped or when the vehicle is traveling over a road. Additionally or alternatively, the HMI may be used to select various modes of operation of the active suspension system.

Figure 47:
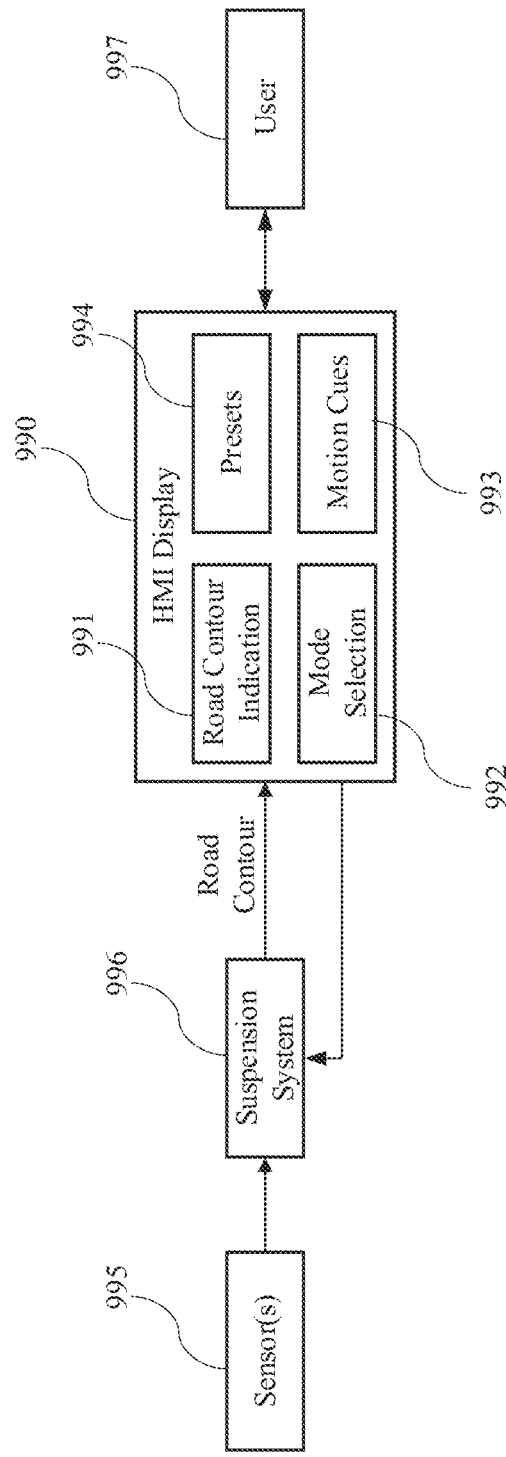
FIG. 47 depicts a block diagram showing the interaction between a human-machine interface, a user, and an active suspension system.

FIG. 47 illustrates an embodiment of an HMI 990 which includes road contour indicator 991, mode selection 992, motion cue selection 993, and presets selector 994. Sensors 995 may be used to measure suspension system 996 performance and/or road disturbance information and providing that information to the HMI controller. In some embodiments, the HMI controller may then display the motion of the car on the HMI display by, for example, using an avatar to represent the vehicle. Road interaction may be illustrated by representing contours that approximate the motion induced in the vehicle's wheels as a result of traveling over the road. The difference between the vehicle motion and the road-induced motion of the vehicle wheels may be shown on the HMI display to illustrate the effectiveness of the active suspension system. The system user 997 may also use the HMI to select vehicle modes that control the behavior of the active suspension system. For example, the user may select a comfort mode where the active suspension system to produce a smooth ride similar to what would be experienced in a large luxury sedan. Alternatively, the user may select a sports car mode where the vehicle more closely hugs the road and follows its vertical movement. The user may also select motion cues that the vehicle can provide, for example during turns and other maneuvers as previously discussed. The vehicle may also use the HMI to select presets for various functions, such as gestures that the vehicle will provide, for example, to greet the owner on the first encounter of the day, to indicate when the car is locked, and to respond to various commands.

Example: Motion Sickness Testing

Motion sickness testing was conducted by using an active suspension system of a vehicle to replicate motion recorded from a vehicle driven around the Boston Massachusetts area under various traffic conditions using a semi-active suspension system. For the tests, a continuous segment of road data spanning 500 seconds was selected for replay in the laboratory using the active suspension system of a vehicle as detailed above. During testing, test subjects read text from a mobile computing device, such as an iPhone, while seated in a vehicle "replaying" the recorded motion for a total of 30 minutes after which they were asked to rate their level of motion sickness from a zero (i.e. no motion sickness) to 10 (i.e. vomiting, retching, and/or dry heaves). Testing was subsequently repeated using the same recorded motions from the semi-active suspension system. However, motion mitigation strategies using the active suspension system as described herein were implemented. Specifically, the active suspension system reduced vehicle motions within the 0.2 Hz to 10 Hz range, see FIG. 34 previously discussed above illustrating the frequency domain comparisons of the PSD of different motions for both the mitigated and unmitigated motions. Of those test subjects who experienced motion sickness during the unmitigated tests, 67% showed no signs of motion sickness during the mitigated motion tests. The remaining 33% of individuals experienced motion sickness during the initial tests reported significant reductions in the rate and severity of the experienced motion sickness.

By using these techniques, the inventors have realized that reducing vehicle roll, pitch and/or heave in certain frequencies outside of those typically associated with motion sickness may greatly reduce motion sickness symptoms within a vehicle. Therefore, as detailed above, in some embodiments, one or more suspension system of a vehicle may be used to negate motions in one or more frequency ranges between 0.05 Hz to 10 Hz, 0.2 Hz to 10 Hz, 0.5 Hz to 10 Hz, 1 Hz to 10 Hz, or any other appropriate frequency range to reduce motion sickness of a vehicle occupant.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computing device or distributed among multiple computing devices. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semi-custom or custom. As a specific example, some commercially available microprocessors have multiple cores such that one or a subset of those cores may constitute a processor. Though, a processor may be implemented using circuitry in any suitable format.

Further, it should be appreciated that a computing device may be embodied in any of a number of forms, such as a rack-mounted computer, a desktop computer, a laptop computer, or a tablet computer. Additionally, a computing device may be embedded in a device not generally regarded as a computing device but with suitable processing capabilities, including a Personal Digital Assistant (PDA), a smart phone or any other suitable portable or fixed electronic device.

Also, a computing device may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Such computing devices may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, the disclosed embodiments may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments of the invention discussed above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the present invention as discussed above. As used herein, the term "computer-readable storage medium" encompasses only a non-transitory computer-readable medium that can be considered to be a manufacture (i.e., article of manufacture) or a machine. Alternatively or additionally, the invention may be embodied as a computer readable medium other than a computer-readable storage medium, such as a propagating signal.

The terms "program", "software", "code", or similar term are used herein in a generic sense to refer to any type of computer code or set of computer-executable instructions that can be employed to program a computing device or other processor to implement various aspects of the present invention as discussed above. Additionally, it should be appreciated that according to one aspect of this embodiment, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art.

Accordingly, the foregoing description and drawings are by way of example only.

The invention claimed is:

1. A method of operating a vehicle that includes an active suspension system, the method comprising:
   with a controller in a first mode of operation, operating at least one active suspension actuator to induce motion in at least a portion of the vehicle to respond to road surface disturbances;
   with the controller in a second mode of operation, operating at least one active suspension actuator to induce a first predefined pattern of motion in a portion of the vehicle; and
   with the controller in a third mode of operation, operating at least one active suspension actuator to induce a second predefined pattern of motion in a portion of the vehicle, wherein the controller is in the third mode of operation when at least one door or at least one window of the vehicle is open.

2. The method of claim 1, wherein the second mode of operation is implemented when the vehicle is parked.

3. The method of claim 1, wherein the first predefined pattern of motion is used to shake snow off of the vehicle.

4. The method of claim 1, wherein the first predefined pattern of motion lowers a front corner of the vehicle nearest to a person to simulate a kneeling posture.

5. The method of claim 1, wherein the first predefined pattern of motion places the vehicle in an entry assist mode.

6. The method of claim 1, wherein the first predefined pattern of motion conveys a visual message to a person outside of the vehicle.

7. The method of claim 6, wherein the visual message is a greeting message.

8. The method of claim 1, further comprising limiting the first predefined pattern of motion when a person outside the vehicle is within a threshold distance from the vehicle.

9. A method of operating a vehicle that includes an active suspension system, the method comprising:
   with a controller in a first mode of operation, operating at least one active suspension actuator to induce motion in at least a portion of the vehicle to respond to road surface disturbances; and
   with the controller in a second mode of operation, operating at least one active suspension actuator to induce a predefined motion in a portion of the vehicle.

10. The method of claim 9, wherein the second mode of operation is implemented when the vehicle is parked.

11. The method of claim 9, wherein the predefined motion is used to shake snow off of the vehicle.

12. The method of claim 9, wherein the predefined motion lowers a front corner of the vehicle nearest to a person to simulate a kneeling posture.

13. The method of claim 9, wherein the predefined motion places the vehicle in an entry assist mode.

14. The method of claim 9, wherein the predefined motion conveys a visual message to a person outside of the vehicle.

15. The method of claim 14, wherein the visual message is a greeting message.

16. The method of claim 9, further comprising limiting the predefined motion when a person outside the vehicle is within a threshold distance from the vehicle.

17. A method of operating a vehicle that includes an active suspension system, the method comprising:
- with a controller in a first mode of operation, operating at least a first active suspension actuator to induce motion in at least a portion of the vehicle to respond to a road surface disturbance; and
- with the controller in a second mode of operation, operating at least the first active suspension actuator to induce a predefined pattern of motion in a portion of the vehicle;
- wherein the predefined pattern of motion is a predetermined excitation motion configured to diagnose a malfunction of at least one system in the vehicle.

18. The method of claim 17, wherein the at least one system includes a second active suspension actuator.

19. The method of claim 17, wherein the at least one system includes a sensor system.

20. The method of claim 1, wherein the second predefined pattern of motion has an amplitude that is less than an amplitude of the first predefined pattern of motion.

21. The method of claim 1, wherein the controller is in the third mode of operation when at least one door of the vehicle is open.

22. The method of claim 1, wherein the controller is in the third mode of operation when at least one window of the vehicle is open.

* * * * *